(12) United States Patent
Phillips et al.

(10) Patent No.: US 9,932,360 B2
(45) Date of Patent: Apr. 3, 2018

(54) QUALITATIVE AND QUANTITATIVE POINT-OF-CARE ASSAYS

(71) Applicant: The Penn State Research Foundation, University Park, PA (US)

(72) Inventors: Scott Thomas Phillips, State College, PA (US); Gregory Gerald Lewis, Syracuse, NY (US); Jessica Sloane Robbins, New York, NY (US)

(73) Assignee: The Penn State Research Foundation, University Park, PA (US)

( * ) Notice: Subject to any disclaimer, the term of this patent is extended or adjusted under 35 U.S.C. 154(b) by 724 days.

(21) Appl. No.: 14/311,036

(22) Filed: Jun. 20, 2014

(65) Prior Publication Data
US 2015/0005193 A1 Jan. 1, 2015

Related U.S. Application Data

(60) Provisional application No. 61/900,555, filed on Nov. 6, 2013, provisional application No. 61/838,097, filed on Jun. 21, 2013.

(51) Int. Cl.
C07F 5/02 (2006.01)
G01N 33/52 (2006.01)
C12Q 1/26 (2006.01)

(52) U.S. Cl.
CPC .............. *C07F 5/027* (2013.01); *C07F 5/025* (2013.01); *C12Q 1/26* (2013.01); *G01N 33/525* (2013.01); *Y10T 436/206664* (2015.01)

(58) Field of Classification Search
CPC ......... B01L 2300/126; B01L 2300/161; B01L 2200/16; G01N 33/558; G01N 33/52; G01N 21/77; G01N 33/525; C07F 5/027; C07F 5/025; C12Q 1/26; Y10T 436/206664
See application file for complete search history.

(56) References Cited

U.S. PATENT DOCUMENTS

| 6,951,682 | B1 * | 10/2005 | Zebala ................. | B01J 19/0046 428/312.2 |
| 8,124,421 | B2 | 2/2012 | Feaster et al. | |
| 8,377,710 | B2 | 2/2013 | Whitesides et al. | |
| 2005/0069462 | A1 | 3/2005 | Humenik et al. | |
| 2009/0298191 | A1 * | 12/2009 | Whitesides .......... | G01N 33/523 436/164 |
| 2011/0111517 | A1 | 5/2011 | Siegel et al. | |
| 2012/0107851 | A1 | 5/2012 | Killard et al. | |
| 2012/0238008 | A1 | 9/2012 | Henry et al. | |
| 2012/0302456 | A1 | 11/2012 | Whitesides et al. | |
| 2013/0078711 | A1 | 3/2013 | Chen et al. | |

OTHER PUBLICATIONS

Lewis et al.(Angew. Chem. Int. Ed. 2012, 51, 12707-12710.*
Fung et al.(Anal Bioanal Chem (2009) 393:1281-1287).*
(Continued)

*Primary Examiner* — Sally A Merkling
(74) *Attorney, Agent, or Firm* — Buchanan Ingersoll & Rooney PC

(57) ABSTRACT

Disclosed herein are "equipment-free" flow-through assay devices based on patterned porous media, methods of making same, and methods of using same. The porous, hydrophilic media are patterned with hydrophobic barriers for performing assays on liquids.

16 Claims, 26 Drawing Sheets

(56) References Cited

OTHER PUBLICATIONS

Karton-Lifshin et al. New J. Chem, 2012, 36, 386-393. Available Sep. 23, 2011.*
Sella et al. J. Am. Chem Soc. 2010, 132, 3945-3952.*
Results of STIC Structure Search.*
Aili et al., "Hybrid Nanoparticle-Liposome Detection of Phospholipase activity," Nano Lett., 2011, 11, 1401.
Allen et al., "A Noninstrumental Quantitative Test System and Its Application for Determining Cholesterol Concentration in Whole Blood," Clin. Chem. 1990, 36, 1591.
Baker et al., "A Two-Component Small Molecule System for Activity-Based Detection and Signal Amplification: Application to the Visual Detection of Threshold Levels of PD(II)," J. Am. Chem. Soc., 2011, 133, 5170.
Bruzewicz et al., "Low-Cost Printing of Poly(dimethylsiloxane) Barriers to Define Microchannels in Paper," Anal Chem, 2008, 80, 3387-3392.
Carrilho et al., "Understanding Wax Printing: A Simple Micropatterning Process for Paper-Based Microfluidics," Anal Chem, 2009, 81, 7091-7095.
Cate et al., "Simple, distance-based measurement for paper analytical devices," Lab Chip, 2013, 13, 2397.
Chatterjee et al., "Flow valve microfluidic devices for simple, detectorless and-free analyte quantitation," Anal. Chem., 2012, 84, 7057.
Chen et al., "Self-Immolative Polymers Containing Rapidly Cyclizing Spacers: Toward Rapid Depolymerization Rates," Macromolecules 2012, 45, 7364-7374.
Cheng et al., "Paper-based ELISA," Angew. Chem. Int. Ed. 2010, 49, 4771-4774.
Cheng et al., Angew. Chem. 2010, 122, 4881-4884.
Cho et al., "Modern reaction-based indicator systems," Chem. Soc. Rev. 2009, 38, 1647-1662.
Cho et al., "Semiquantitative, Bar Code Version of Immunochromatographic Assay System for Human Serum Albumin as Model Analyte," Biotechnol. Bioeng., 2001, 75, 725.
Claeys et al., "Formation of secondary organic aerosols from isoprene and its gas-phase oxidation products through reaction with hydrogen peroxide," Atmos. Environ. 2004, 38, 4093-4098.
De Garcia Lux et al., "Single UV or Near IR Triggering Event Leads to Polymer Degradation into Small Molecules," ACS Macro Lett. 2012, 1, 922-926.
De La Rica et al., "Plasmonic ELISA for the ultrasensitive detection of disease biomarkers with the naked eye," Nature Nanotechnology, 2012, vol. 7, 821-824.
Delaney et al., "Electrogenerated chemiluminescence detection in paper-based microfluidic sensors," Anal. Chem. 2011, 83, 1300-1306.
Dewitt et al., "A cascade biodegradable polymer based on alternating cyclization and elimination reactions," J. Am. Chem. Soc. 2009, 131, 18327-18334.
Dilauro et al., "Reproducible and Scalable Synthesis of End-Cap-Functionalized Depolymerizable Poly(phthalaldehydes)" Macromolecules, 2013, 46(8), pp. 2963-2968, DOI: 10.1021/ma4001594.
Dilauro et al., "Accessibility of Responsive End-Caps in Films Composed of Stimuli-Responsive, Depolymerizable Poly(phthalaldehydes)" Macromolecules, 2013, 46(18), pp. 7257-7265.
Dungchai et al., "A low-cost, simple, and rapid fabrication method for paper-based microfluidics using wax screen-printing," Analyst, 2011, 136, 77-82.
Dungchai et al., "Determination of aerosol oxidative activity using silver nanoparticle aggregation on paper-based analytical devices," Analyst, 2013, 138(22):6766-73, DOI: 10.1039/c3an01235b.
Dungchai et al., "Electrochemical detection for paper-based microfluidics," Anal. Chem. 2009, 81, 5821-5826.
Ellerbee et al., "Quantifying colorimetric assays in paper-based microfluidic devices by measuring the transmission of light through paper," Anal. Chem. 2009, 81, 8447-8452.
Esser-Kahn et al., "Programmable microcapsules from self-immolative polymers," J. Am. Chem. Soc. 2010, 132, 10266-10268.
Esser-Kahn et al., "Triggered Release from Polymer Capsules," Macromolecules 2011, 44, 5539-5553.
Fu et al., "Transport in two-dimensional paper networks," Microfluid. Nanofluid. 2011, 10, 29-35.
Fung et al., "Development of enzyme-based bar code-style lateral-flow assay for hydrogen peroxide determination," Analytica Chimica Acta, 2009, 634, 89-95.
Giljohann et al.,"Drivers of biodiagnostic development," Nature 2009, 462, 461-464.
Guidelines for Drinking-water Quality, World Health Organization, Geneva, Switzerland, 4th edn., 2011.
Halliwell et al., "Hydrogen peroxide in the human body," FEBS Letters, 2000, 486, 10-13.
Huynh et al., "Chemical analog-to-digital signal conversion based on robust threshold chemistry and its evaluation in the context of microfluidics-based quantitative assays," J. Am. Chem. Soc., 2013, 135, 14775.
Leung et al., "InfectCheck barcode-style lateral flow assay for semi-quantitative detection of C-reactive protein in distinguishing between bacterial and viral infections," J. Immunol. Methods, 2008, 336, 30.
Lewis et al., "A prototype point-of-use assay for measuring heavy metal contamination in water using time as a quantitative readout," ChemComm, 2014, 50, 5352.
Lewis et al., "High throughput method for prototyping three-dimensional, paper-based microfluidic devices," Lab Chip, 2012, 12, 2630-2633.
Lewis et al., "Phase-Switching Depolymerizable Poly(carbomates) Oligomers for Signal Amplification in Quantitative Time Based Assays," Macromolecules, 2013, 46, 5177-5183.
Lewis et al., "Point-of-Care Assay Plataform for Quantifying Active Enzymes to Femtomolar Levels Using Measurement of Time as the Readout," Anal. Chem., 2013, 85 (21), pp. 10432-10439. DOI: 10.1021/ac402415v.
Lewis et al., "Quantifying Analytes in Paper-Based Microfluidic Devices Without Using Extarnal Electronic Readers," Angew. Chem. Int. Ed., 2012, 51, 12707-12710.
Lippert et al., "Boronate oxidation as a bioorthogonal reaction approach for studying the chemistry of hydrogen peroxide in living systems," Acc. Chem. Res. 2011, 44, 793-804.
Liu et al., "Aptamer-based Origami Paper Analytical Device for Electrochemical Detection of Adenosine," Angew. Chem. Int. Ed., 2012, 51, 6925.
Liu et al., "Three-Dimensional Paper Microfluidic Devices Assembled Using the Principles of Origami," Journal of the American Chemical Society, 2011, 133, 17564-17566.
Lou et al., "One-step competitive immunochromatographic assay for semiquantitative determination of lipoprotein(a) in plasma," J. Clin. Chem., 1993, 39, 619.
Lu et al., "Rapid prototyping of paper-based microfluidics with wax for low-cost, portable bioassay," Electrophoresis 2009, 30, 1497-1500.
Martinez et al., "FLASH: A rapid method for prototyping paper-based microfluidic devices," Lab Chip, 2008, 8, 2146-2150.
Martinez et al., "Patterned paper as a platform for inexpensive, low-volume, portable bioassays," Angew Chem Int Ed, 2007, 46, 1318-1320.
Martinez et al., "Programmable diagnostic devices made from paper and tape," Lab Chip, 2010, 10, 2499-2504.
Martinez et al., "Simple telemedicine for developing regions: Camera phones and paper-based microfluidic devices for real-time, off-site diagnosis," Anal. Chem. 2008, 80, 3699-3707.
Martinez et al., "Three-dimensional microfluidic devices fabricated in layered paper and tape," Proc. Natl. Acad. Sci. USA, 2008, 105, 19606-19611.
Mentele et al., "Microfluidic paper-based analytical device for particulate metals," Anal.Chem., 2012, 84, 4474.
Nie et al., "Electrochemical sensing in paper-based microfluidic devices," Lab Chip, 2010, 10, 477.
Noh et al., "Fluidic Timers for Time-Dependent, Point-of-Care Assays on Paper," Anal Chem, 2010, 82, 8071-8078.

(56) References Cited

OTHER PUBLICATIONS

Noh et al., Anal Chem, "Metering the Capillary-Driven Flow of Fluids in Paper-Based Microfluidic Devices," 2010, 82, 4181-4187.
Ortiz et al., "Hydrogen peroxide deposition and decomposition in rain and dew waters," Atmos. Environ. 2000, 34, 1139-1146.
Pangborn et al., "Safe and Convenient Procedure for Solvent Purification," Organometallics 1996, 15, 1518-1520.
Peeling et al., "Rapid tests for sexually transmitted infections (STIs): the way forward," Sex Transm. Infect. 2006, 82, v1-6.
Peterson et al., "Controlled depolymerization: Stimuli-responsive self-immolative polymers," Macromolecules 2012, 45, 7317-7328.
Robbins et al., "Effects of Electronics, Aromaticity, and Solvent Polarity on the Rate of Azaquinone-Methide-Mediated Depolymerization of Aromatic Carbamate Oligomers," Org. Chem. 2013, 78, 3159-3169.
Sagi et al., "Self-Immolative Polymers," J. Am. Chem. Soc. 2008, 130, 5434-5435.
Schmid et al., "A Self-Immolative Spacer That Enables Tunable Controlled Release of Phenols under Neutral Conditions," J. Org. Chem, 2012, 77, 4363-4374.
Scida et al., "DNA Detection Using Origami Paper Analytical Devices," Analytical Chemistry, 2013, 9713-9720.
Scrimin et al., "Sensing through signal amplification," Chem. Soc. Rev. 2011, 40, 4488-4505.
Seo et al., "Patterned Plastic That Change Physical Structure in Response to Applied Chemical Signals," J. Am. Chem. Soc. 2010, 132, 9234-9235.
Song et al., "Multiplexed volumetric bar-chart chip for point-of-care diagnostics," Nat. Commun., 2012, 3,1283.
Still et al., "Rapid Chromatographic Technique for Preparative Separations with Moderate Resolution," J. Org. Chem. 1978, 43, 2923-2925.
Taniai et al., "Monitoring of Hydrogen Peroxide, Nitrate and Nitrite in Rain Water," Anal. Sci. 2000, 16, 275-281.
Thom et al., "Fluidic batteries as low-cost sources of power in paper-based microfluidic devices," Lab Chip 2012, 12, 1768-1770.
Tietz, N. W., "Clinical Guide to Laboratory Tests," 1995, Chapter 25, p. 871.
Urdea et al., "Requirements for high impact diagnostics in the developing world," Nature 2006, 444, 73-79.
Waghmare et al., "A comprehensive theorical model of capillary transport in rectangular microchannels," Microfluid. Nanofluid. 2012, 12, 53-63.
Wang et al., "Label-Free Colorimetric Detection of Lead Ions with a Nanomolar Detection Limit and Tunable Dynamic Range b using Gold Nanoparticles and DNAzyme," Adv. Mater., 2008, 20, 3263.
Weinstain et al., "Self-immolative comb-polymers: multiple-release of side-reporters by a single stimulus event," Chem. Eur. J. 2008, 14, 6857-6861.
Wong et al., "Amplified Release Through the Stimulus Triggered Degradation of Self-immolative Oligomers, Dendrimers, and Linear Polymers," Adv. Drug Delivery Rev. 2012, 64, 1031-1045.
Wu et al., "Motion-based DNA detection using catalytic nanomotors," Nat. Commun., 2010, 1,36.
Xiang et al., "An invasive DNA approach toward a general method for portable quantification of metal ions using a personal glucose meter," Chem. Commun., 2013, 49, 585.
Xue et al., "One-step, room temperature, colorimetric detection of mercury (Hg2+) using DNA/nanoparticle conjugates," J. Am. Chem. Soc., 2008, 130, 3244.
Yager et al., "Microfluidic diagnostic technologies for global public health," Nature 2006, 442, 412-418.
Yager et al., "Point-of-care diagnostics for global health," J. Annu. Rev. Biomed. Eng. 2008, 10, 107-144.
Yang et al., "A simple, rapid, low cost diagnostic test for sickle cell disease," Lab Chip, 2013, 13, 1464.
Yuan et al., "Highly Selective and Sensitive Detection of Mercuric Ion Based on a Visual Fluorescence Method," Anal. Chem., 2012, 84, 9792.
Zhang et al., "Self-Powered Microscale Pumps Based on Analyte-Initiated Depolymerization Reactions," Angew. Chem. Int. Ed. 2012, 51, 2400-2404.
Zhang et al., "Three-dimensional paper-based electrochemiluminescence device for simultaneous detection of Pb2+ and Hg2+ based on potential-control technique," Biosens. Bioelctron., 2013, 41, 544.
Zong et al., "Label-free quantitation of peptide release from neurons in a microfluidic device with mass spectrometry imaging," Lab Chip, 2012, 12, 2037.

\* cited by examiner

QUALITATIVE AND QUANTITATIVE POINT-OF-CARE ASSAYS

CROSS-REFERENCE TO RELATED APPLICATIONS

This application claims priority to U.S. Provisional Patent Application No. 61/838,097 filed Jun. 21, 2013, and U.S. Provisional Patent Application No. 61/900,555 filed Nov. 6, 2013, the contents of each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Sep. 11, 2014, is named 2013-4090-032360-9009-US02-SEQ-LIST-09-11-14.txt, and is 2,407 bytes in size.

STATEMENT OF GOVERNMENT INTEREST

This invention was made with government support under Grant No. CHE1150969 awarded by the National Science Foundation. The Government has certain rights in the invention.

TECHNICAL FIELD

The present disclosure relates generally to point-of-care (POC) diagnostic devices.

BACKGROUND

Point-of-care (POC) diagnostic devices can be used to address a variety of needs, from water quality to detection of infectious diseases. A long-standing challenge in the area of point-of-care (POC) diagnostics has been the development of operationally-simple and inexpensive platforms for conducting reproducible and rapid quantitative assays. While qualitative assays are available in the form of dipsticks and lateral-flow tests, quantitative assays pose practical challenges that have been difficult to overcome in an inexpensive and convenient way.

In resource-limited environments, POC assays need to be low cost; provide rapid, sensitive results; contain thermally stable reagents; and minimize required equipment and training. Lateral flow assays fulfill these requirements but are unable to quantify analytes within a sample.

Quantitative POC assays typically require the use of an electronic reader capable of analyzing the output of an assay at a fixed assay time. These electronic readers can range from digital cameras (e.g., cell phone cameras) for performing colorimetric assays to digital multimeters for performing electrochemical assays. These readers require a power source, such as batteries, that increases the cost of performing quantitative POC assays. In addition to increased costs, these readers add additional levels of complexity to assays (e.g., proper imaging techniques, analysis of imaging, and preparation of samples for imaging), reducing their applicability in resource-limited environments. The ideal quantitative POC assay, particularly for use in resource-limited environments such as the developing world, not only should be inexpensive, straightforward to operate, and provide rapid and reproducible quantitative results, but it also should do so without requiring use of an external "reader", such as cell phone cameras, glucose meters, conductivity meters, or any number of specialized electronic devices that could be paired with an assay.

SUMMARY

In one aspect, provided are capillary-driven devices capable of quantifying analytes within a sample without using a standard electronic reader. A hydrophobic detection reagent may be included within a porous media, wherein the hydrophobic reagent can change to hydrophilic by the presence of the target analyte. The detection reagent can respond to hydrogen peroxide to convert from hydrophobic to hydrophilic molecules. The detection reagent can be, but is not limited to, a small molecule, oligomer, or polymer. The device can be a capillary-driven vertical flow-through device. The device can be a capillary-driven lateral flow device. The device may include layers of hydrophilic, porous media and a physical hydrophobic barrier, including, but not limited to, photoresist, polystyrene, PDMS and waxes that may define hydrophilic regions including, but not limited to microchannels and reservoirs. The hydrophilic, porous media layers can be held in contact through an adhesive including, but not limited to, spray adhesive, laminate and double-sided tape. Buffer salts including, but not limited to, HEPES and phosphate buffer may be included within the defined hydrophilic regions. A detection reagent that responds selectively to a specific analyte may be included within defined hydrophilic regions. A dye, or coloring agent, may be included within the defined hydrophilic regions. Salts may be included for conducting an electric current.

The analyte may be quantified by measuring time using a timer (digital or analog). The analyte may be quantified by measuring time using a fluidic timer. A fluidic timer can include, but is not limited to, regions of the device modulated with a hydrophobic molecule (e.g., paraffin wax) that can affect the wicking properties of the region. Variations in the quantity/type or hydrophobic molecule can allow for control over the time for a sample to wick through the device. The analyte may be quantified by counting colored assay regions at a fixed assay time. The device may further comprise a responsive reagent(s) configured to contact the sample, wherein the responsive reagent(s) specifically targets the analyte and interacts with the detection reagent to produce a response. The responsive reagent(s) can be selected to react with the analyte and produce hydrogen peroxide, which can convert the detection reagent from hydrophobic to hydrophilic. The responsive reagent(s) may be a small-molecule substrate. The responsive reagent(s) may be an enzyme. The responsive reagent(s) may be a substrate-enzyme complex. The responsive reagent(s) may be an aptamer-enzyme-substrate complex. A plurality of different responsive reagents may be included in the same layer.

In certain embodiments, the sample can be added to the first layer, containing a defined hydrophilic region. Capillary action can drive the liquid sample from the first layer to the next layer. The sample may redissolve the buffer salts contained in the second layer and then may wick into the next layer. The detection reagent may be present within the following layer or plurality of layers. The sample may contact the detection reagent, wherein the detection reagent can be converted to hydrophilic molecules when hydrogen peroxide is present within the sample. The sample can be wicked to the layer containing the dye, redissolving the dye and becoming colored. The colored sample solution may wick to the last layer, the visualization layer, providing a colored indication of assay completion. The concentration of analyte within the sample can be determined by measuring the time from when the sample is added to the first layer to when a color change is observed in the visualization layer.

In certain embodiments, the device can include a control channel. The sample may be added to the first layer, containing a defined hydrophilic region. Capillary action can drive the liquid sample from the first layer to the next layer. The sample can redissolve the buffer salts contained in the second layer, split into two separate channels (the "assay" channel and the "control" channel), and then may be wicked into the next layer. The sample in each channel then may encounter a region containing the responsive reagent(s). In the "assay" channel the responsive reagent(s) can be chosen to react to the presence of the analyte to generate hydrogen peroxide. The responsive reagent(s) may be chosen for the "control" channel so that even in the presence of the analyte, hydrogen peroxide is not generated. The composition of the responsive reagent(s) in both the "assay" and "control" channels can be similar enough to provide similar effects on sample wicking rates when interacting with the sample. The detection reagent may be present within the following layer or plurality of layers. The sample can contact the detection reagent, wherein the detection reagent can be converted to hydrophilic molecules when hydrogen peroxide is present and/or generated due to the presence of the analyte within the sample. The sample may be wicked to the layer containing the dye, redissolving the dye and becoming colored. The colored sample solution can wick to the visualization layer, providing a colored indication of when the assay is complete. The concentration of analyte within the sample may be determined by measuring the time from when the visualization region of the "assay" channel changes color to when a color change is observed in the visualization layer of the "control" channel.

In certain embodiments, the device can include a plurality of channels. The sample may be added to the first layer, containing a defined hydrophilic region. Capillary action can drive the liquid sample from the first layer to the next layer(s). The following layer may split the sample into a plurality of channels (e.g., from 2-25) via lateral flow microchannels arranged in a circular pattern. The sample can wick from each separate channel into the next layer, containing buffer salts. The sample can redissolve the buffer salts contained in the layer, and then may be wicked into the next layer. The detection reagent can be present within the following layer or plurality of layers. The sample can contact the detection reagent, wherein the detection reagent may be converted to hydrophilic when hydrogen peroxide is present within the sample. Each subsequent channel around the circular arrangement may contain increasing quantities of the detection reagent. The sample may be wicked to the layer containing the dye, redissolving the dye and becoming colored. The colored sample solution can wick to the visualization layer, providing a colored indication of when the assay is complete within that channel. The concentration of analyte within the sample can be determined by counting the number of channels where a color change is visible in the visualization layer after a fixed assay time has elapsed (e.g., 5, 10 or 15 minutes).

Determining the concentration of the analyte in the sample may comprise measuring the time for the sample to flow through the device after addition of the sample. Determining the concentration of the analyte in the sample may comprise measuring the difference in time between an "assay" channel and a "control" channel. Determining the concentration of the analyte in the sample may comprise counting the number of channels where a color change has occurred within a fixed period of time.

In another aspect, disclosed is a capillary-driven device, including a hydrophobic detection reagent in a porous media, wherein the hydrophobic reagent changes to hydrophilic by the presence of a target analyte. The device can be capable of quantifying analytes within a sample without using a standard electronic reader. The device can be a capillary-driven vertical flow-through device, a capillary-driven lateral flow-through device, or a combination thereof.

The hydrophobic detection reagent can be a responsive small molecule, oligomer, or polymer. The hydrophobic detection reagent can be selected from a carbamate, ether, polyether, a poly(phthalaldehyde), a polyvinyl carbamate, a polybenzyl carbamate, or a combination thereof. The hydrophobic detection reagent can respond to hydrogen peroxide to convert from hydrophobic to hydrophilic molecules.

The hydrophobic detection reagent can be a compound of formula (I),

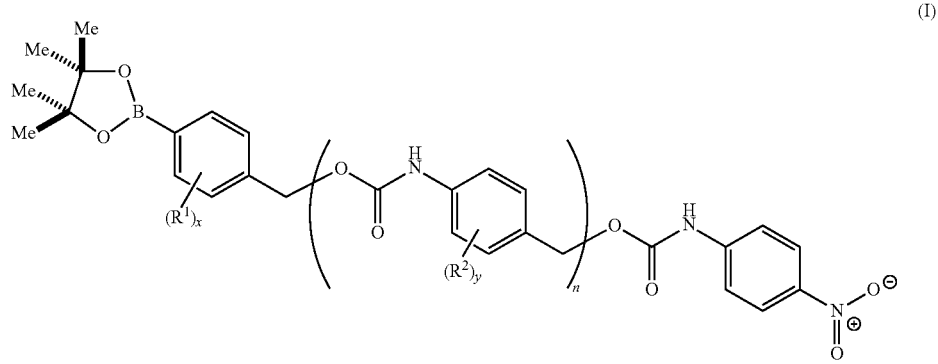

(I)

wherein $R^1$ and $R^2$ are each independently, at each occurrence, selected from the group consisting of hydrogen, $C_1$-$C_6$-alkyl, and $C_1$-$C_6$-alkoxy; x and y are each an integer independently selected from 0, 1, 2, 3, and 4; and n is an integer selected from 0 to 20.

The hydrophobic detection reagent can be a compound of formula (I-a),

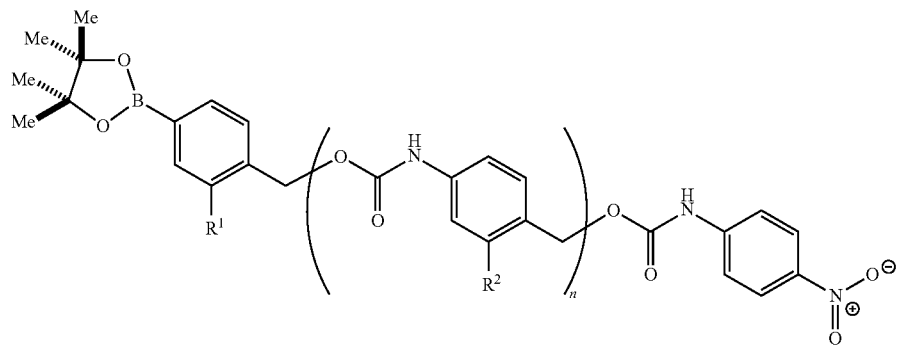

(I-a)

wherein $R^1$ and $R^2$ are each independently, at each occurrence, selected from the group consisting of hydrogen, $C_1$-$C_6$-alkyl, and $C_1$-$C_6$-alkoxy; and n is an integer selected from 0 to 20.

$R^1$ and $R^2$ can each be $C_1$-$C_6$-alkoxy. $R^1$ and $R^2$ can each be methoxy. n can be an integer selected from 0 to 20. n can be 0, 1, 2, 5, 8, 10, 12, 15, 18 or 20.

The hydrophobic detection reagent can be a compound having formula (I-b),

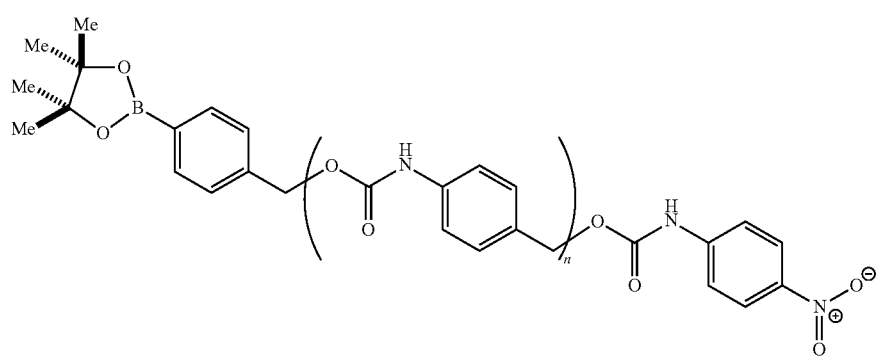

(I-b)

wherein n is an integer selected from 0 to 20. n can be 0.

An assay region of the device can include one or more responsive agents to detect a target enzyme. An assay region can be derivatized with glucose 6-phosphate, lactose, or a combination thereof.

The device can include an immobilized enzyme. The immobilized enzyme can be selected from glucose oxidase, catalase, or a combination thereof.

The device can be configured to detect a target enzyme selected from proteases, glycosidases, esterases, and phosphatases, alkaline phosphatase, β-D-galactosidase, or a combination thereof.

The device may be configured to detect heavy metals, such as mercury and lead. The detection of heavy metals may be performed by the use of aptamers. The aptamers may be immobilized with an enzyme and a nucleic acid.

The device can include a first lateral flow channel leading to a first vertical flow column containing a plurality of treated layers; and a second lateral flow channel leading to a second vertical flow column containing a plurality of treated layers. The second vertical flow column can be configured to correct for internal and/or external factors that affect the wicking rate of the sample within the device, except for the effect of the target analyte on the wicking rate.

The device can include a layer containing a dye for visualization of the sample in a visualization layer.

The concentration of an analyte in a sample can be determined by measuring the time for the sample to flow through the device after addition of the sample. The concentration of an analyte in the sample can be determined by measuring the difference in time between an assay channel and a control channel within the device. The concentration of an analyte in the sample can be determined by counting the number of channels in the device where a color change has occurred within a fixed period of time.

In another aspect, disclosed is a hydrophobic detection agent, having formula (I),

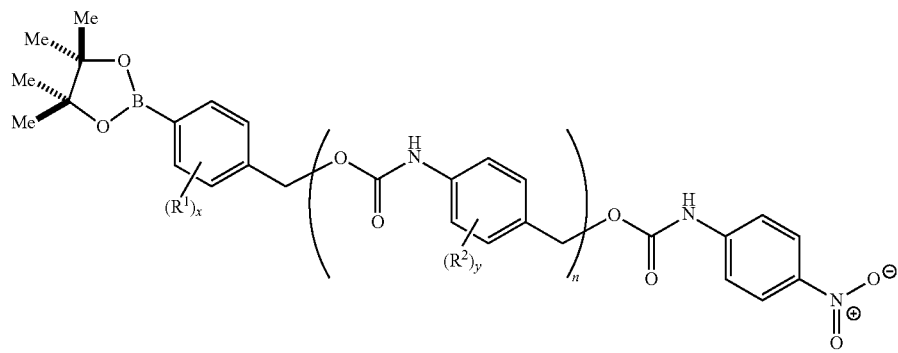

(I)

wherein $R^1$ and $R^2$ are each independently, at each occurrence, selected from the group consisting of hydrogen, $C_1$-$C_6$-alkyl, and $C_1$-$C_6$-alkoxy; x and y are each an integer independently selected from 0, 1, 2, 3, and 4; and n is an integer selected from 0 to 20.

The hydrophobic detection agent can have formula (I-a),

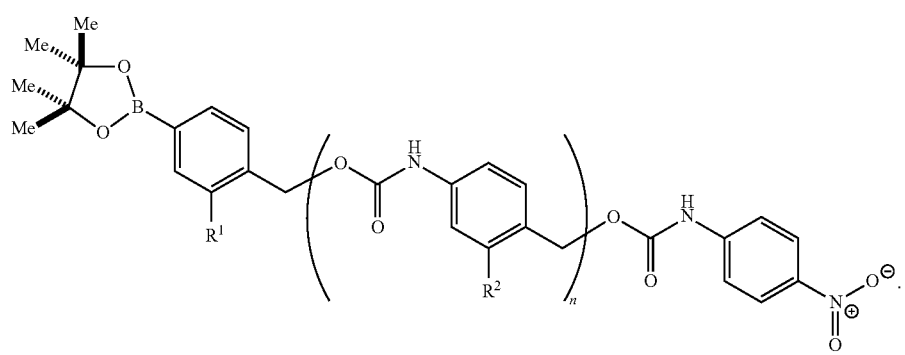

(I-a)

$R^1$ and $R^2$ can each be $C_1$-$C_6$-alkoxy. $R^1$ and $R^2$ can each be methoxy. n can be an integer selected from 0 to 20. n can be 0, 1, 2, 5, 8, 10, 12, 15, 18 or 20.

The hydrophobic detection agent can have formula (I-b),

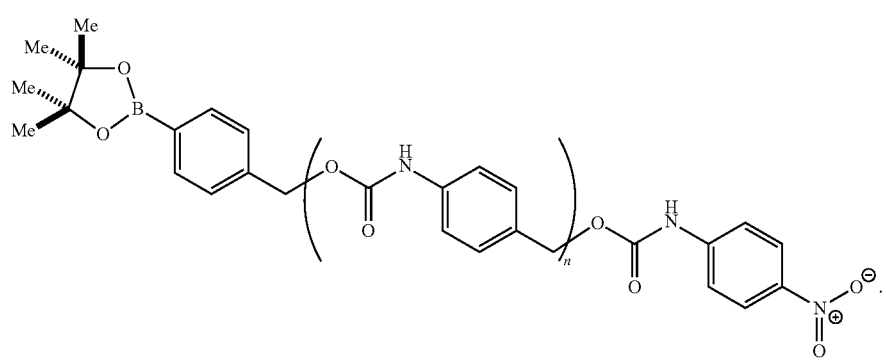

(I-b)

n can be 0 in formula (I-b).

The compounds, compositions, devices, methods, and processes are further described herein.

DETAILED DESCRIPTION

Disclosed herein are "equipment-free" flow-through assay devices based on patterned porous media, methods of making same, and methods of using same. The assay devices can be capillary-driven devices that include a hydrophobic detection reagent in a porous media. The hydrophobic reagent changes to hydrophilic by the presence of a target analyte.

Porous, hydrophilic media can be patterned with hydrophobic barriers for performing assays on liquids. One example of a useful hydrophilic medium for assays is paper, which is inexpensive, disposable, wicks liquids rapidly, and does not require special handling procedures. The paper or other porous, hydrophilic medium can be patterned with hydrophobic barriers that provide spatially defined regions for fluid transport based on capillary action. These hydrophobic barriers, such as wax, can provide an impermeable barrier throughout the entire thickness of the porous, hydrophilic medium within defined areas. The regions defined by the hydrophobic barriers contain the hydrophilic, porous medium, rather than being empty as is common in glass or polymeric (PDMS) microfluidic devices.

Detection Reagents

Figure 1:
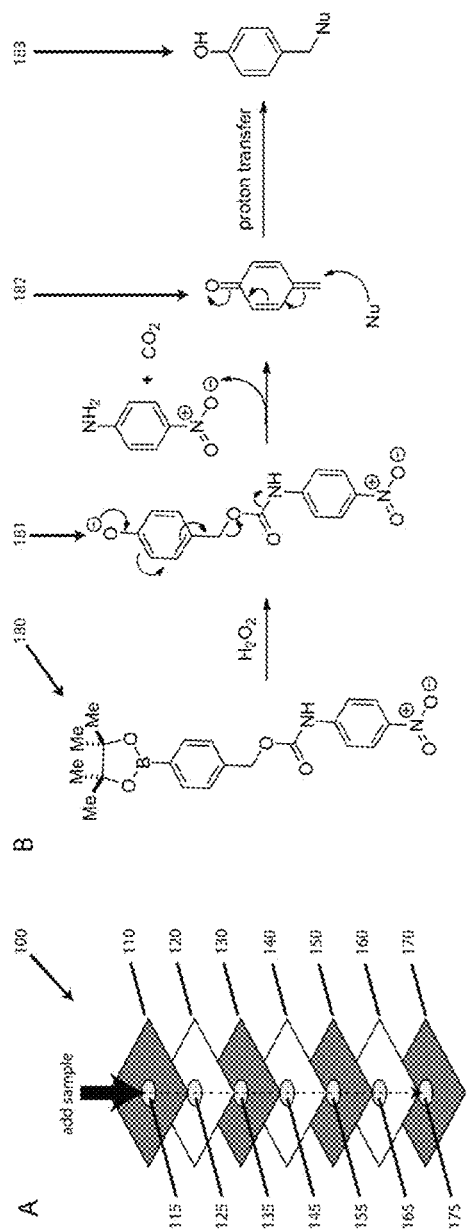
FIG. 1A illustrates a layout of a vertical flow-through assay device.
FIG. 1B illustrates a detection reagent, along with the mechanism for conversion from hydrophobic to hydrophilic molecules.
FIG. 1C illustrates the results of a quantitative determination of the presence of hydrogen peroxide in a sample. Three different quantities of the detection reagent were used to generate the three curves shown.
FIG. 1D illustrates changes in sensitivity by altering the quantity of detection reagent within a vertical flow-through assay device.
Figure 1:
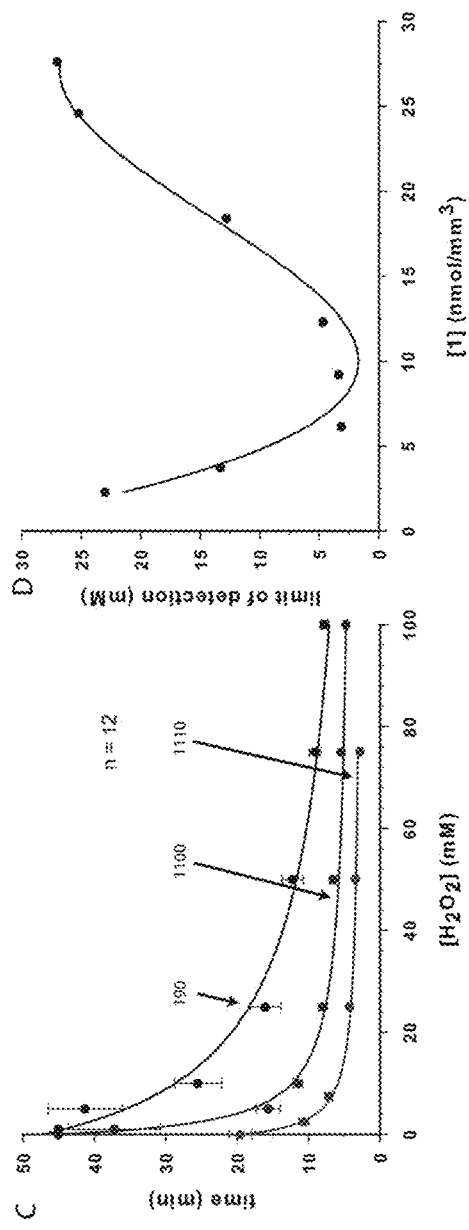
Figure 2:
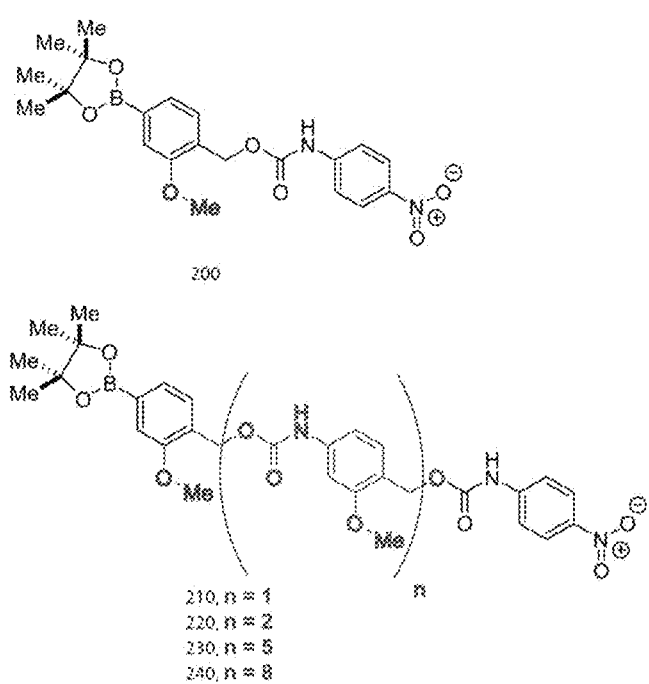
FIG. 2 illustrates variations to the initial detection reagent that can be used to change the sensitivity of an assay.

The hydrophobic detection reagent can be a responsive hydrophobic oligomer. The detection reagent can be a responsive small molecule, oligomer or polymer, including, but not limited to, polyethers, poly(phthalaldehyde), polyvinyl carbamates, and other polycarbamates (e.g., polybenzyl carbamates). One example is an aryl boronate (referred to as the "end-cap") protected oligomeric polycarbamate that is hydrophobic. FIG. 1B shows the structure 180 of a hydrophobic detection reagent and the conversion to hydrophilic byproducts in response to hydrogen peroxide (the target analyte). The aryl boronate "end-cap" is oxidatively cleaved in the presence of hydrogen peroxide to reveal a phenol. Through a quinone methide elimination, an electron cascade occurs along the oligomer backbone to generate hydrophilic small molecule byproducts. In some embodiments, the sensitivity of the detection reagent within the device is modified by increasing the rate of depolymerization through the inclusion of a methyl ether, 200, within each repeating unit (FIG. 2). The methyl ether destabilizes the benzylic C—O bond, increasing the rate of quinone- and azaquinone methide elimination. In some embodiments, the sensitivity is improved by creating a larger change from hydrophobic to hydrophilic in response to a single detection event (Table 1). Longer oligomers will be more hydrophobic (210-240), yet produce the same byproducts, thereby amplifying the response of the detection reagent for a single detection event. The electronics of the detection reagent can be modified (i.e., naphthalene-based repeating units, additional methyl ethers or other electron donating groups, addition of alkyl chains to affect solubility, etc.) to tailor the sensitivity of the device. Other detection reagents that change from hydrophobic to hydrophilic or hydrophilic to hydrophobic can be used in the context of the device, such as responsive polymers (e.g., poly(phthalaldehyde)). The responsive "end-cap" used can include, but are not limited to, aryl boronate, TBS, FMoc, and Alloc protecting groups in order to provide selectivity for target analytes.

Responsive Reagents

In some embodiments, to perform an assay, an assay region of the hydrophilic medium can be derivatized with responsive reagents such as (but not limited to) small molecules, signal transduction molecules, substrates, aptamers, antibodies, or proteins, that interact with the target analyte. For example to detect hydrogen peroxide, an assay region of the hydrophilic medium can be derivatized with a hydrophobic small molecule detection reagent that selectively reacts with hydrogen peroxide. The presence of the hydrophobic detection reagent modifies the wetting properties of the assay region, converting the hydrophilic, porous medium to hydrophobic. When the hydrophobic detection reagent reacts with hydrogen peroxide, it converts to hydrophilic byproducts, switching the wetting properties of the assay region to hydrophilic. In another example, a plurality of assay regions, derivatized with different responsive reagents, can be used in order to detect a target enzyme, such as alkaline phosphatase. In the first assay region encountered by the sample, the assay region is derivatized with a substrate, such as glucose 6-phosphate, that selectively reacts with the target enzyme to produce glucose. Following the production of glucose, the sample can encounter an assay region containing an immobilized enzyme (immobilized on a bead or on the paper itself), such as glucose oxidase, that generates hydrogen peroxide from the glucose within the sample. The hydrogen peroxide is detected with an assay region derivatized with a hydrophobic small molecule detection reagent that selectively reacts with hydrogen peroxide. The presence of the hydrophobic detection reagent modifies the wetting properties of the assay region, converting the hydrophilic, porous medium to hydrophobic. When the hydrophobic detection reagent reacts with hydrogen peroxide, it converts to hydrophilic byproducts, switching the wetting properties of the assay region to hydrophilic. In general a wide variety of reagents can be used in assay devices (i) to detect analytes, (ii) to modify the pH of the sample solution, (iii) to modify the wetting properties of the hydrophilic, porous medium, (iv) to generate additional reagents necessary for the assay to be performed, or (v) to interact with other responsive reagents in order to initiate a signal transduction pathway (e.g., a thiol interacting with a disulfide within another responsive reagent). These reagents can include, but are not limited to, antibodies, aptamers, responsive polymers, proteins, salts, or organic small molecules. These reagents could be adsorbed to the porous, hydrophilic medium non-covalently (through non-specific interactions) or covalently.

Device Assembly

In some embodiments, the vertical flow-through assay device includes multiple alternating layers of a porous, hydrophilic medium that is patterned with hydrophobic barriers and protective coatings (or insulating material) that hold the layers of the device in contact, such as double sided tape, adhesive, or laminate. The fluid flows vertically from one layer to another, constrained by the patterned hydrophobic barriers. A plurality of the defined areas of porous, hydrophilic medium can be treated prior to assembly of the device to provide an assay for a target analyte. Some embodiments may include both lateral and vertical flow-through of the liquid.

Fixed Sample Volume

To obtain a quantitative measurement of an analyte in a sample, a fixed volume of liquid can be deposited in the device. In some embodiments, a defined volume of fluid (or a volume approximately close to the defined volume) can be obtained through patterning the hydrophilic, porous medium using hydrophobic barriers. The hydrophobic barriers generate microchannels, sample wells, or regions that accept a fixed volume of liquid.

TABLE 1

Effect of oligomer length and electronics on limit of detection for quantifying hydrogen peroxide within a sample.

| Compound | Number of Repeating Units | Limit of Detection (µM) |
|---|---|---|
| 180 | 0 | 3125.4 |
| 200 | 0 | 168.5 |
| 210 | 1 | 24.8 |
| 220 | 2 | 11.8 |
| 230 | 5 | 3.7 |
| 240 | 8 | 3.2 |

Spotting Reagents

In some embodiments, reagents can be spotted using capillary tubes and pipets. Ink jet printing and pins, such as used in microarrays, can be used to deposit reagents for mass-production. The reagents can be spotted using organic and/or aqueous solutions. The spotted reagents can be allowed to air dry at room temperature for at least 30 minutes before using the device. The reagents can be dried under vacuum as well.

Flow-Through Device

In some embodiments, the device, 100, is a hydrophilic column made up of a plurality (e.g., 3 to 6 layers) of layers of patterned hydrophilic, porous media with a central, circular defined region (FIG. 1A). A plurality of layers contain regions that are treated with reagents for an assay prior to assembly of the device. The sample (e.g., an aqueous sample, or other type of fluid-containing sample) is added to the top layer, 110, of the device, at the sample inlet region, 115; when the sample is added the assay time is started. The sample wicks vertically, due to capillary action, to the next layer, 120. The second layer, 125, is treated with buffer salts (HEPES) to control the pH of the assay solution. The sample then wicks vertically to contact a plurality (e.g., 1 to 4 layers) of layers, 130-150, containing a region treated with the detection reagent, 135-155. The region treated with the detection reagent alters the porous media to inhibit the flow of liquid through the layer (become hydrophobic) when hydrogen peroxide is not present within the sample. When hydrogen peroxide is present, the detection reagent converts to hydrophilic byproducts, switching the porous media from hydrophobic to hydrophilic (FIG. 1B). The rate that the sample is able to convert the detection reagent to hydrophilic depends on the concentration of hydrogen peroxide in the sample, thereby correlating the time for the sample to wick through the plurality of layers treated with the detection reagent to the concentration of hydrogen peroxide. The sample then encounters a layer, 160, that has been treated with a dye, to allow the sample to be visualized, 165. The colored sample wicks to the bottom layer (170), the visualization layer, causing the visualization layer to change color, 175. The change in color of the visualization layer stops the assay time. The time from addition of the sample to the change in color of the visualization layer is the assay time, and will correlate to the concentration of hydrogen peroxide within the sample (FIG. 1C). The number of layers within the device affects the volume of sample required for the assay to perform optimally, however the assay requires very small volumes of sample for all instances (e.g., 8 to 12 µL). Changes of the quantity of detection reagent, 180, affect the sensitivity of the assay (FIG. 1D) and can be altered to tune the sensitivity to the desired levels for the assay.

Enzyme Assay

Figure 3:
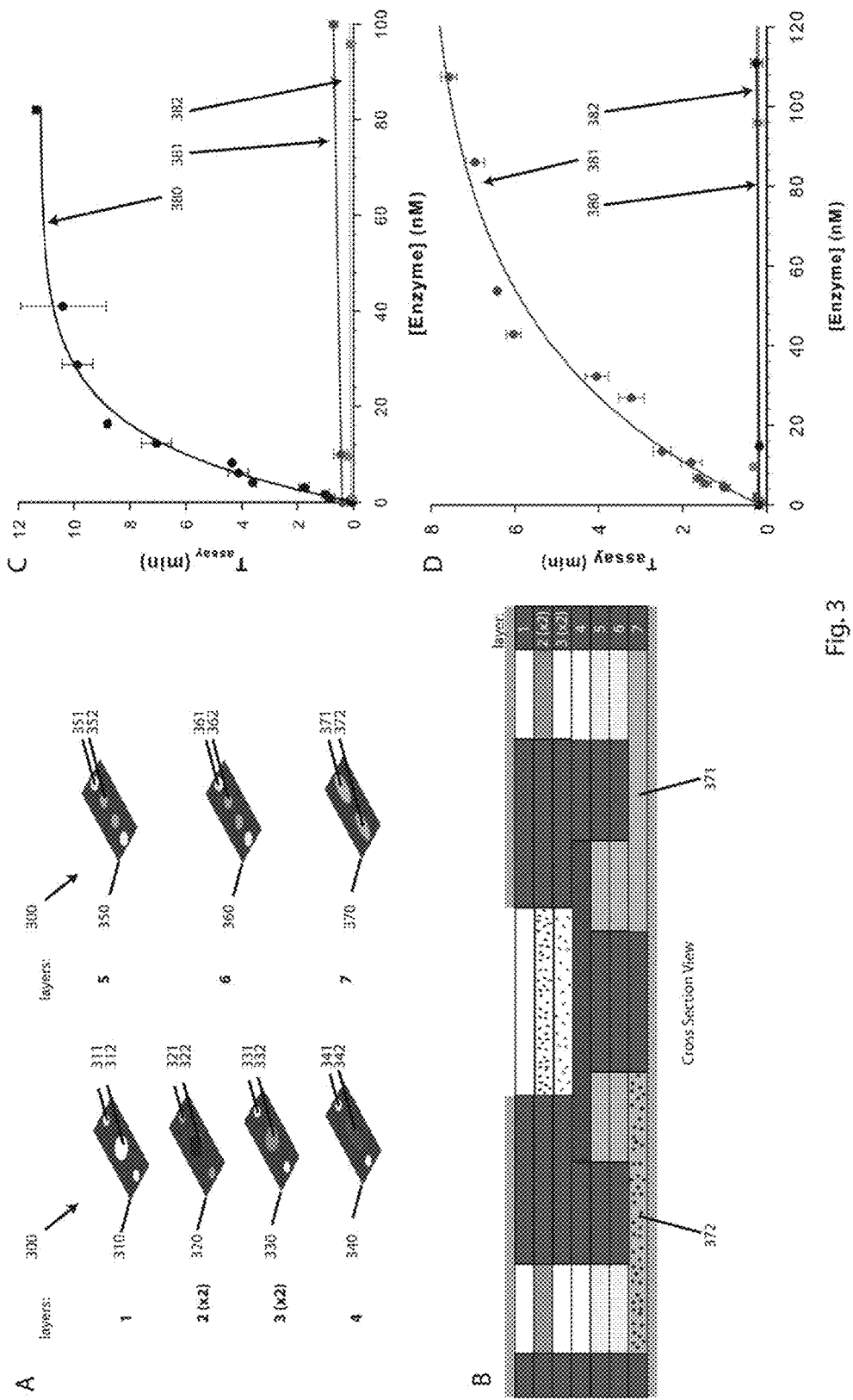
FIGS. 3A and 3B are perspective views of flow-through assay devices.
FIGS. 3C and 3D illustrate the results of a quantitative determination of alkaline phosphatase (FIG. 3C) or β-D-galactosidase in a sample. The selectivity of the assays performed is evident by the lack of a response when enzymes other than the target were tested.

In some embodiments, the device (300) contains a central column of hydrophilic, porous media that splits the sample into two lateral flow channels leading to two separate vertical flow columns containing a plurality of treated layers where an assay is performed (FIGS. 3A and 3B). The device is made from hydrophilic, porous media (e.g., paper) patterned with hydrophobic barriers and layers of adhesive material (e.g., spray adhesive) stacked in alternating order. Protective coatings (e.g., laminate) are used to seal the top and bottom of the device (together), with an aperture in the top layer of the protective coating to allow for sample addition. The sample (e.g., 30 to 120 µL) is added to the sample addition aperture (312), contacting the top layer of patterned paper, 310. The sample then wicks vertically through a plurality of layers (e.g., 2 to 6 layers), 322 and 332, before splitting into two sides (the "assay" side and the "control" side) via a horizontal lateral flow channel, 342, that contains buffer salts (e.g., HEPES). The sample wicks down vertically in both sides (352), encountering a substrate (e.g., glucose 6-phosphate) for the target analyte (e.g., alkaline phosphatase) in a plurality of layers (e.g., 1 to 4 layers), 350 and 360. When alkaline phosphatase (the target analyte) is present within the sample, the glucose 6-phosphate (the substrate) is converted to glucose. In both sides, the sample then reaches a lateral flow region containing additional substrate, 370. In the "assay" side of the device only (372), this lateral flow region also contains an immobilized enzyme (e.g., glucose oxidase immobilized on ~10 µm polystyrene particles). The immobilized glucose oxidase will convert the glucose generated by the target enzyme into hydrogen peroxide. The size of the polystyrene particles prevents the glucose oxidase from travelling with the solvent of the sample, minimizing the amount of protein present within the sample (high levels of protein will affect the viscosity and wicking rate of a liquid). The sample then wicks up vertically through identical columns of patterned paper on both sides. The sample encounters a plurality (e.g., 1 to 4 layers) of layers, 361 and 351, containing detection reagent that will respond to the presence of hydrogen peroxide. Following the detection reagent layer(s), the sample redissolves a dye (321) and then wicks to the top layer into the visualization regions, 311. The assay time is started when the visualization region of the "assay" side changes color, and ends when the visualization region of the "control" side changes color. The measured assay time will correlate to the initial concentration of alkaline phosphatase within the added sample. The comparison of flow-through time between the "assay" side and the "control" side directly measures the generation of hydrogen peroxide from the presence of the alkaline phosphatase, 380 (FIG. 3C). The responsive substrate used within the device (352, 362, 371, and 372) provides the selectivity for this type of assay. Changing the substrate allows for selective detection of different analytes (e.g., β-D-Galactosidase, 381) without showing a response to other enzymes (e.g., catalase, 382). Due to the lack of glucose oxidase, the "control" side should not generate any hydrogen peroxide, even when alkaline phosphatase is present. The "control" side, 371, serves to correct for any internal (i.e., viscosity, or background hydrogen peroxide) or external factors (i.e., temperature, or humidity) that may affect the wicking rate of the sample within the device.

Preprocessing

Figure 4:
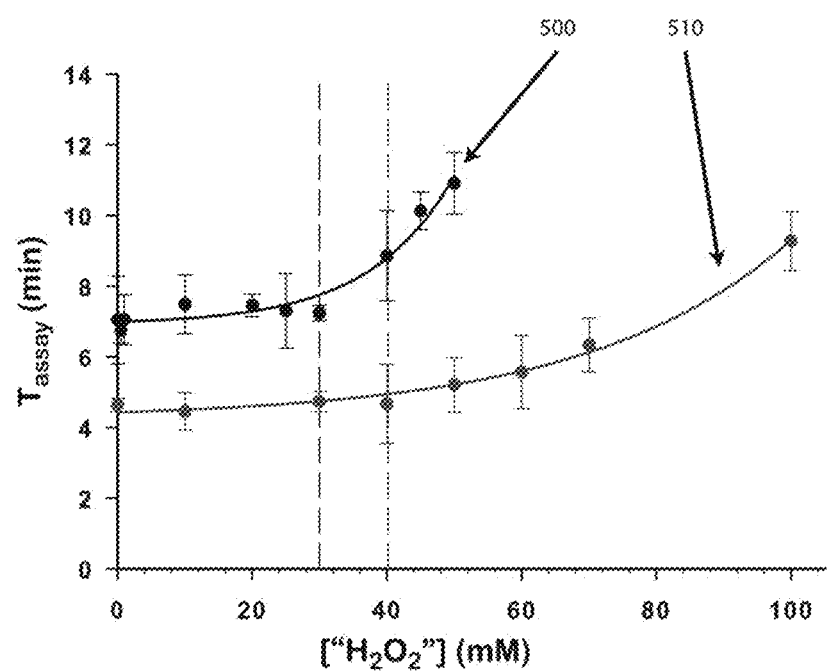
FIG. 4 illustrates the removal of glucose and hydrogen peroxide from a sample, containing the target enzyme, through the addition of preprocessing layers.

In some embodiments, the device contains layers to remove impurities from the sample that may affect the assay results. The impurities removed may be physical (e.g., dirt) or chemical (e.g., glucose or hydrogen peroxide). The porous media used in the device can be used to filter particles from the sample. In some embodiments, the porous medium used can be selected to filter the sample and remove physical impurities, such as red blood cells. The pore size of the porous media used will determine the particle size that can be removed from the sample. Treatment of the hydrophilic, porous media can bind, or otherwise remove small chemical impurities that cannot be removed based on size. In certain embodiments, the device contains a layer(s) treated with immobilized glucose oxidase (322), followed by a subsequent layer(s) treated with immobilized catalase (332). Glucose that is present within the sample will be converted to hydrogen peroxide in the layer containing glucose oxidase, the generate hydrogen peroxide will then be decomposed by the catalase, eliminating glucose, 510, present within the sample (FIG. 4). This same setup allows for the removal of background hydrogen peroxide, 500, within the sample as well. Enzymes can be immobilized either through chemical modification of the porous media, or through coupling (e.g., biotin-streptavidin) with large particles (e.g., ~10 µm polystyrene particles). The pore size of the hydrophilic, porous media prevents the movement of the immobilized enzymes between layers.

Dial Design

Figure 5:
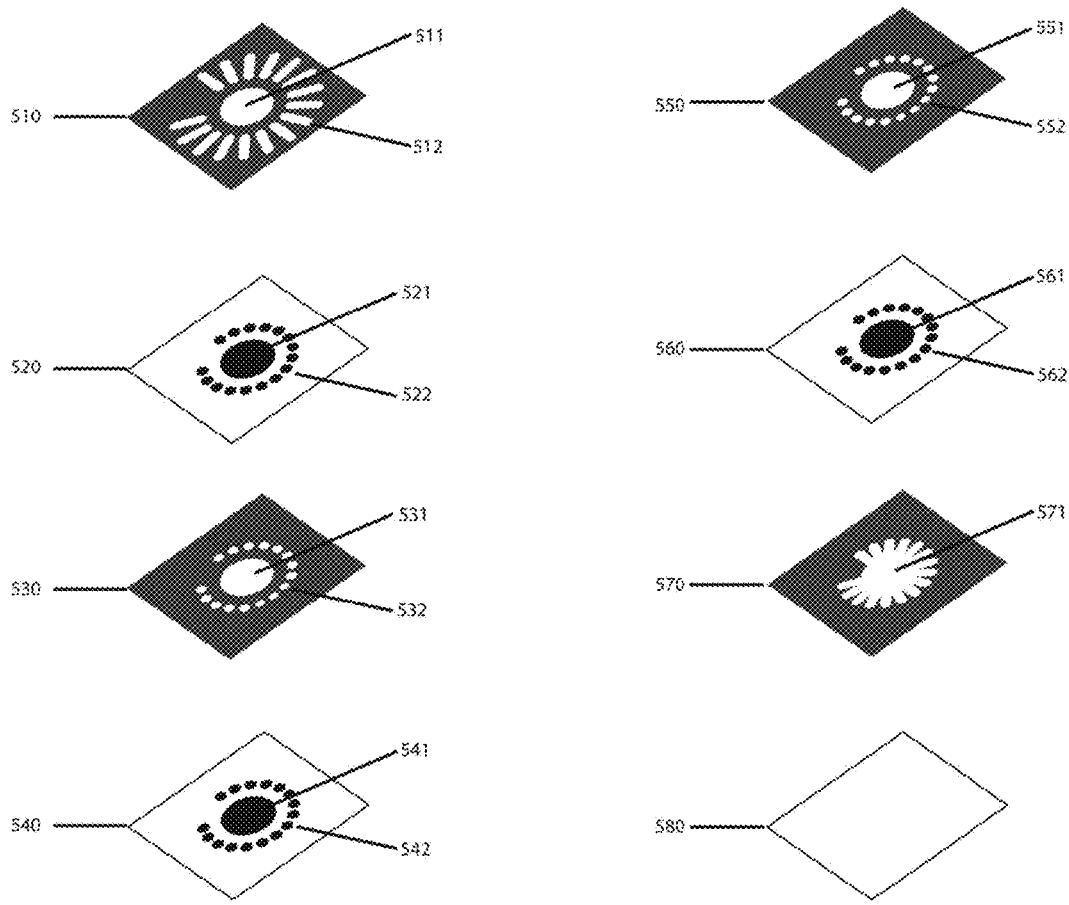
FIG. 5A illustrates the layout of a vertical flow-through device.
FIG. 5B illustrates the results of a quantitative determination of hydrogen peroxide in a sample.
Figure 5:
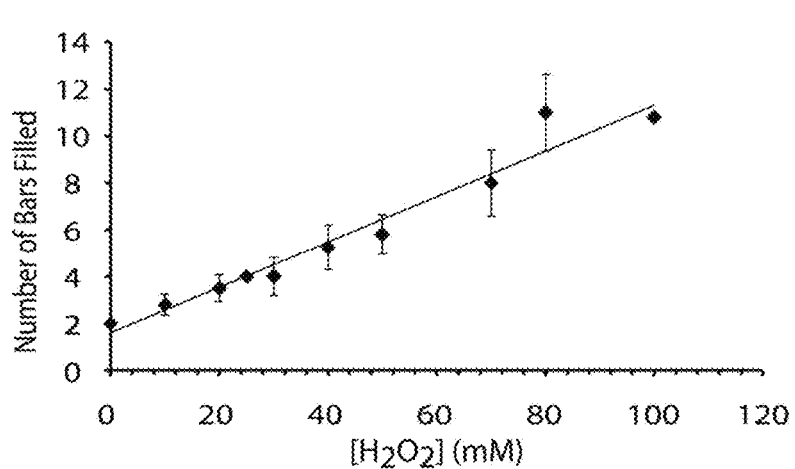

In some embodiments, the device functions using a fixed assay time (e.g., 5, 10, 15, or 20 minutes), rather than measuring concentration by the final assay time. One example of the device, 500, contains a central sample addition column, surrounded by a circular array (e.g., 2 to 25 columns) of equally spaced assay columns. The sample is added to the top layer, 510, of the device, in the sample addition region (511), and then wicks down vertically through a plurality (e.g., 4 to 8 layers) of layers, 520-560. The bottom layer, 570, of the device laterally distributes, 571, the sample evenly to each of the surrounding assay columns. The sample then wicks up vertically into each column simultaneously, 562-512. In each column, the sample encounters a layer, 562, treated with buffer salts (e.g., HEPES) before contacting a plurality (e.g., 1 to 4 layers) of layers, 552 and 532, treated with the hydrophobic detection reagent. The presence of the analyte (e.g., hydrogen peroxide) converts the hydrophobic detection reagent to hydrophilic byproducts. In a clockwise manner, each subsequent assay column has an increasing quantity of the hydrophobic detection reagent initially included, starting at the top of the device (12 o'clock position). The sample then wicks through a layer, 522, treated with a dye before reaching the top layer, containing visualization regions, 512, for each column. Within a fixed period of time, the concentration of hydrogen peroxide initially within the sample will only convert a certain quantity of the hydrophobic detection reagent to hydrophilic. The assay columns containing less than or equal to this quantity of hydrophobic detection reagent will have allowed the sample to reach the visualization layer within the fixed assay time, whereas the columns containing more detection reagent than this will not. The concentration of hydrogen peroxide within the sample is measured by counting the number of visualization regions on the top of the device that have changed color at the end of the fixed assay time (FIG. 5B). In one embodiment of the device, the visualization regions are shaped like bars, so the device can be read similar to a dial. Other configurations of the device, including but not limited to, multiple arrays of visualization regions, different shaped arrays of visualization regions, and inclusion of a fluidic timer, can be used in order to tune the sensitivity, selectivity, and ease of use for the device.

Multiplexed Assays

In some embodiments, multiple assays can be performed simultaneously in a single device, using the same aliquot of sample. The single addition of a sample allows the user to perform multiple assays without additional processing, improving the ease of use for the device. One example includes a device where the sample is added to the top layer of the device, in the sample addition region, before wicking to the distribution layer. The distribution layer laterally distributes the sample evenly to two assay device regions. The sample then wicks down vertically into the two assay device regions, which are substantially identical to each other, but with the responsive reagents necessary to detect two distinct analytes (e.g., glucose 6-phosphate for alkaline phosphatase and lactose for β-D-galactosidase, as well as aptamers for the detection of heavy metals). The layout of each of the assay device regions can be similar to 300, or a different configuration, depending the analytes detected, and the method of detection used (e.g., flow-through device, enzyme assay, or dial device).

EXAMPLES

The foregoing may be better understood by reference to the following examples, which are presented for purposes of illustration and are not intended to limit the scope of the invention.

Example 1. Capillary-Driven Device Using Small Molecule Detection Reagents

Figure 6:
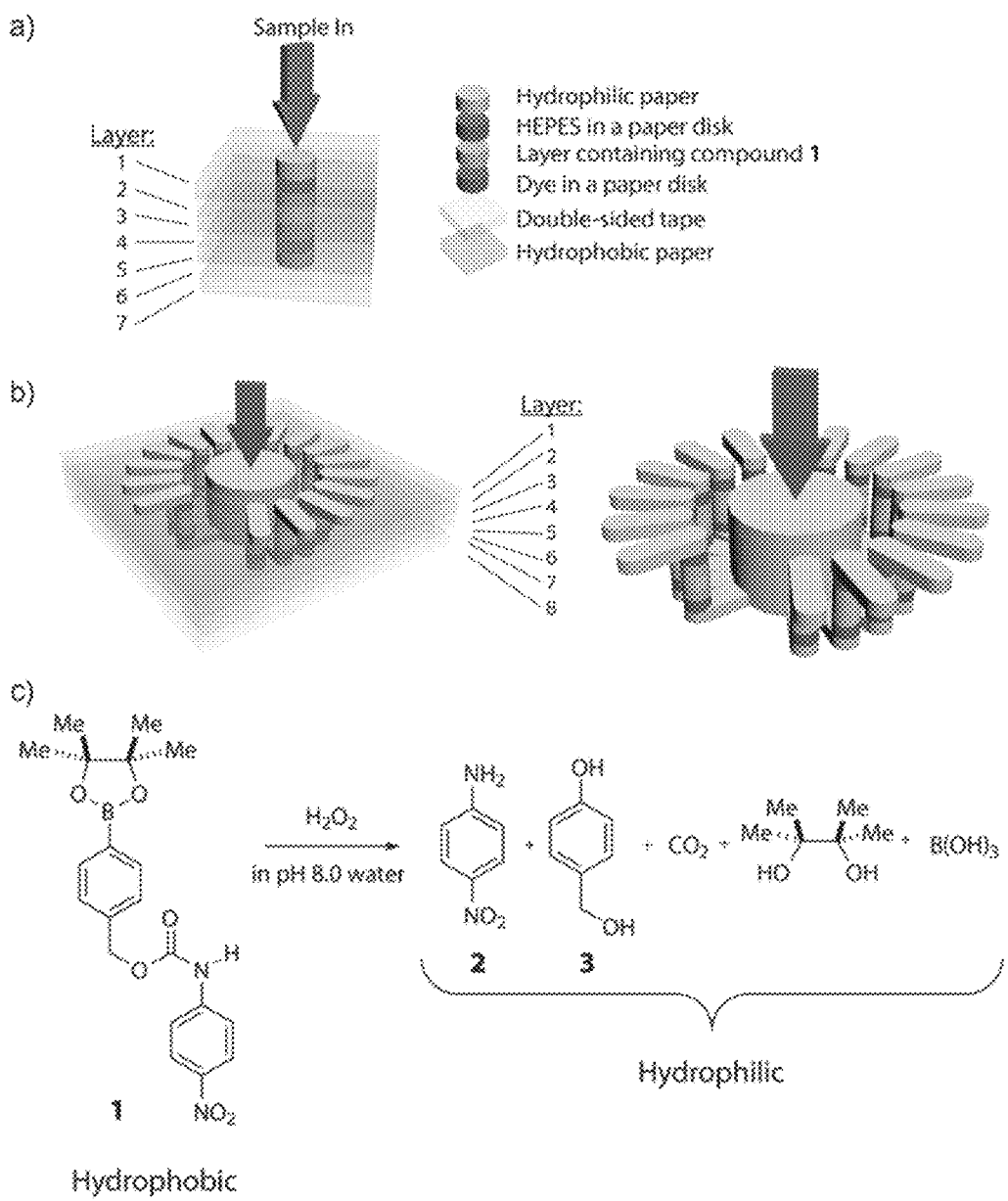
FIG. 6A shows a "digital" assay that uses a single conduit device.
FIG. 6B shows an "analog" assay that uses a radial paper-based microfluidic device.
FIG. 6C shows a detection reagent.

Capillary-driven devices using small molecule detection reagents were constructed and evaluated. FIGS. 6A-6C depict two 3D paper-based microfluidic devices including compound 1 as a detection agent.

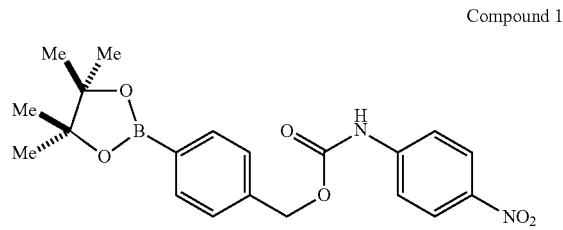

Compound 1

Both of the assays are based on selective changes in the wetting properties of paper, since hydrogen peroxide (a model analyte) oxidatively cleaves compound 1 (the detection reagent; FIG. 6C), which is hydrophobic and is deposited into defined regions of the microfluidic conduits prior to assembling the devices. Reaction of hydrogen peroxide with compound 1 initiates an elimination reaction that converts compound 1 into hydrophilic byproducts such as compounds 2 and 3 (FIG. 6C). This change from hydrophobic to hydrophilic allows the sample to wick through the device and wet a detection region, where the time required to wet the detection region depends on the concentration of the analyte.

Figure 7:
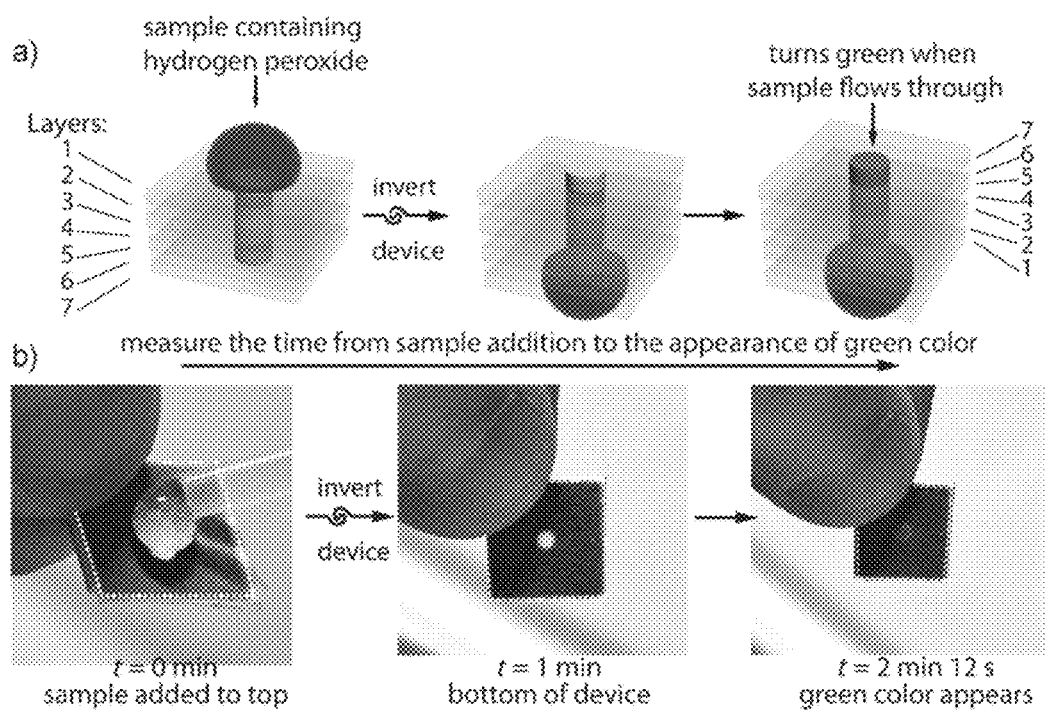
FIG. 7A shows a diagram of an assay procedure for a "digital" device.
FIG. 7B shows photographs over time for a device exposed to an analyte.

FIG. 6A shows a digital assay that uses a single conduit device to report the concentration of hydrogen peroxide by measuring the time required for the sample to flow through the device in the z direction. This 3D paper-based microfluidic device of FIG. 6A (10 mm wide×10 mm long×0.9 mm thick) is formed by stacking alternating layers of wax patterned paper and patterned double-sided adhesive tape to create a device that contains seven layers (four paper layers and three tape layers) and a single hydrophilic conduit that extends in the z direction from one end of the device to the other. 2 μL of sample is added to the top of the hydrophilic conduit (layer 1) and a colored readout appears on the bottom of the device (layer 7) when the sample has flowed through the entire device (FIG. 7). Layer 2 is patterned tape that contains a 2.5 mm diameter hole that is filled with a 180 μm thick disk of Whatman Chromatography Paper No. 1. This disk contains 4-(2-hydroxyethyl)-1-piperazineethane-sulfonic acid buffer (HEPES) that was predeposited (0.25 μL from a 45 mM, pH 8.0 solution) and dried on the paper disk prior to assembling the device. The buffer salts are included in the device to ensure that the pH value of the sample is approximately 8.0, which facilitates rapid oxidative cleavage of 1 by hydrogen peroxide. Layer 4 contains a disk of Whatman Chromatography Paper No. 1 in a hole in patterned tape, whereas layers 3 and 5 are patterned Boise Aspen 30 printer paper that each contain compound 1 in a 2.5 mm diameter hydrophilic region (1 is predeposited from ethyl acetate solutions ranging in concentration from 7.5 to 130 mM). Two layers that contain 1 are included, because initial studies showed that two layers provided more reproducible assay results than a single layer of paper containing 1. Layer 6 is patterned tape, but in this case the 2.5 mm diameter, 180 μm thick disk of Whatman Chromatography paper No. 1 contains predeposited (0.25 μL) green food coloring. Layer 7 is the readout region and contains patterned Boise Aspen 30 printer paper with a 2.5 mm diameter white hydrophilic region that becomes bright green after the sample redissolves the dye in layer 6 and distributes it to layer 7.

FIGS. 7A and 7B depict a diagram of the assay procedure for the "digital" device in FIG. 6A exposed to 100 mM hydrogen peroxide. The "digital" device of FIG. 7A-7B may function as follows: sample is added initially to the top of the device, the device is then inverted to allow the detection layer to become visible. After the sample is added to layer 1 (FIG. 7A, left images), it wicks through layers 1 and 2, buffering the sample solution with the redissolved HEPES. Once the sample reaches layer 3, hydrogen peroxide in the sample reacts with 1 to yield hydrophilic products (FIG. 7A, middle images). This reaction is repeated in layer 5. The reaction with hydrogen peroxide changes the wetting properties of the paper to allow the sample to continue wicking through the device to layer 6, where it redissolves the green food coloring from the paper disk. This food coloring is then wicked into layer 7 where the colored solution becomes visible (FIG. 7A, right images).

Figure 8:
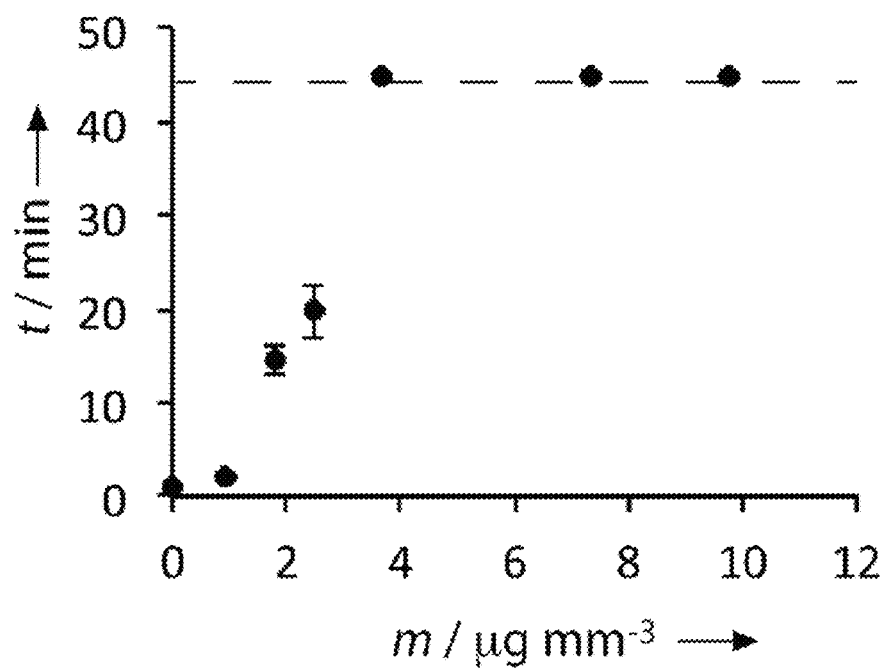
FIG. 8 shows the effect of the quantity of 180 per volume of paper (m) on the flow-through time of water through a "digital" device.

The addition of pure water to this type of "digital" device demonstrates the effect that compound 1 has on the wetting properties of paper (FIG. 8, the error bars reflect the standard deviations from the average values) of the device in FIG. 6A. The average flow-through time for each experiment in FIG. 8 was determined by using at least five replicate measurements at 20° C. and 25% relative humidity. Separate experiments were conducted using different amounts of compound 1; from these experiments it was found that the presence of only 3.6 μg mm$^{-3}$ of compound 1 in layers 3 and 5 is needed to prevent water from flowing through the vertical hydrophilic conduit in (e.g., as shown in FIG. 1A or FIG. 6A) within the allotted assay time of 45 min.

Figure 9:
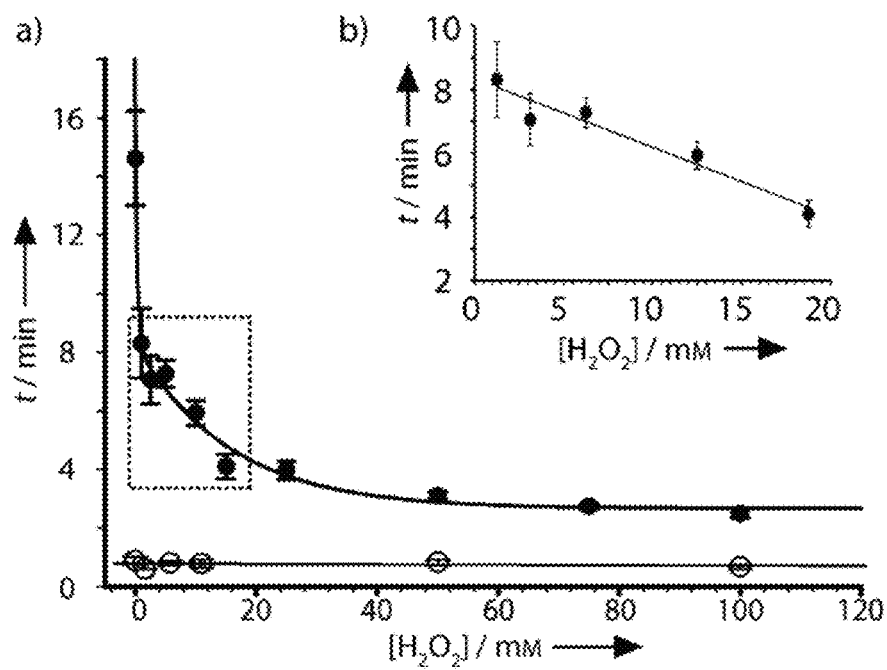
FIGS. 9A and 9B show the effect of analyte concentration on flow-through time.

When hydrogen peroxide is included in the sample, however, the flow-through time is correlated with the concentration of hydrogen peroxide in the sample (FIG. 9A, closed circles). Specifically, devices were assembled as shown in FIG. 6A; layers 3 and 5 each contained 1.7 μg mm$^{-3}$ of compound 1. The open circles represent flow-through times when 0 μg mm$^{-3}$ of compound 1 is included in the device. The average flow-through time for each concentration of hydrogen peroxide was determined using ten replicate measurements at 20° C. and 25% relative humidity. FIG. 9B shows an expanded view of the dotted region in 9A. This graph was used to determine the limit of detection for the assay. The error bars reflect the standard deviations from the average values. The measured flow-through times were recorded when the entire hydrophilic region of layer 7 turned green, which required between less than 1 second and 10 seconds from the initial appearance of green. Low concentrations of hydrogen peroxide had the slowest flow-through times and the greatest delay in filling layer 7 with the green solution.

The exponential relationship between hydrogen peroxide concentration and flow-through time illustrated in FIG. 9A indicates that the assay is particularly sensitive to low concentrations of hydrogen peroxide: in this assay, the limit of detection is approximately 0.7 mM hydrogen peroxide (FIG. 9B) and the dynamic range is approximately 0.7-100 mM. FIG. 9A also reveals that the detection reagent (e.g., compound 1) is essential for generating the aforementioned relationship between hydrogen peroxide concentration and flow-through time: as can be seen in the absence of the detection reagent (FIG. 9A, open circles), the flow-through times are uniform and rapid across the different concentrations of hydrogen peroxide tested.

Since wicking rates in porous media typically are affected by humidity, the effect of this variable was tested in the flow-through assay. The flow-through time is independent of humidity over the range of 17-62% relative humidity, which is a result that can be attributed to the exceedingly short path length that the sample must travel in the device (ca. 900 µm).

Figure 10:
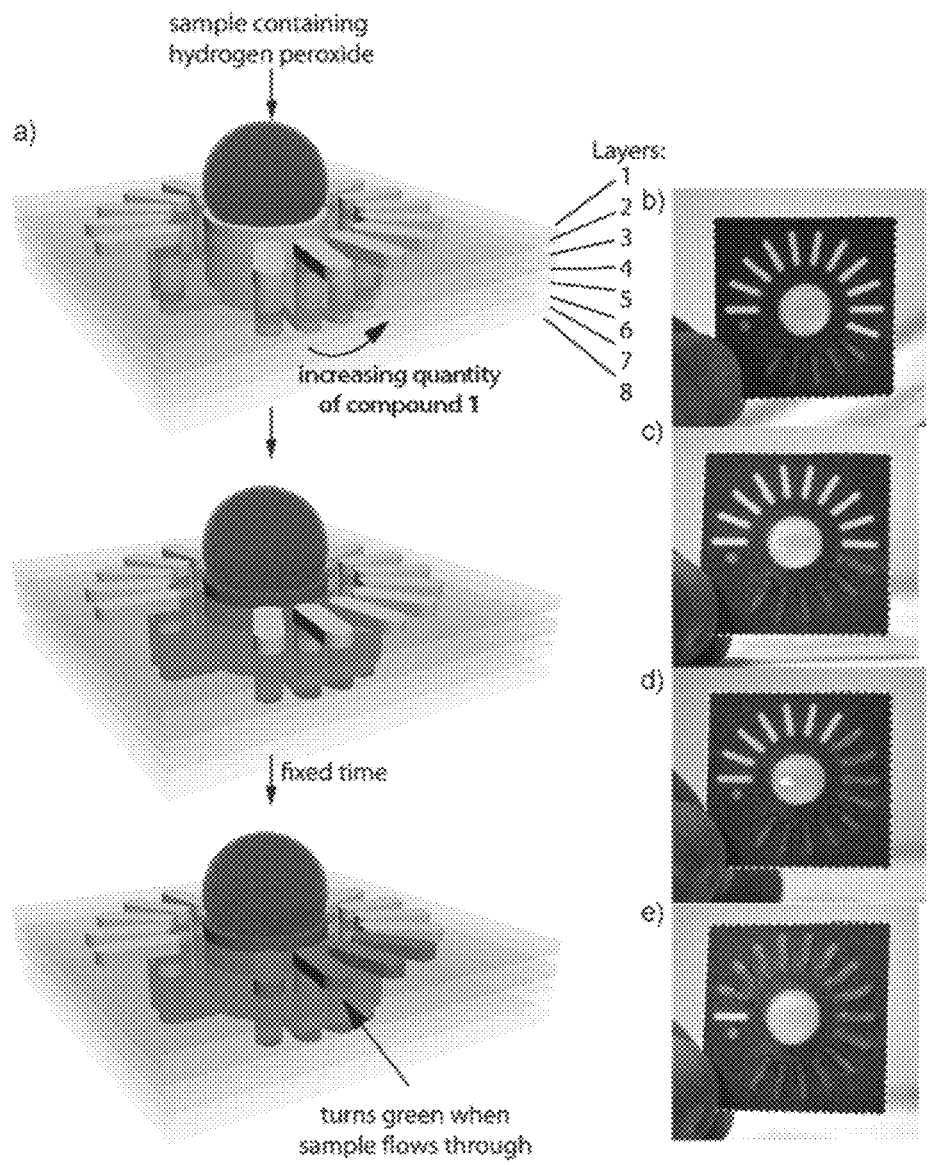
FIGS. 10A-10E show an "analog" device.

FIG. 6B and FIG. 10A show an analog assay that uses a radial paper-based microfluidic device for quantifying the level of hydrogen peroxide by using a fixed assay time and by counting the number of bars that become colored as a function of the concentration of hydrogen peroxide in the sample. This analog design (FIG. 6B) requires that a user count the number of colored bars that appear after a fixed assay time. Sample is initially added to the top of the device, where it wicks down through the device and is distributed to the surrounding conduits. These surrounding conduits have nearly the same configuration as the device in FIG. 6A, with the exception that the quantity of the detection agent (e.g., compound 1) increases by 1.1 µg mm$^{-3}$ in each subsequent conduit along the radial configuration. FIGS. 10B-10E depict photographs after a 10 min assay of devices that were exposed to 1 mM (FIG. 10B); 35 mM (FIG. 10C); 75 mM (FIG. 10D); and 100 mM hydrogen peroxide (FIG. 10E). The edges of the devices shown are marked with white dotted lines. Specifically, the design uses an 8-layer 3D paper-based microfluidic device (32 mm wide×32 mm long× 1.0 mm thick) that contains 16 hydrophilic conduits (2.5 mm diameter) arranged in a circle surrounding a central hydrophilic conduit (10 mm diameter). The sample is added to the central conduit in layer 1, which is patterned Whatman Chromatography Paper No. 1, and then wicks through the device in the z direction down to layer 7 (FIG. 10A, top image). In layer 7, the central conduit separates the sample evenly into the 16 surrounding conduits. The surrounding conduits direct the sample up (in the z direction), opposite to the direction of flow in the central conduit. This arrangement allows the sample to be added to the top of the device, and the bars for the dial to be visible on the top as well. Layer 8 is a single-sided protective tape that allows the user to place the device on a surface to run the assay. The outer conduits of this device are composed of the same layers as the conduit in the "digital" device (e.g., a paper disk containing HEPES buffer salts, followed by two layers containing 1, and then a paper disk containing dried green food coloring). However, in this device, each successive conduit contains increasing amounts of compound 1 compared to the previous conduit (FIG. 10A). Because flow-through time increases as the amount of compound 1 in the conduit increases, each conduit has a longer flow-through time than the preceding one. By using a fixed assay time (e.g., 10 min), the number of colored bars (resulting from flow-through) is used to quantify the amount of hydrogen peroxide in a sample. FIGS. 10B-10E show several examples of devices that were exposed to different concentrations of hydrogen peroxide.

Figure 11:
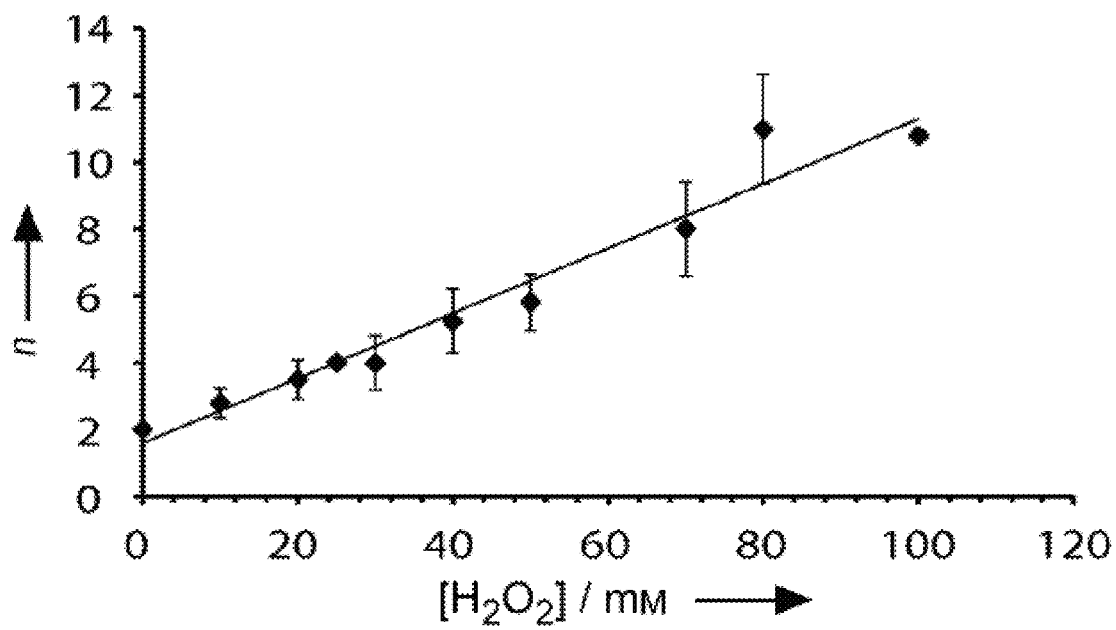
FIG. 11 shows the sensitivity of an "analog" embodiment of the device.

FIG. 11 shows the relationship between the number of bars filled (n) in the "analog" device and the concentration of hydrogen peroxide (0-100 mM) in a sample. The concentration of compound 1 increased by 2.3 µg mm$^{-3}$ increments between conduits in the devices used to obtain this data. The assay may be more sensitive if conduits increase in 2.3 µg mm$^{-3}$ increments rather than 1.1 µg mm$^{-3}$. The average number of bars after a 10 min assay was obtained from five replicate measurements. The error bars reflect the standard deviations from the average values.

While these studies used hydrogen peroxide as a model analyte for demonstrating the use of analog and digital assays in paper microfluidics, other analytes may be used as well.

Example 2. Capillary-Driven Device Using Oligomer Detection Reagents

Capillary-driven devices using oligomer detection reagents 3-6 were constructed and evaluated.

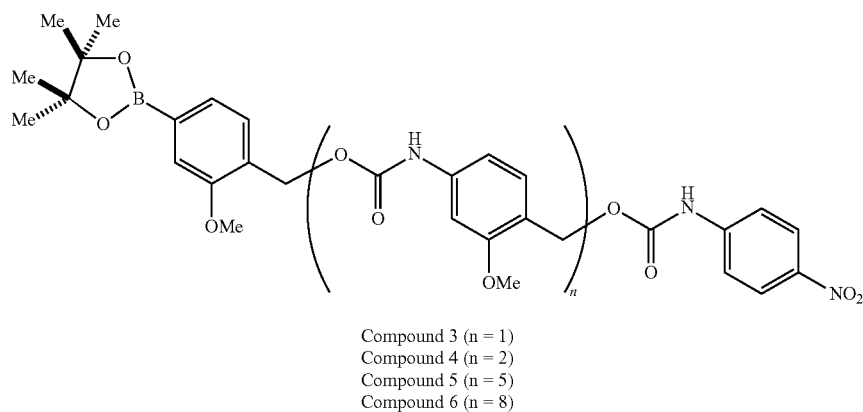

Compound 3 (n = 1)
Compound 4 (n = 2)
Compound 5 (n = 5)
Compound 6 (n = 8)

The carbamate oligomers can depolymerize from head-to-tail as phase-switching reagents and be used for increasing the sensitivity of quantitative point-of-care assays that are based on measurements of time. The carbamate oligomers selectively react with hydrogen peroxide (a model analyte) and provide sensitivity by depolymerizing in the presence of the analyte to convert from water-insoluble polymers to water-soluble products. This switching reaction allows a sample to wick through a three-dimensional paper-based microfluidic device, where the flow-through time reflects the quantity of the analyte in the sample. Oligomers as short as pentamers allow quantitative detection to low nanomolar concentrations of the analyte. This approach improves the sensitivity four orders of magnitude compared to devices of Example 1 (limits-of-detection of hydrogen peroxide of Example 2 are approximately 146 nM). By further optimizing the number of layers of paper containing the oligomer in the assay platform, the limit of detection was improved by approximately another order of magnitude, providing a limit of detection of 31 nM and a ~50,000-fold improvement. The assay devices can be used in resource-limited environments where many analytes of interest are present in samples at (or below) micro- and nanomolar levels.

Figure 12:
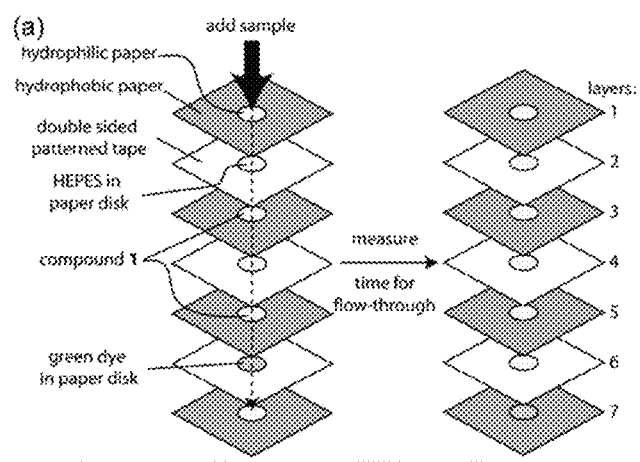
FIG. 12 illustrates the layout of a vertical flow-through assay device.

The devices including oligomeric detection reagents were prepared according to FIG. 12. The assays, like that of Example 1, are conducted in a three-dimensional (3D) paper-based microfluidic device that includes stacked, alternating layers of (i) paper that has been patterned with wax into hydrophobic and hydrophilic regions, and (ii) double-sided adhesive tape, which has holes patterned into it using a CO₂ laser cutter, as shown in FIG. 12. The holes in the tape are filled with disks of hydrophilic paper such that hydrophilic regions in paper connect with the hydrophilic disks in the tape. Each layer of the device (except layers 1, 4, and 7) is pre-loaded with a reagent and dried before assembly, such that addition of sample to the top of this device allows the assay to occur automatically without user intervention. As the sample passes from layer 1 into layer 2, it re-dissolves HEPES buffer salts to control the pH of the sample. In layers 3 and 5, the sample encounters the detection reagent (e.g., an oligomer compound 3, 4, 5, or 6), which is hydrophobic and water-insoluble, thus alters the wetting properties of the paper. In the absence of the analyte, the sample stops wicking (or slowly wicks, depending on the quantity of oligomer detection reagent in the paper) through hydrophobic layers 3 and 5. In the presence of hydrogen peroxide, the oligomer detection reagent (e.g., compound 3, 4, 5, or 6) selectively degrades into hydrophilic products, thus switching phases from insoluble into soluble products, and, consequently, changing the wetting properties of the paper so that it is once again hydrophilic. After this switching reaction occurs, the sample wicks to layer 6 where it re-dissolves dried food coloring to convert the sample into a brightly colored solution, which becomes visible when the sample fills the hydrophilic circular region in layer 7. The quantity of hydrogen peroxide is measured in this device by tracking the time required for the sample to pass from the top of the device to the bottom, which is established by the appearance of green color in layer 7. The selectivity for the assay is provided by the selective oxidative cleavage of the aryl boronate in the oligomer detection reagent via hydrogen peroxide, although presumably other activity-based detection events could be employed if the aryl boronate is replaced with a substrate for another target analyte.

Figure 13:
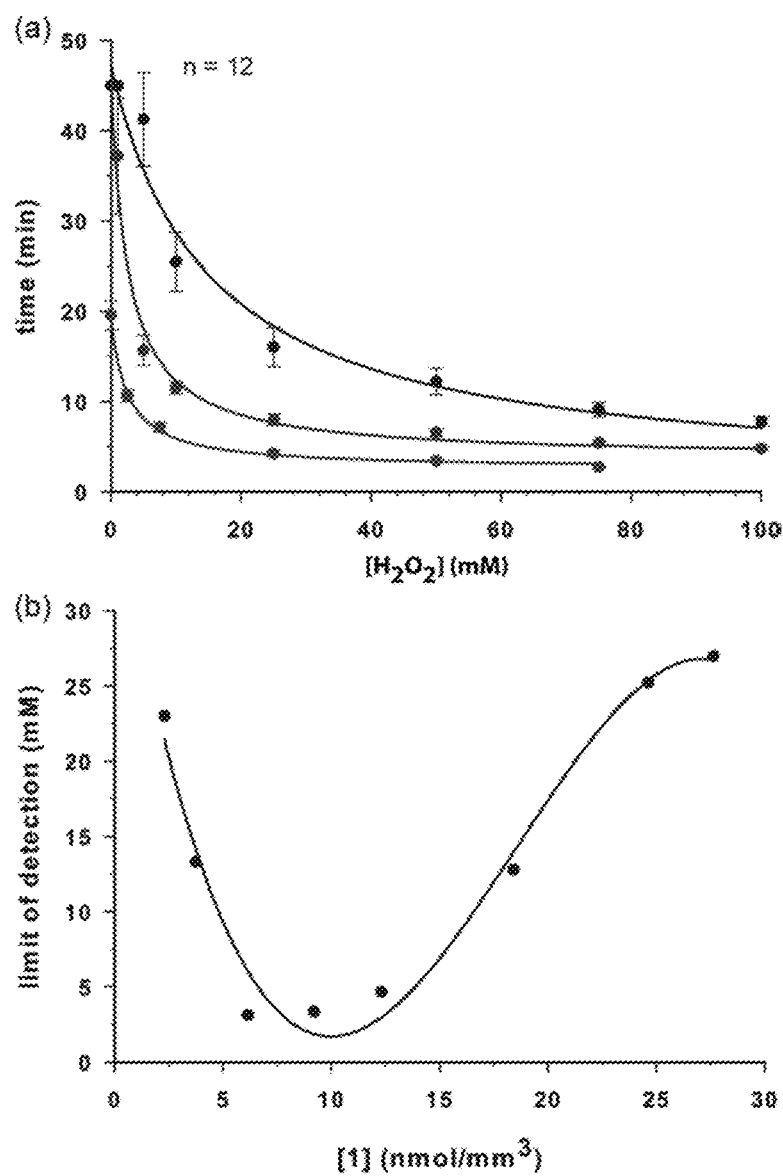
FIGS. 13A and 13B show the relationship between a detection reagent and the time required for a sample containing analyte to flow through a paper-based microfluidic device.
Figure 14:
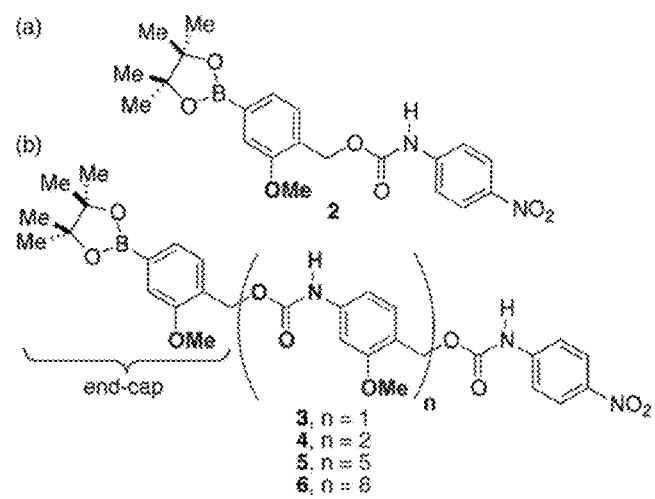
FIG. 14 illustrates increasing the sensitivity of a quantitative assay by modifying the detection reagent.

Design of the oligomers (FIG. 14B) was based on compound 2 (FIG. 14A), which itself was designed based on compound 1 and the reaction kinetics/limit of detection profile of compound 1 (FIGS. 13A and 13B). Specifically, compound 2 was designed to degrade into hydrophilic products faster than compound 1. Addition of a methyl ether ortho to the benzylic leaving group on the benzene ring accelerates the rate of quinone methide elimination reactions, which is the proposed degradation pathway for compounds 1 and 2 to convert to hydrophilic products. Accelerating this quinone methide elimination reaction, it was hypothesized that more of hydrophobic compound 2, compared to compound 1, would convert to hydrophilic products in the time frame that it takes for (i) hydrogen peroxide to react with compound 2 and (ii) for the aqueous solution to pass through layers 3 and 5 in the device. If more of compound 2 converts to hydrophilic products than compound 1 within the time frame of flow-through, then less hydrogen peroxide would be needed to allow flow-through using compound 2, increasing the sensitivity for the assay. Oligomers modeled after compound 2 provide a greater change in hydrophobicity than compound 2 by converting from a large hydrophobic molecule (an oligomer) to small hydrophilic products upon reaction with hydrogen peroxide, further increasing the sensitivity for the assay, since the change in wetting properties will be amplified relative to compound 2. The proposed mechanism of response for the oligomers is as follows: oxidative cleavage of the aryl boronate in compounds 3-6 would generate phenol, which would initiate a cascade head-to-tail depolymerization reaction through quinone- and azaquinone-methide-mediated pathways, similar to the mechanism depicted for compound 1 in FIG. 1B.

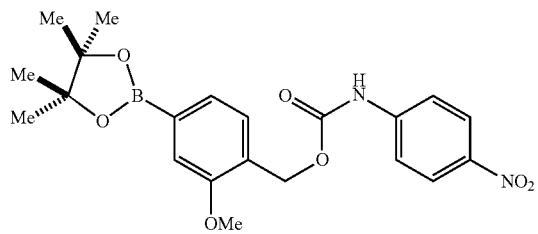

Compound 2

Compound 2 was prepared from 4-(hydroxymethyl)-3-methoxyphenylboronic acid pinacol ester and p-nitrophenyl isocyanate. Compounds 3 and 4 were prepared in a step-wise fashion, while oligomers 5 and 6 were prepared according to the route outlined in Scheme 1. This route involved a tin-catalyzed polymerization of monomer 8, wherein the length of the oligomer was controlled by polymerization time. The polymerization reaction was quenched by addition of the aryl boronate end-cap, and a postpolymerization modification was used to append the p-nitrophenyl carbamate.

Scheme 1

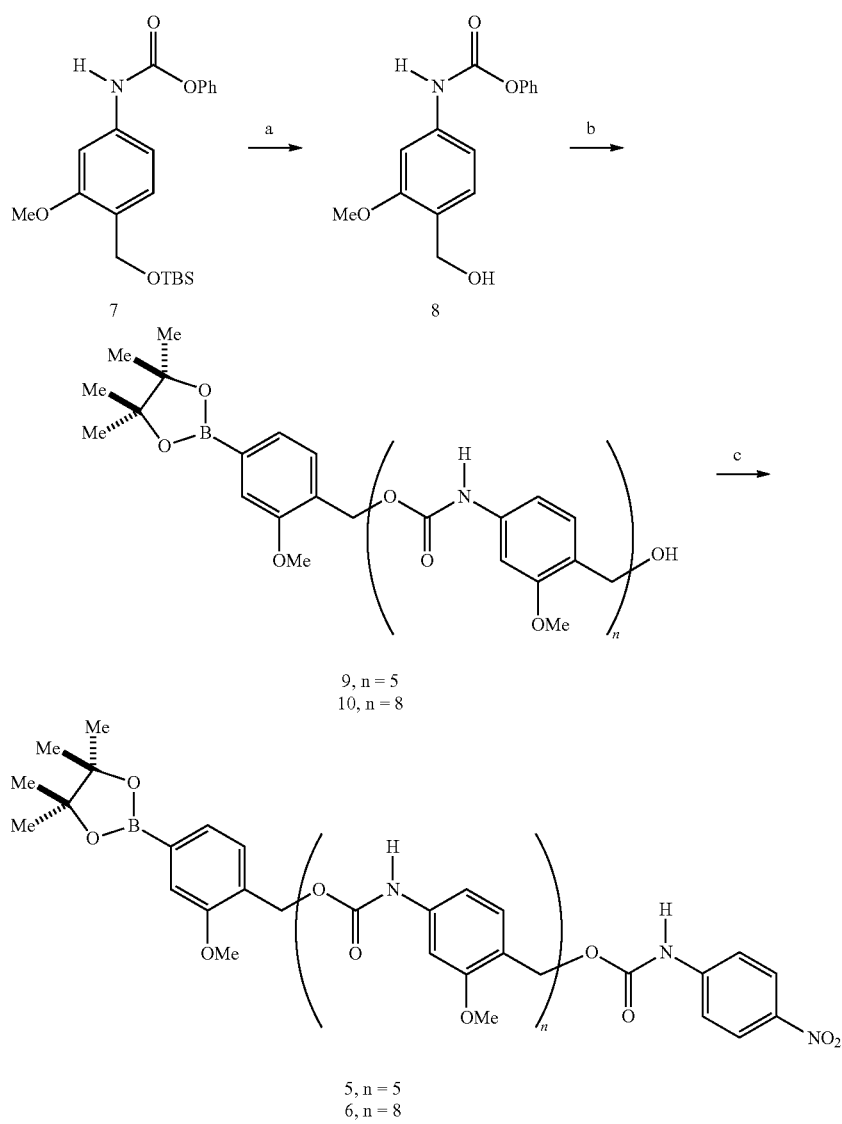

<sup>a</sup>Reagents and conditions: (a) TsOH, THF—H₂O (87%); (b) (i) DBTL. (ii) 4-(hydroxymethyl)-3-methoxyphenylboronic acid pinacol ester. DMSO 110° C. (33% for 9, 64% for 10); (c) 4-nitrophenyl isocyanate, TEA, DMF (71% for 5, 92% for 6).

Addition of a methyl ether (such as the methyl ether in compound 2 vs. compound 1) can accelerate the rate of quinone- and azaquinone-methide-mediated release of a benzylic group by as much as 40× compared with a derivative that lacks the methyl ether. After optimizing the quantity of 2 needed for this quantitative flow-through assay, the anticipated difference in rate between compound 1 and compound 2 provided a 17-fold improvement in the sensitivity for the assay (i.e., LOD=1707 µM for 1 vs. 103 µM for 2). Formation of quinone methide can be a rate-limiting step under the conditions of the assay.

Figure 15:
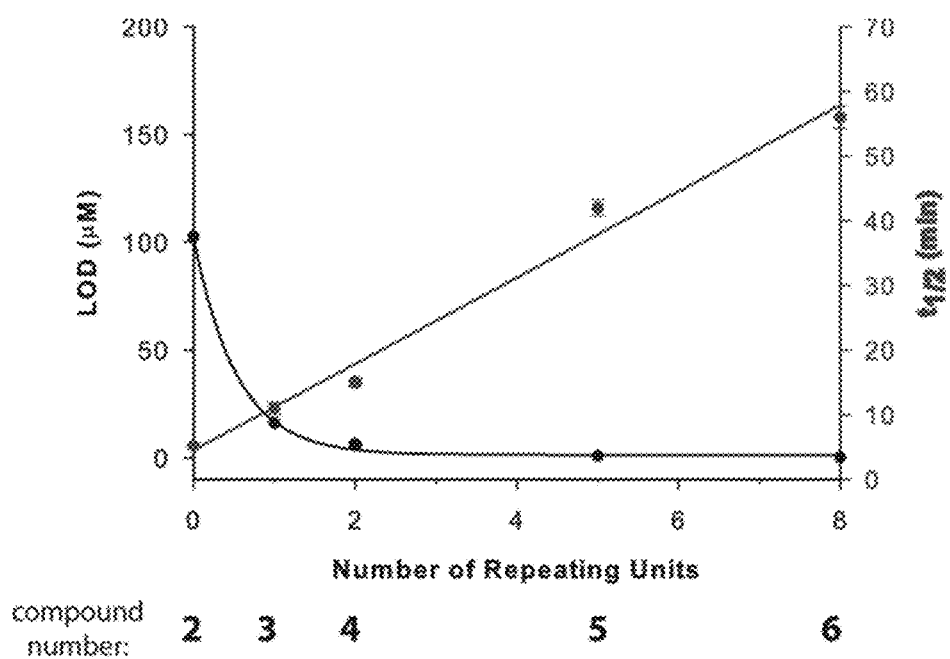
FIG. 15 shows the limit of detection as a function of detection reagent repeat units.

Oligomers 3-6 impart significant improvements in sensitivity to the assay compared to 1 and 2 (FIG. 15). For example, after optimizing the quantity of each reagent for the flow-through assay, it was found that addition of one repeating unit (e.g., oligomer 3) improved the limit of detection 6× compared to 2 and 107× compared to compound 1. In fact, a nearly linear relationship exists between the limit of detection and the number of repeating units in the oligomer until, presumably, the rate of hydrogen peroxide-induced depolymerization becomes competitive with the residence time of the sample within layers 3 and 5 of the device (FIG. 15). Incomplete depolymerization would affect the magnitude of hydrophobic-to-hydrophilic phase-switching since the depolymerization intermediates (i.e., truncated oligomers) are expected to retain substantial hydrophobic character relative to the products of complete depolymerization. There appears to be a match in depolymerization time and flow-through time when approximately 2-5 repeating units are added to compound 2, at which point less dramatic improvement in sensitivity is obtained when using longer oligomers that depolymerize more slowly than oligomer 4 (e.g., oligomer 6, n=8, has a LOD=0.15 µM, whereas 5, n=5, has a LOD=0.96 µM).

Devices were prepared with one, two, or three layers of paper that were modified with oligomer 3. The relationship between the limit of detection and the total quantity of oligomer 3 was then characterized within the devices to determine the minimum quantity of 3 needed to provide the lowest limit of detection. These experiments revealed that a device containing one layer of oligomer 3 provided a limit of detection for hydrogen peroxide that is nearly 5× better than a comparable device containing three layers of oligomer 3 (e.g., the LOD for one layer of 3==9.4 µM, while three layers of 3=46 µM). Specifically, the limit of detection worsens by ~2× every additional layer of oligomer 3 incorporated into the device. Likewise, the dynamic range for the assay worsens as the number of layers containing oligomer 3 increases. For example, the device containing one layer of oligomer 3 has a dynamic range of 9.7 µM to 1000 µM, whereas the device containing three layers of oligomer 3 has a smaller dynamic range of 57 µM to 500 µM. A device with improved sensitivity can provide a single layer where the magnitude of phase-switching is substantial, rather than providing small stages of phase-switching over several layers in a device.

A single layer device was produced, and was used to determine the optimum quantity of oligomer 5 (the oligomer that provided the best limit of detection) needed to provide the lowest limit of detection for quantifying hydrogen peroxide in a sample. This assay requires only 3.4 µg of oligomer 5, yet now provides measurements of hydrogen peroxide down to 31 nM, which is a LOD that is 55,000× better than the aforementioned assay, as well as a useful dynamic range.

The LOD for hydrogen peroxide of 31 nM is sufficiently sensitive to measure hydrogen peroxide in rain and other sources of water, for example, where the presence of hydrogen peroxide is indicative of pollution.

Materials. All reactions were performed in flame-dried glassware under a positive pressure of argon unless otherwise noted. Air- and moisture-sensitive liquids were transferred via syringe or stainless steel cannula. Organic solutions were concentrated by rotary evaporation (25-40 mmHg) at 30° C. All reagents were purchased commercially and were used as received unless otherwise noted. 4-Nitrophenyl isocyanate was recrystallized from petroleum ether prior to use. N,N-Dimethylformamide, dimethylsulfoxide, tetrahydrofuran, and triethylamine were purified by known method. Flash-column chromatography was performed by known methods, employing silica gel (60 Å pore size, 32-63 µm, standard grade). Thin-layer chromatography was carried out on silica gel TLC plates (20×20 cm w/h, F-254, 250 µm). Deionized water was purified by filtration and irradiation with UV light. The papers used were Whatman Chromatography Paper Grade I and Boise Aspen 30 Printer Paper (92 brilliant, 30% postconsumer content), and the tape was Ace Hardware Plastic carpet tape (part #50106).

Methods. Proton nuclear magnetic resonance ($^1$H NMR) spectra and carbon nuclear magnetic resonance spectra ($^{13}$C NMR) were recorded using either a 300 MHz, 360 MHz, or 400 MHz NMR spectrometer at 25° C. Proton chemical shifts are expressed in parts per million (ppm) and are referenced to residual protium in the NMR solvent (CHCl$_3$ δ 7.26 ppm, CO(CH$_3$)$_2$ δ 2.05 ppm, or SO(CH$_3$)$_2$ δ 2.50 ppm). Data are represented as follows: chemical shift, multiplicity (s=singlet, bs=broad singlet, d=doublet, t=triplet, m=multiplet and/or multiple resonances), integration, and coupling constant (J) in Hertz. Carbon chemical shifts are expressed in parts per million and are referenced to the carbon resonances of the NMR solvent (CDCl$_3$ δ0 77.0 ppm or CO(CH$_3$)$_2$ δ 29.8 and 206.3 ppm). UV/vis spectroscopic data were obtained using a six-cell spectrometer. Low resolution and high resolution mass spectra were acquired using mobile phases containing 5 mM ammonium formate. GPC data were acquired on a 300×7.5 mm, 3-100 µm particle size styrene divinyl benzene copolymer column using 1 mL/min N,N-dimethylformamide as the mobile phase. Molecular weights were calculated from low-angle and right-angle light scattering data. The system was calibrated using polystyrene standards.

Preparation of Compound 2. Triethylamine (52 µL, 0.38 mmol, 2.0 equiv) was added dropwise to a solution of 4-(hydroxymethyl)-3-methoxyphenylboronic acid pinacol ester (50 mg, 0.19 mmol, 1.2 equiv) and 4-nitrophenyl isocyanate (26 mg, 0.16 mmol, 1.0 equiv) in tetrahydrofuran (2.0 mL). The reaction mixture was stirred at 23° C. for 4 h. The solvent was removed by rotary evaporation and the residue was purified by silica gel flash column chromatography (10% ethyl acetate in hexanes, increasing to 20% ethyl acetate in hexanes) to afford compound 2 as a white, amorphous solid (46 mg, 0.11 mmol, 67%): IR (cm$^{-1}$) 3313, 2977, 2360, 1738, 1600, 1549, 1508; $^1$H NMR δ (360 MHz, CO(CH$_3$)$_2$) 9.46 (bs, 1H), 8.22 (d, 2H, J=9.3 Hz), 7.82 (d, 2H, J=9.3 Hz), 7.41 (d, 1H, J=7.3 Hz), 7.36 (d, 1H, J=7.4 Hz), 7.31 (s, 1H), 5.26 (s, 2H), 3.89 (s, 3H), 1.34 (s, 12H); $^{13}$C NMR δ (360 MHz, CO(CH$_3$)$_2$) 157.6, 154.0, 146.4, 143.4, 129.3, 128.4, 127.8, 125.7, 118.6, 116.4, 84.6, 62.9, 55.8, 25.2 (overlapping peaks in the aromatic region of the $^{13}$C spectrum); MS (TOF MS AP−) 427.2 (M-H$^+$); HRMS (TOF MS AP−) calcd for C$_{21}$H$_{24}$N$_2$O$_7$B (M-H$^+$) 427.1677, found 427.1657.

Preparation of Compound 8. p-Toluenesulfonic acid monohydrate (0.35 g, 1.9 mmol, 0.30 equiv) was added in one portion to a solution of compound 7 (2.4 g, 6.2 mmol, 1.0 equiv) in 4:1 tetrahydrofuran-water (62 mL) under an atmosphere of air. The reaction mixture was stirred at 23° C. for 4 h. Ethyl acetate (50 mL) and saturated aqueous sodium bicarbonate (10 mL) were added, each in one portion, and the layers were separated. The organic layer was washed with saturated aqueous sodium bicarbonate solution (1×50 mL) and was dried over sodium sulfate. The sodium sulfate was removed by filtration, the solvent was removed by rotary evaporation, and the residue was purified by silica gel flash column chromatography (20% ethyl acetate in hexanes, increasing to 60% ethyl acetate in hexanes) to afford compound 8 as a white, amorphous solid (1.5 g, 5.4 mmol, 87%): IR (cm$^{-1}$) 3540, 3470, 3269, 2963, 1727, 1615, 1547; $^1$H NMR δ (400 MHz, CDCl$_3$) 7.41-7.16 (m, 8H), 6.74 (d, 1H, J=Hz), 4.64 (s, 2H), 3.81 (s, 3H), 2.43 (bs, 1H); $^{13}$C NMR δ (300 MHz, CDCl$_3$) 158.0, 151.8, 150.4, 138.4, 129.4, 129.1, 125.8, 124.3, 121.6, 110.2, 101.6, 61.5, 55.3; MS (Q MS APCI+) 256.1 (M−OH$^-$); HRMS (TOF MS AP+) calcd for C$_{15}$H$_{14}$NO$_3$ (M−OH$^-$) 256.0974, found 256.0967.

Preparation of Oligomer 5. Compound 8 (0.60 g, 2.2 mmol, 1.0 equiv) was added in one portion to stirring dimethylsulfoxide (2.2 mL) at 110° C. Dibutyltin dilaurate (0.26 mL, 0.44 mmol, 0.2 equiv) was added in one portion and the reaction mixture was stirred for 2.75 min at 110° C. 4-(Hydroxymethyl)-3-methoxyphenylboronic acid pinacol ester (2.0 g, 7.6 mmol, 3.5 equiv) was added in one portion and the reaction mixture was stirred for 2 h at 110° C. The reaction mixture was cooled to 23° C. and poured into 0° C. methanol (20 mL). A yellow precipitate formed that was washed using a solid phase washing vessel by adding methanol, bubbling N$_2$ through the solution at a vigorous rate for 15 min, then draining the solvent. This process was repeated three times. The solids were dried under vacuum for 12 h to give oligomer 9 as an off-white powder (0.17 g, 0.15 mmol, 33%); $^1$H NMR δ (360 MHz, SO(CH$_3$)$_2$) 9.90 (bs, 1H), 9.80 (bs, 3H), 9.65 (bs, 1H), 7.29-7.19 (m, 12H), 7.00-6.98 (m, 6H), 5.15 (s, 2H), 5.04 (s, 8H), 4.84 (bs, 1H), 4.39 (s, 2H), 3.84-3.70 (m, 18H), 1.29 (s, 12H). GPC M$_n$=1.2 kDa, M$_w$=1.7 kDa, PDI=1.44.

Triethylamine (0.12 mL, 0.86 mmol, 10 equiv) was added dropwise to a solution of oligomer 9 (0.10 g, 86 μmol, 1.0 equiv) and 4-nitrophenyl isocyanate (71 mg, 0.43 mmol, 5.0 equiv) in dimethylformamide (1.7 mL). The reaction mixture was stirred for 16 h at 23° C., after which the solvent was removed by rotary evaporation. The residue was washed using a solid phase washing vessel with methanol (3×) followed by acetonitrile (2×). The solids were dried under vacuum for 12 h to give oligomer 5 as a peach-colored powder (0.81 g, 61 μmol, 71%); $^1$H NMR δ (360 MHz, SO(CH$_3$)$_2$) 10.45 (bs, 1H), 9.90 (bs, 1H), 9.80 (bs, 4H), 8.19 (d, 2H, J=9.3 Hz), 7.68 (d, 2H, J=9.1 Hz), 7.40-7.21 (m, 12H), 6.99 (d, 6H, J=8.3 Hz), 5.15 (s, 2H), 5.09-5.03 (m, 10H), 3.83-3.75 (m, 18H), 1.29 (s, 12H). GPC M$_n$=1.4 kDa, M$_w$=1.7 kDa, PDI=1.3.

Preparation of Oligomer 6. Compound 8 (0.60 g, 2.2 mmol, 1.0 equiv) was added in one portion to stirring dimethylsulfoxide (2.2 mL) at 110° C. Dibutyltin dilaurate (0.26 mL, 0.44 mmol, 0.2 equiv) was added in one portion and the reaction mixture was stirred for 5.0 min at 110° C. 4-(Hydroxymethyl)-3-methoxyphenylboronic acid pinacol ester (2.0 g, 7.6 mmol, 3.5 equiv) was added in one portion and the reaction mixture was stirred for 2 h at 110° C. The reaction mixture was cooled to 23° C. and poured into 0° C. methanol (20 mL). A yellow precipitate formed that was washed using a solid phase washing vessel with methanol (3×). The solids were dried under vacuum for 12 h to give oligomer 10 as a light yellow powder (0.30 g, 0.18 mmol, 64%); $^1$H NMR δ (400 MHz, SO(CH$_3$)$_2$) 9.89 (bs, 1H) 9.78 (bs, 6H), 9.63 (bs, 1H), 7.41-7.19 (m, 18H), 7.03-6.95 (m, 9H), 5.16 (s, 2H), 5.04 (s, 14H), 4.82 (t, 1H, J=5.6 Hz), 4.40 (d, 2H, J=5.7 Hz), 3.94-3.67 (m, 27H), 1.30 (s, 12H). GPC M$_n$=1.3 kDa, M$_w$=2.3 kDa, PDI=1.73.

Triethylamine (0.16 mL, 1.2 mmol, 10 equiv) was added dropwise to a solution of oligomer 10 (0.20 g, 0.12 mmol, 1.0 equiv) and 4-nitrophenyl isocyanate (97 mg, 0.59 mmol, 5.0 equiv) in dimethylformamide (2.4 mL). The reaction mixture was stirred for 16 h at 23° C., after which the solvent was removed by rotary evaporation. The residue was washed using a solid phase washing vessel with methanol (3×) followed by acetonitrile (2×). The solids were dried under vacuum for 12 h to give oligomer 6 as a peach-colored powder (0.19 g, 0.11 mmol, 92%); $^1$H NMR δ (360 MHz, SO(CH$_3$)$_2$) 10.46 (bs, 1H), 9.91 (bs, 1H) 9.80 (bs, 6H), 8.20 (d, 2H, J=9.1 Hz), 7.69 (d, 2H, J=9.2 Hz), 7.38-7.22 (m, 18H), 7.01-6.99 (m, 9H), 5.16 (s, 2H), 5.09-5.04 (m, 16H), 3.85-3.76 (m, 27H), 1.30 (s, 12H). GPC M$_n$=1.7 kDa, M$_w$=1.9 kDa, PDI=1.2.

Figure 16:
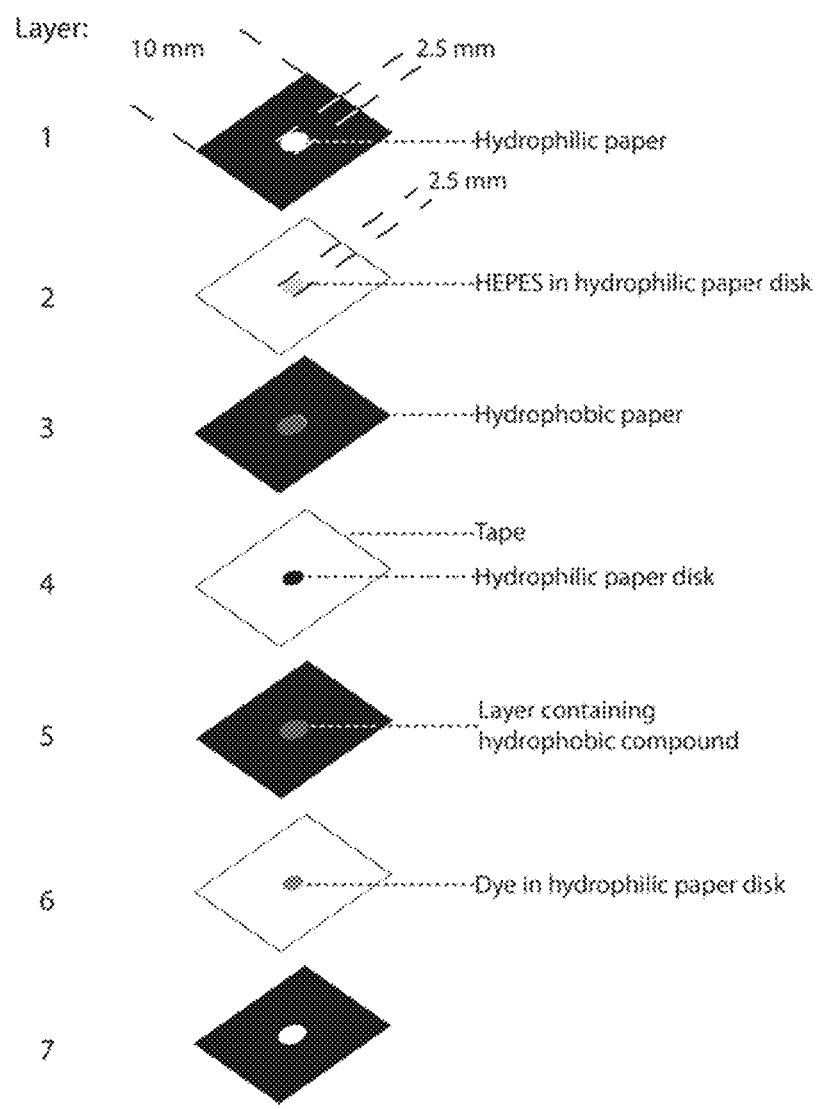
FIG. 16 illustrates the layout of a vertical flow-through assay device.

Procedure for fabricating the paper-based microfluidic device. The paper was patterned using a wax printer. The wax was melted into the paper by placing the patterned paper in an oven at 150° C. for 105 s. The devices were assembled; the layout of the device is shown in FIG. 16. Specifically, FIG. 16 shows an expanded view of the device shown in FIG. 12. The device is 10 mm wide×10 mm long×0.9 mm thick. The paper used for all layers of wax-patterned paper in the devices was Boise Aspen 30 Printer Paper (92 brilliant, 30% postconsumer content). Layer 2 contains a paper disk (2.5 mm-diameter×180 μm thick) soaked in HEPES buffer (45 mM, pH 8.0) and dried. Disks were loaded with HEPES by adding 600 μL of HEPES buffer to 320 mg of disks and dried under vacuum. Disks were Whatman Chromatography Paper Grade I paper fabricated using an Epilog Mini 24 Laser (CO$_2$ laser). Layers 3 and 5 were loaded with 0.25 μL of one of the hydrophobic detection reagents (e.g., compounds 1-6) dissolved in EtOAc (although compounds 5 and 6 were dissolved in THF). A solution of a hydrophobic detection reagent was spotted using a Drummond 0.25 μL disposable micropipette. Layer 6 contains a paper disk soaked in green dye. The disks were loaded with the green dye by adding 600 μL of green food coloring (1:5 food coloring-deionized-water) to 300 mg of disks followed by drying the disks under vacuum. After assembly, the devices were pressed using a rolling pin, applying medium pressure.

Procedure for measuring flow-through. The time required for a sample to flow through the device in FIG. 16 was measured as follows: to layer 1 was added 8 μL of an aqueous solution of H$_2$O$_2$. A timer was started immediately upon addition of the sample to the device. The device was turned over so that layer 7 was visible. The flow-through time was recorded when the hydrophilic region of layer 7 had completely changed color. Fourteen replicate tests were performed for each concentration of H$_2$O$_2$ and the two highest and two lowest flow-through times were removed from the data set to account for errors arising from failures during the device fabrication procedure.

Measuring the depolymerization kinetics were done as follows; p-Dioxanes (250 μL), dimethylsulfoxide (190 μL), and phosphate buffered water (40 μL, 0.01 M, pH 7.1) were added to a 2 mL vial and mixed by swirling the solution. A solution containing the oligomer (10 μL from a 0.01 M solution in DMSO) was added to the vial and vortexed for 5 s. Hydrogen peroxide (10 μL from a 0.2 M solution in phosphate buffered water, 0.01 M, pH 7.1) was added and the combined solution was aspirated using a pipet. The solution was transferred to a quartz cuvette (500 μL, 0.1 cm path length) and the absorbance value at 385 nm was monitored continuously. Half-lives were calculated based on the relative quantity of released p-nitroaniline.

Example 3. Multiplexed Assays for Quantitative Assessment of Active Enzymes

Quantitative assays for active enzymes can be conducted by measuring the time required for a reference region on a paper-based microfluidic device to turn green relative to an assay region. The intensity of the green color is not indicative of the quantity of the analyte; rather, the quantity of the analyte is directly related to the relative time required for the green color to appear. The assay is capable of measuring enzyme analytes in the picomolar range with assay times that range from ~30 s to ~12 min. The reference region in the device accounts for the effects of temperature, humidity, and sample viscosity on distribution rates within the device, and the assay provides quantitative results independent of the volume of the analyte (so long as a minimum volume is applied to the assay platform; e.g., 30 μL). The assay platform also includes preprocessing steps to remove contaminants that may be present in a sample that could interfere with the quantitative assay. Moreover, the platform can be configured to conduct multiple quantitative assays simultaneously while requiring that a user add a drop of a test fluid to the device, then measure the time between when the reference region and the assay region turn green.

Figure 17:
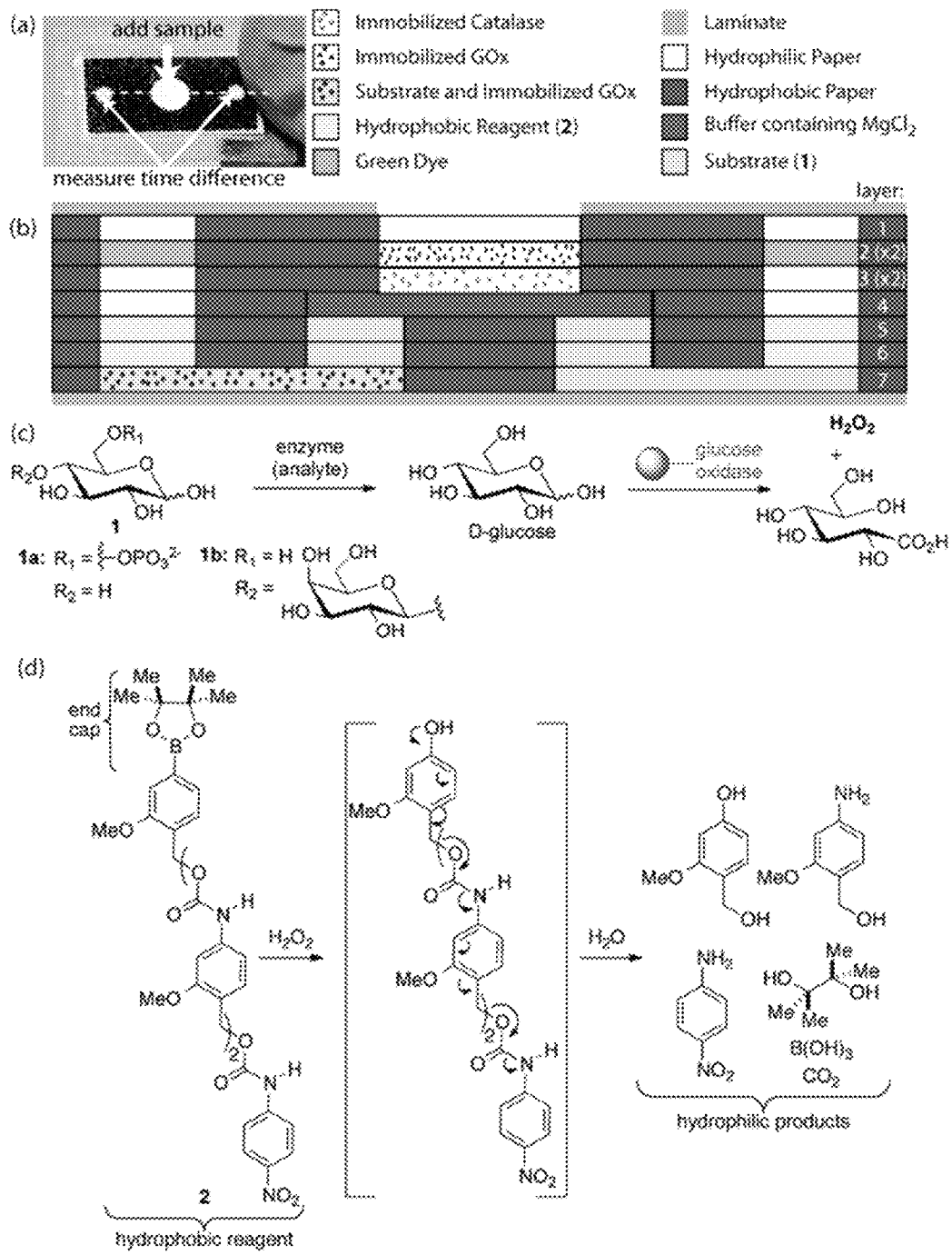
FIGS. 17A and 17B show the layout of a vertical and horizontal flow-through assay device.
FIGS. 17C and 17D show an enzyme assay detection reagent.

FIGS. 17A-17D depict an exemplary paper-based microfluidic device for measuring active enzyme analytes quantitatively by measuring the relative time required for a sample to turn a reference region green relative to when an assay region turns green. FIG. 17A shows a photograph of the device. The device is made from stacked layers of wax-patterned paper that are held together using spray adhesive and then laminated. The dimensions of the device are 20 mm×10 mm×1.8 mm. The white dotted line shows the location of the cross-section depicted in FIG. 17B. The left channel in FIG. 17B is the assay region and the right channel is the reference region. FIG. 17C shows specific substrate reagents are incorporated into the device to provide selective detection of the target enzyme analyte. FIG. 17D shows hydrophobic oligomer (e.g., oligomer 4) that amplifies signal for the detection event. Amplification arises from head-to-tail depolymerization.

This device has an entry point for addition of the sample, and hydrophilic channels of paper that split the sample into two equal directions (FIG. 17B). Layer 4 is where the sample splits into two directions, and where the sample encounters buffer salts to control the pH of the sample. In the left-hand channel in FIG. 17B, the sample re-dissolves a substrate for a target enzyme analyte (substrate 1, FIG. 17C), beginning in layer 5. If the target enzyme analyte is in the sample, it reacts with this substrate and causes release of one molecule of glucose per enzymatic reaction. After the sample continues through layers 5 and 6 and into layer 7, it encounters bead-bound glucose oxidase (FIGS. 17B-17C), which remains immobilized in the fibers of the paper. The glucose oxidase converts the released glucose into hydrogen peroxide as the sample wicks laterally in layer 7 of the device. Once the sample reaches the vertical conduit on the far left side of the device in FIG. 17B, it encounters an oligomer (e.g., oligomer 4 (n=2), FIG. 17D and FIG. 14B) that is hydrophobic, and thus alters the wetting properties of the paper from hydrophilic to hydrophobic (the synthesis of oligomer 4 is shown in Scheme 2, product is 51% overall yield; only 39.5 µg used per device). In the absence of hydrogen peroxide, the sample wicks slowly through this hydrophobic region, but in the presence of hydrogen peroxide, oligomer 4 converts to hydrophilic products through a cascade depolymerization reaction, thus switching the wetting properties of the paper from hydrophobic back to hydrophilic. This switching reaction amplifies the effects of hydrogen peroxide on the flow rate through layers 5 and 6 by converting a large, hydrophobic oligomer (rather than a small molecule) into hydrophilic products. This switching reaction also allows the sample to pass through the layers containing oligomer 4 with a rate that depends on the concentration of hydrogen peroxide in the sample, which ultimately reflects the concentration of the target enzyme analyte. Once the sample passes through the layers containing oligomer 4, it continues to wick in the vertical direction until it re-dissolves dried green food coloring and carries the highly colored solution to the top layer where the bright green color becomes visible.

The reference channel (right direction in layer 4 in the cross-section in FIG. 17B) contains the same reagents in the same order as the left-hand channel, with the exception of bead-bound glucose oxidase. In this channel, the enzyme analyte (if present) will react with the substrate deposited into the channel and generate glucose, but the glucose will not be converted into hydrogen peroxide, therefore hydrogen peroxide will not be present to react with oligomer 4. Consequently, the time required for the sample to pass through this reference region (and carry the green color to the viewing region on the top of the device) depends entirely on the temperature and humidity under which the assay is conducted, as well as on the viscosity of the sample. These factors will affect wicking rates in the assay region as well (the left-hand channel); therefore this reference region normalizes the output of the assay for the effects of these variables on sample distribution. The reference region normalizes the output of the assay since the readout is the time required for the reference region to turn green relative to when the assay region (the left-hand region) turns green.

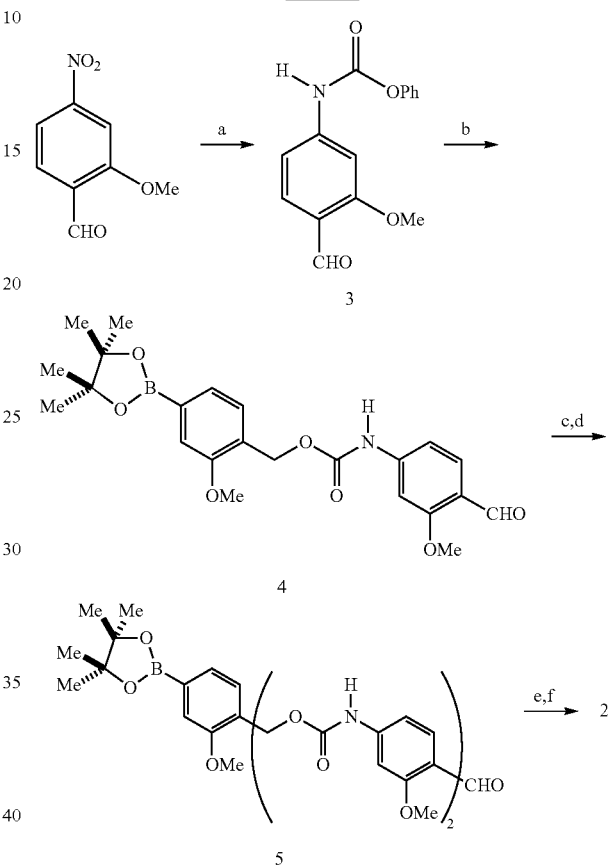

Scheme 2

<sup>a</sup>Reagents and conditions: (a) Pd/C, H₂; PhOCOCl, DIEA (86%); (b) 4-(hydroxymethyl)-3-methoxyphenylboronic acid pinacol ester, DBTL, 110° C. (97%); (c) NaBH₄; (d) DBTL, 110° C. (83% over 2 steps); (e) NaBH₄; (f) 4-nitrophenyl isocyanate, 80° C. (74% over 2 steps).

Figure 18:
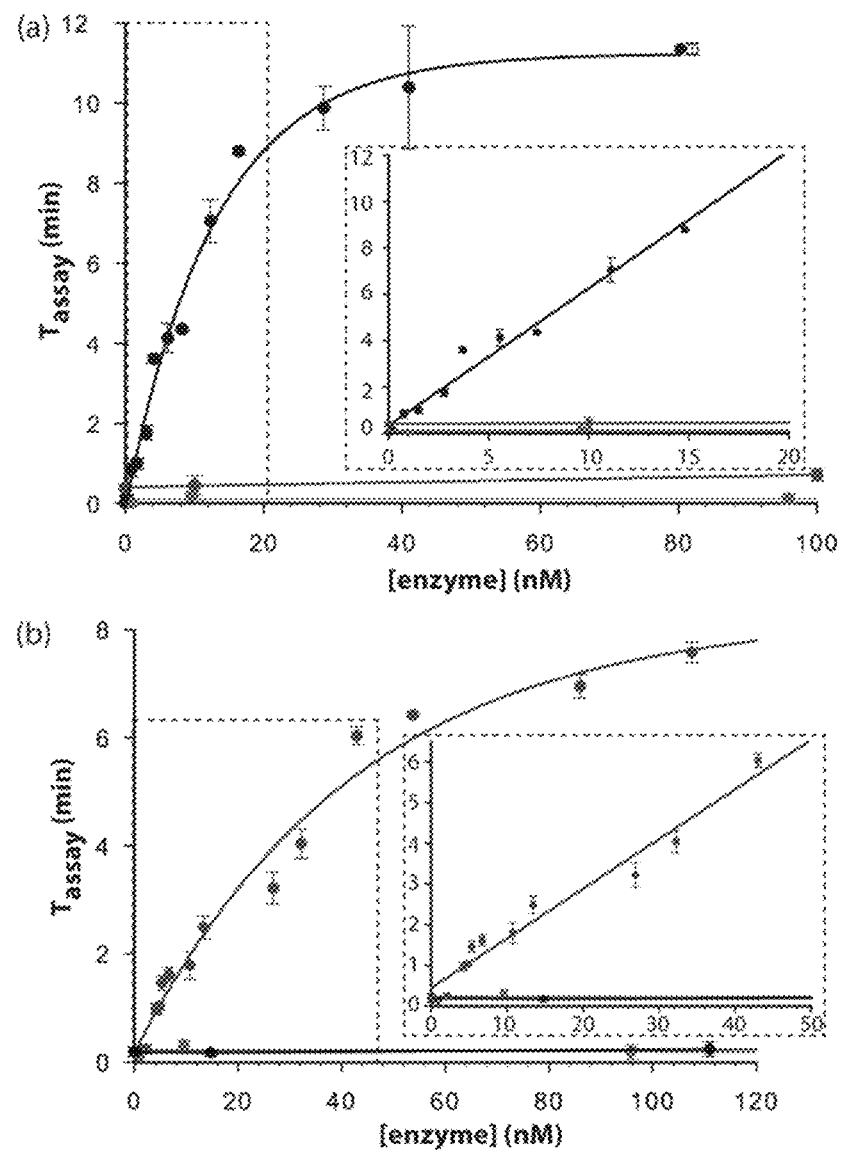
FIGS. 18A and 18B show calibration curves for devices comprising enzyme assays.

The performance of the assay is demonstrated by the calibration curves shown in FIGS. 18A and 18B for the model enzyme analytes alkaline phosphatase and β-D-galactosidase. In FIG. 18A, the analyte is alkaline phosphatase, which uses substrate 1a as the substrate in the device. The calibration curve was generated by depositing samples of alkaline phosphatase in 40 mM HEPES buffer (pH 8.0) to the top of the device and measuring the time ($T_{assay}$) for the reference region to turn green after the assay region turns green. The limit of detection for this assay is approximately 320 pM (0.355 U/L) alkaline phosphatase, with a dynamic range of approximately 148 pM (0.164 U/L) to approximately 14.8 nM (16.4 U/L). This level of sensitivity exceeds the sensitivity of colorimetric assays that use camera-equipped cellular phones for quantification, and is more sensitive than comparable activity-based assays that use a glucose meter to obtain the quantitative readout.

The calibration curves for FIG. 18A (alkaline phosphatase) and FIG. 18B (β-D-galactosidase) were obtained at 19° C. and 20% relative humidity. The data points are the average of three measurements and the error bars reflect the standard deviations of these averages. The equation for the line in (a) is y=0.591x+0.349, and the equation for the line in (b) is y=0.122x+0.436. The data for alkaline phosphatase is black, catalase is green, and β-D-galactosidase is blue. The assay is selective for alkaline phosphatase, as revealed by the negligible response when catalase or β-D-galactosidase are added to the device instead of alkaline phosphatase (green and blue data in FIG. 18A, respectively). Catalase was used for comparison to alkaline phosphatase since it decomposes hydrogen peroxide rapidly to water and oxygen, and thus should not provide a measurable response if the mechanism of the quantitative assay relies on analyte-induced production of hydrogen peroxide to allow flow through, as expected. β-D-Galactosidase was chosen because it belongs to a different enzyme family than alkaline phosphatase, and therefore demonstrates that selectivity between classes can be achieved by appropriate designs of substrate 1.

If the substrate in the device is switched to detect an enzyme other than alkaline phosphatase, then the selectivity switches as well (FIG. 18B). The calibration curve in FIG. 18B is for the enzyme β-D-galactosidase, which uses substrate 1b (FIG. 17C) as the substrate in the device. The limit of detection for this assay is comparable to the alkaline phosphatase assay (1.94 nM; 693 U/L), with a similar dynamic range (1.94 nM (693 U/L) to 43 nM (15,360 U/L)). This second calibration curve demonstrates that the assay can be reconfigured by changing the activity-based detection reagent (e.g., substrate 1) to target a variety of enzymes.

The device includes bead-bound glucose oxidase and bead-bound catalase to scavenge glucose and hydrogen peroxide that may be in a sample. The scavenging reagents are placed in the device in layers 2 and 3 (before the sample reaches the t-junction in the cross-section in FIG. 17B), and are capable of scavenging 40 mM glucose and 30 mM hydrogen peroxide when the device is challenged with a sample of alkaline phosphatase containing one or the other contaminants. The typical concentration of glucose in blood is 3.5-5.3 mM, while the highest levels of hydrogen peroxide in urine, beverages such as tea, or rain water (in a polluted environment) are 5-100 μM, 100 μM, and 5.4 μM, respectively. The device can remove these types of interfering contaminants.

The assay can provide quantitative results without requiring precise measurements of sample volume. The hydrophilic paper absorbs a fixed volume of sample, which provides sufficient control over sample volume to allow quantitative assays, so long as a minimum quantity of sample is added to the device. The minimum volume for the device shown in FIG. 17B is ~30 μL.

Figure 19:
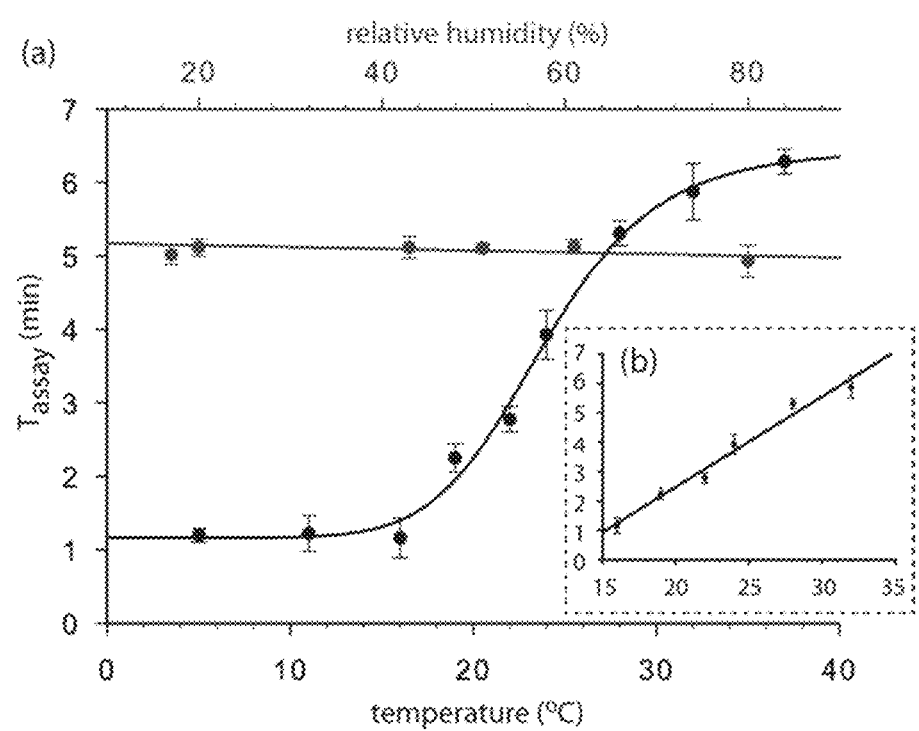
FIG. 19 shows the effect of humidity and temperature on the accuracy of assay devices.

FIG. 19 shows the effect of humidity and temperature on the accuracy of measuring $T_{assay}$ when using alkaline phosphatase as the model enzyme analyte (11 nM (12.3 U/L) for the humidity assay and 3.7 nM (4.1 U/L) for the temperature study). The data points are the average of three measurements and the error bars reflect the standard deviations from these averages. The inset in (b) depicts the linear region of the "temperature vs. $T_{assay}$" graph. The equation for the line is y=0.3079x−3.6831. It is demonstrated that the humidity of the environment has a negligible effect on the results of the quantitative assay. Variations in temperature, however, may affect the time required for a sample to flow through the device. Temperature-induced changes in sample viscosity affect wicking rates, but are likely accounted for by the reference region, whereas temperature effects on enzymatic activity are not. Instead, as depicted in the black data in FIG. 19, the assay time tracks with the activity of the target enzyme (alkaline phosphatase). The effects of assay temperature on enzymatic activity (and, ultimately assay time) can be accounted for since there are three temperature ranges (within the ranges tested) that affect the assay: (i) 5° C. to 15° C., (ii) 15° C. to 33° C., and (iii) >33° C. The enzymatic activity is equal within the first temperature range, so no adjustment is needed to the calibration curve in FIG. 18A with the exception of adding 1 min to the measured flow through times so that they match the times in the calibration curve, which were acquired at 19° C. Likewise, another plateau appears above 33° C., which requires subtraction of 4 min from the measured flow through times. Between the range of 15° C. to 33° C., however, the relative flow through times increase linearly. This linear increase is accommodated in a quantitative assay either by (i) decreasing the measured flow through time by a factor of 0.3079× (the difference in temperature when the assay was conducted versus when the calibration curve was conducted) (0.3079 is the slope of the linear region in the inset of FIG. 19) if the assay temperature is above 19° C. (the temperature for establishing the calibration curve), or (ii) by increasing the measured flow through time by the same factor if the temperature of the assay is below 19° C. By using these adjustments, the calibration curve in FIG. 18A remains functional over a wide range of temperatures.

Example 4. Multiplexed Assays for Quantitative Assessment of Heavy Metal Contaminants Materials. All reagents were purchased commercially and were used as received unless otherwise noted. All DNA sequences were purchased from Integrated DNA technologies in IDTE buffer (pH 7.5). Deionized water was purified by filtration and irradiation with UV light. The papers used were Whatman Chromatography Paper Grade 1 and Boise Aspen 30 Printer Paper (92 brilliant, 30% postconsumer content), and the adhesive used was 3M™ Super 77™ Multipurpose Adhesive. The laminate was Protac™ Ultra UV (8.0 mil) with a Diytac® JetMounter™ JM26 laminator. Devices and laminate were cut using an Epilog mini 24 $CO_2$ laser.

Sequence of DNA Strands. Sequence id DNA Strands are listed below:

```
Adenosine Assay1
Adenosine A:
                                      (SEQ ID NO: 1)
5'-biotin-AAAAAAAAAAAACCCAGGTTCTCT-3'

Adenosine B:
                                      (SEQ ID NO: 2)
5'-TCACAGGTAAGTAAAAAAAAAAAA-biotin-3'

Adenosine C:
                                      (SEQ ID NO: 3)
5'-TTTTTTACTCATCTGTGAAGAGAACCTGGGGGAGTATTGCGGAG
GAAGGT-3'

Lead Assay²
Lead A:
                                      (SEQ ID NO: 4)
5'-biotin-AAAAAAAAAAAAACAGACATCTCTTCTCCGAGCCGGT
CGAAATAGGTGTAG-3'

Lead B:
                                      (SEQ ID NO: 5)
5'-biotin-AAAAAAAAAAAATGTCCGATGCTACACTATrAGGAAG
AGATGTCTGT-3'
```

-continued

Mercury Assay[3]
Mercury A:
(SEQ ID NO: 6)
5'-TCTCAACTCGTAAAAAAAAAAAAA-biotin-3'

Mercury B:
(SEQ ID NO: 7)
5'-biotin-AAAAAAAAAAAACGCATTCAGGAT-3'

Reagent d:
(SEQ ID NO: 8)
5'-TTCGTGTTGTTCCTGTTTGCG-3'

Adenosine aptamer beads: To 500 μL, of Adenosine B (25 μM) was added 250 μL, of Sphero™ streptavidin magnetic particles (1% w/v) (Spherotech, Lake Forest, Ill.) and 250 μL, of buffer. The suspension was mixed for 24 h in the dark at room temperature and then collected by magnetic separation. The beads were washed three times using buffer and redissolved in 500 μL, of buffer to give a 0.5% (w/v) working solution. The formed DNA sequence is referred to as Bead-Adenosine B.

Assay: To 200 μL, of Adenosine A (12.5 μM) was added 25 μL, of streptavidin glucose oxidase (1 mg/ml) (Rockland Immunochemicals Inc., Gilbertsville, Pa.) and 575 μL, of 200 mM phosphate buffer (pH 7.5). The solution was mixed at room temperature for 24 h in the dark and then collected using a Pall Nanosep® 100K omega centrifugal filter. The sample was washed three times with buffer and then redissolved in 300 μL, of buffer to give a working solution. The formed DNA sequence is referred to as GOX-Adenosine A. To 200 μL, of Bead-Adenosine B was added 100 μL, of GOX-Adenosine A and 100 μL, of Adenosine C. The solution was mixed at room temperature in the dark for 90 min and then collected by magnetic separation. The suspension was washed three times with 40 mM HEPES buffer (pH 8.0) and redissolved in HEPES buffer. The final volume of buffer used was varied to change the concentration of adenosine aptamer solution added to the device.

Control: To 100 μL, of Adenosine A (12.5 μM) was added 625 μL, of streptavidin (2 μM). The solution was mixed at room temperature for 24 h in the dark and then collected using a Pall Nanosep® 10K omega centrifugal filter. The sample was washed three times with buffer and redissolved in 300 μL, of buffer to give a working solution. The formed DNA sequence is referred to as Strep-Adenosine A. To 200 μL, of Bead-Adenosine B was added 100 μL, of Strep-Adenosine A and 100 μL, of Adenosine C. The solution was mixed at room temperature in the dark for 90 min and collected by magnetic separation. The suspension was washed three times with 40 mM HEPES buffer (pH 8.0) and redissolved in HEPES buffer. The final volume of buffer used was varied to change the concentration of adenosine aptamer solution added to the device.

Lead aptamer beads: To 500 μL of Lead A (25 μM) was added 250 μL of Sphero™ streptavidin magnetic particles (1% w/v) (Spherotech, Lake Forest, Ill.) and 250 μL of buffer. The suspension was mixed for 24 h in the dark at room temperature and collected by magnetic separation. The beads were washed three times using buffer and redissolved in 500 μL of buffer to give a 0.5% (w/v) working solution. The formed DNA sequence is referred to as Bead-Lead A.

Reagent 1: To 200 μL of Lead B (12.5 μM) was added 25 μL of streptavidin glucose oxidase (1 mg/ml) (Rockland Immunochemicals Inc., Gilbertsville, Pa.) and 575 μL of 200 mM phosphate buffer (pH 7.5). The solution was mixed at room temperature for 24 h in the dark and collected using a Pall Nanosep® 100K omega centrifugal filter. The sample was washed three times with buffer and redissolved in 300 μL of buffer to give a working solution. The formed DNA sequence is referred to as GOX-Lead B. To 300 μL of Bead-Lead A was added 300 μL of GOX-Lead B. The solution was mixed at room temperature in the dark for 90 min and collected by magnetic separation. The suspension was washed three times with 40 mM HEPES buffer (pH 8.0) and redissolved in 300 μL of HEPES buffer to give a 0.5% (w/v) working solution.

Reagent 2: To 200 μL of Lead B (12.5 μM) was added 625 μL of streptavidin (2 μM). The solution was mixed at room temperature for 24 h in the dark and collected using a Pall Nanosep® 10K omega centrifugal filter. The sample was washed three times with buffer and redissolved in 300 μL of buffer to give a working solution. The formed DNA sequence is referred to as Strep-Lead B. To 300 μL of Bead-Lead A was added 300 μL of Strep-Lead B. The solution was mixed at room temperature in the dark for 90 min and collected by magnetic separation. The suspension was washed three times with 40 mM HEPES buffer (pH 8.0) and redissolved in 300 μL of HEPES buffer to give a 0.5% (w/v) working solution.

Mercury Aptamer: Reagent c: To 500 μL of Mercury A (25 μM) was added 250 μL of Sphero™ streptavidin magnetic particles (1% w/v) (Spherotech, Lake Forest, Ill.) and 250 μL of buffer. The suspension was mixed for 24 h in the dark at room temperature and collected by magnetic separation. The beads were washed three times using buffer and the supernatant was removed and the beads were stored for use later. The formed DNA sequence is referred to as Reagent c.

Reagent 3: To 200 μL, of Mercury B (12.5 μM) was added 25 μL, of streptavidin glucose oxidase (1 mg/ml) (Rockland Immunochemicals Inc., Gilbertsville, Pa.) and 575 μL, of 200 mM phosphate buffer (pH 7.5). The solution was mixed at room temperature for 24 h in the dark and collected using a Pall Nanosep® 100K omega centrifugal filter. The sample was washed three times with buffer and redissolved in 300 μL, buffer to give a working solution. The formed DNA sequence is referred to as Reagent b. To the solid Reagent c was added 300 μL, of Reagent b, and the solution was split into two 150 μL, aliquots. To one aliquot was added 100 μL, of Reagent d and 750 μL, of 40 mM HEPES buffer (pH 8.0) to give a 0.1% (w/v) working solution.

Reagent 4: To the second aliquot of Reagent c and reagent e was added 850 μL, of 40 mM HEPES buffer (pH 8.0) to give a 0.1% (w/v) working solution.

Figure 20:
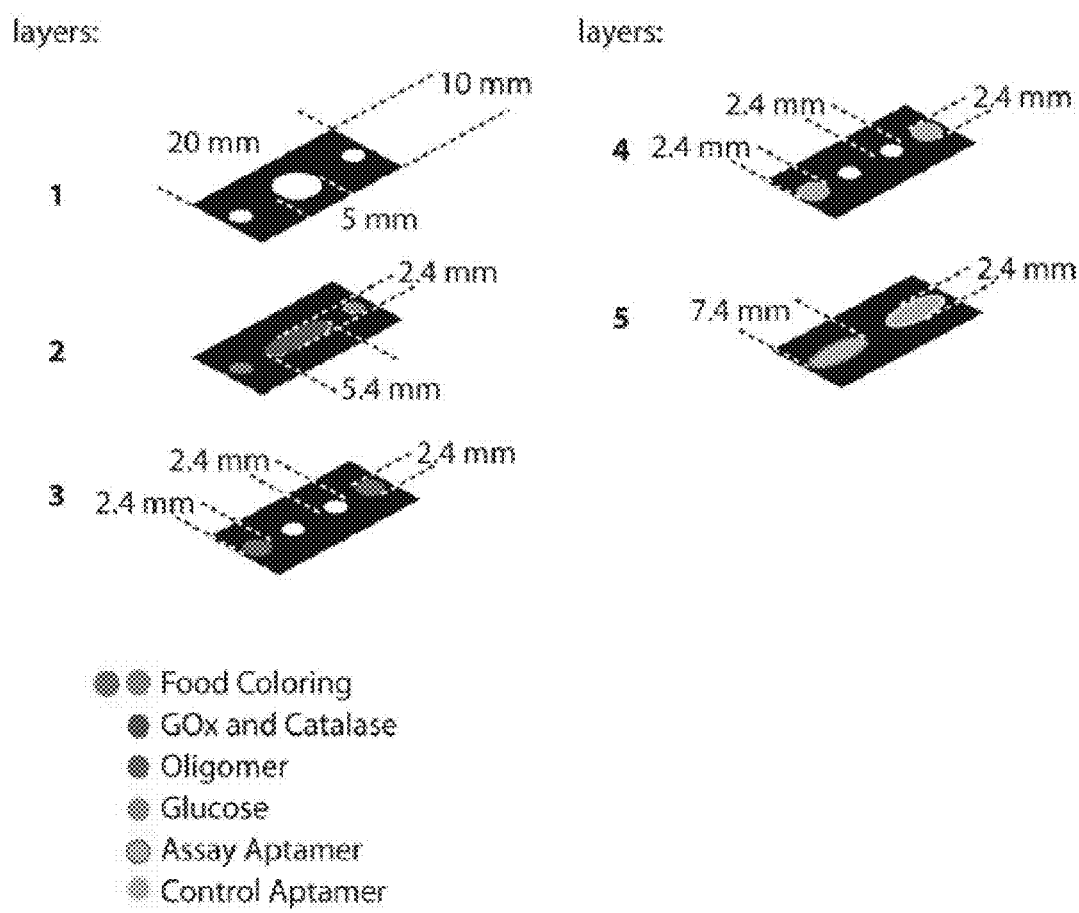
FIG. 20 illustrates a flow-through assay device.

Device for Assays of a Single Analyte. Assay devices for lead(II) or mercury(II) were assembled according to the procedure in Example 3. The layout of the device is shown in FIG. 20. The paper used for all layers was Whatman Chromatography Paper Grade I. Layer 2 contained 1 μL, of food coloring (1:5 food coloring: deionized-water) pre-deposited in the outer regions. The central region contained 8 μL, of immobilized glucose oxidase (0.25% w/v). The procedure for preparing the immobilized glucose oxidase was performed by known methods. Layer 2 also contained 8 μL, of immobilized catalase (0.25% w/v). The immobilized catalase was deposited in layer 2 and then allowed to air dry at room temperature for 45 minutes before the immobilized glucose oxidase was added and allowed to air dry. The outer two circles in layer 3 were predeposited with 0.25 μL, of oligomer 5 (4 mM) in THF. The outer circles in layer 4 were predeposited with 3 μL, of glucose (50 mM). Both channels in layer 5 were predeposited with 3 μL, of trehalose (1 M) and dried in ambient conditions for 30 minutes. The start channel in layer 5 (left-hand channel) was then pre-deposited with 3 μL, of the assay aptamer, while the stop channel (right-hand channel) was pre-deposited with 3 μL, of the control aptamer. All layers were air-dried in ambient conditions for 30 minutes after the reagents were deposited.

The devices were assembled as sheets (20 cm×20 cm) by aligning the edges of each layer on top of each other and using 3M™ Super 77™ Multipurpose Adhesive to adhere individual layers together. The sheets of devices were then pressed using a Drytac® JetMounter™ JM 26 laminator with medium pressure. Using a $CO_2$ laser (Epilog Mini 24 Laser), individual devices were cut out with tabs left between devices to allow for processing of the devices as a sheet. In a sheet of Protac™ Ultra UV (8.0 mil) (22 cm×22 cm), holes (d=5 mm) were cut using the $CO_2$ laser to align with individual devices in the sheet of devices. The devices were laminated between two sheets of 22 cm×22 cm Protac™ Ultra UV (the cut sheet covering layer 1) using a Drytac® JetMounter™ JM 26 with medium pressure. Following lamination, individual devices were cut out using scissors.

Figure 21:
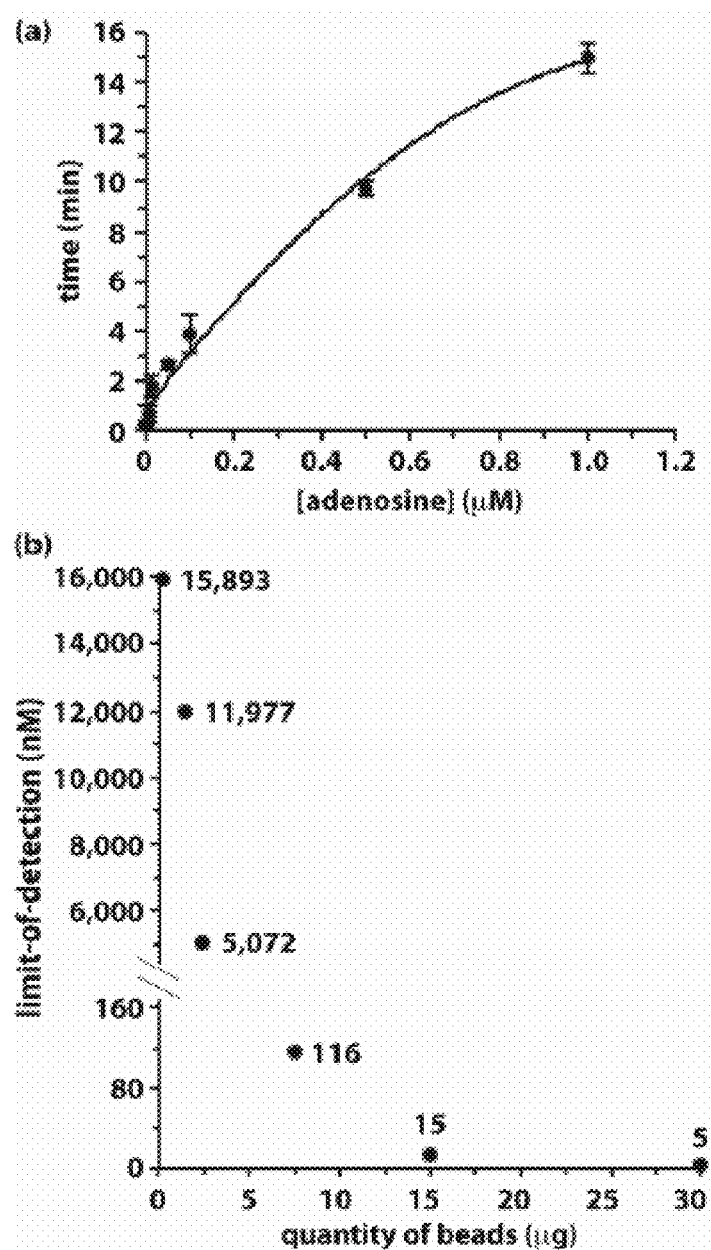
FIGS. 21A and 21B show detection of adenosine as a model target to demonstrate quantitative detection of an analyte using an aptamer-based device.

The devices contained two channels (one channel leading to a "start" region and the other to a "stop" region). The device was used along with aptamers for adenosine to demonstrate that the configuration of the device and the use of aptamers provided quantitative assays based on measurements of time (FIG. 20). The sensitivity of the assay was optimized by altering the quantity of the aptamer reagents. There was a quantitative relationship between the concentration of adenosine and the time-based measurement (FIG. 21A). The quantity of the aptamer in layer 5 had a profound impact on the limit-of-detection for the assay, where higher quantities of aptamer correlated with lower limits-of-detection (FIG. 21B). The limit-of detection for adenosine can be varied from 16 mM to 5 nM, with dynamic ranges of ~1000-fold for each variation in the quantity of the aptamer.

Immobilization of Enzymes on Polystyrene Beads. Catalase: To 1 mL of catalase (20 mg/mL) in 100 mM phosphate-buffered saline (pH 7.4) was added 5 mg biotin-X-NHS (EMD Chemicals, San Diego, Calif.) and mixed at room temperature for 4 hours to form biotin-catalase (b-catalase). The b-catalase was purified three times using PD-10 prepacked desalting column (GE Healthcare, Buckinghamshire, UK), washing with 100 mM phosphate-buffered saline (pH 7.4) and then concentrating by lyophilization. To 4 mg of b-catalase was added 1 mL of 9 μm-diameter Sphero™ streptavidin magnetic particles (1% w/v) (Spherotech, Lake Forest, Ill.) and the resulting solution was mixed for 3 hours. The streptavidin beads were washed four times with HEPES buffer (40 mM, pH 8.0), concentrating by centrifugation between washes and then concentrated by lyophilization. The lyophilized powder was dissolved in 2 mL of HEPES buffer to give an immobilized catalase working solution (0.25% w/v).

Glucose Oxidase: To 4 mg of biotin-glucose oxidase (b-GOx) (Rockland Immunochemicals Inc., Gilbertsville, Pa.) was added 1 mL of 9 μm-diameter Sphero™ streptavidin magnetic particles (1% w/v) (Spherotech, Lake Forest, Ill.) and the resulting solution was mixed for 3 hours. The streptavidin beads were washed four times with HEPES buffer (40 mM, pH 8.0), concentrating by centrifugation between washes and then concentrated by lyophilization. The lyophilized powder was dissolved in 2 mL of HEPES buffer to give an immobilized glucose oxidase working solution (0.25% w/v).

Procedure for Performing Assays for Single Analyte. The assay time was measured as follows: to layer 1 was added 60 μL of sample. When the "start" region turned green, a timer was started. The assay time was recorded when the "stop" region turned red. Six replicate tests were performed for each sample and both the highest and lowest assay times were removed from the data set to account for errors arising from failures during the device fabrication process.

Data for the Assay for Adenosine

Table 2 shows assay times for detecting adenosine in a single channel assay device containing 0.00625% (w/v) beads containing adenosine aptamer in layer 5. There were 6 replicates for each concentration of adenosine. To account for errors in fabricating the devices, the fastest and slowest assay times were not used in determining the average or standard deviation values.

TABLE 2

| Adenosine (nM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 1 | 7 | 10 | 20 | 21 | 28 | 14.5 | 7.1 |
| 10 | 6 | 7 | 12 | 27 | 27 | 142 | 18.3 | 10.3 |
| 25 | 8 | 10 | 26 | 26 | 33 | 42 | 23.8 | 9.7 |
| 50 | 48 | 52 | 68 | 73 | 113 | 256 | 76.5 | 25.9 |
| 100 | 27 | 141 | 203 | 204 | 215 | — | 190.8 | 33.6 |
| 250 | 306 | 315 | 315 | 322 | 324 | 333 | 319.0 | 4.7 |
| 500 | 521 | 545 | 583 | 596 | 631 | 656 | 588.8 | 35.5 |
| 1000 | 1225 | 1345 | 1375 | 1382 | 1391 | 1404 | 1373.3 | 19.9 |

Table 3 shows assay times for detecting adenosine in a single channel assay device containing 0.05% (w/v) beads containing adenosine aptamer in layer 5. There were 6 replicates for each concentration of adenosine. To account for errors in fabricating the devices, the fastest and slowest assay times were not used in determining the average or standard deviation values.

TABLE 3

| Adenosine (nM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 1 | 1 | 5 | 22 | 39 | 2700 | 16.8 | 17.4 |
| 10 | 4 | 7 | 8 | 16 | 33 | 82 | 16.0 | 12.0 |
| 50 | 114 | 132 | 152 | 152 | 172 | 180 | 152.0 | 16.3 |

TABLE 3-continued

| Adenosine (nM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 100 | 68 | 274 | 287 | 294 | 298 | 301 | 288.3 | 10.5 |
| 500 | 55 | 442 | 454 | 485 | 488 | 521 | 467.3 | 22.8 |
| 1000 | 11 | 665 | 881 | 889 | 925 | 1067 | 842.5 | 119.7 |

Table 4 shows assay times for detecting adenosine in a single channel assay device containing 0.083% (w/v) beads containing adenosine aptamer in layer 5. There were 6 replicates for each concentration of adenosine. To account for errors in fabricating the devices, the fastest and slowest assay times were not used in determining the average or standard deviation values.

TABLE 4

| Adenosine (nM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 6 | 11 | 12 | 12 | 21 | 33 | 14.0 | 4.7 |
| 1 | 1 | 2 | 2 | 10 | 16 | 20 | 7.5 | 6.8 |
| 5 | 18 | 22 | 25 | 32 | 41 | 52 | 30.0 | 8.4 |
| 10 | 8 | 32 | 42 | 47 | 67 | 74 | 47.0 | 14.7 |
| 50 | 61 | 67 | 88 | 109 | 110 | 138 | 93.5 | 20.4 |
| 100 | 265 | 289 | 296 | 304 | 344 | 381 | 3083 | 24.6 |
| 1000 | 892 | 906 | 911 | 914 | 915 | — | 911.5 | 4.0 |

Table 5 shows assay times for detecting adenosine in a single channel assay device containing 0.25% (w/v) beads containing adenosine aptamer in layer 5. There were 6 replicates for each concentration of adenosine. To account for errors in fabricating the devices, the fastest and slowest assay times were not used in determining the average or standard deviation values.

TABLE 5

| Adenosine (nM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 1 | 2 | 4 | 7 | 14 | 21 | 6.8 | 5.3 |
| 50 | 1 | 1 | 10 | 13 | 15 | 23 | 9.8 | 6.2 |
| 100 | 13 | 15 | 28 | 28 | 33 | 40 | 26.0 | 7.7 |
| 500 | 10 | 68 | 79 | 84 | 90 | 236 | 80.3 | 9.3 |
| 1000 | 126 | 132 | 142 | 143 | 149 | 158 | 141.5 | 7.0 |
| 10000 | 113 | 170 | 181 | 197 | 202 | 405 | 187.5 | 14.7 |
| 100000 | 28 | 326 | 431 | 452 | 524 | — | 433.3 | 81.8 |

Table 6 shows assay times for detecting adenosine in a single channel assay device containing 0.5% (w/v) beads containing adenosine aptamer in layer 5. There were 6 replicates for each concentration of adenosine. To account for errors in fabricating the devices, the fastest and slowest assay times were not used in determining the average or standard deviation values.

TABLE 6

| Adenosine (nM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 2 | 2 | 3 | 10 | 25 | 630 | 10.0 | 10.6 |
| 5 | 2 | 5 | 12 | 13 | 15 | 39 | 11.3 | 4.3 |
| 10 | 4 | 10 | 20 | 50 | 54 | 58 | 33.5 | 21.8 |
| 50 | 12 | 24 | 55 | 55 | 59 | — | 48.3 | 16.3 |
| 100 | 62 | 90 | 101 | 109 | 123 | 132 | 105.8 | 13.9 |
| 500 | 100 | 136 | 151 | 163 | 177 | — | 156.8 | 17.4 |
| 1000 | 275 | 370 | 433 | 437 | 438 | 670 | 419.5 | 33.1 |

TABLE 6-continued

| Adenosine (nM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 5000 | 22 | 450 | 462 | 463 | 464 | — | 459.8 | 6.6 |
| 10000 | 788 | 789 | 794 | 814 | 822 | 824 | 804.8 | 15.8 |

Table 7 shows assay times for detecting adenosine in a single channel assay device containing 1.0% (w/v) beads containing adenosine aptamer in layer 5. There were 6 replicates for each concentration of adenosine. To account for errors in fabricating the devices, the fastest and slowest assay times were not used in determining the average or standard deviation values.

TABLE 7

| Adenosine (nM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 9 | 11 | 11 | 13 | 14 | 21 | 12.3 | 1.5 |
| 1 | 1 | 2 | 3 | 21 | 22 | 26 | 12.0 | 11.0 |
| 5 | 11 | 12 | 45 | 48 | 52 | 89 | 39.3 | 18.4 |
| 10 | 77 | 86 | 87 | 116 | 138 | 138 | 106.8 | 25.1 |
| 50 | 127 | 150 | 151 | 160 | 172 | 173 | 158.3 | 10.2 |
| 100 | 118 | 182 | 218 | 244 | 292 | 306 | 234.0 | 46.3 |
| 500 | 539 | 564 | 575 | 602 | 603 | 608 | 586.0 | 19.6 |
| 1000 | 854 | 874 | 889 | 908 | 942 | 993 | 903.3 | 29.3 |

Effect of the Quantity of the Aptamer on the Limit-of-Detection of the Assay

Table 8 shows the change in limit of detection with mass of aptamer-beads added to devices for detecting adenosine.

TABLE 8

| Aptamer-Beads (µg) | LOD (nM) |
|---|---|
| 0.1875 | 15892.5 |
| 1.5 | 11977.0 |

TABLE 8-continued

| Aptamer-Beads (µg) | LOD (nM) |
|---|---|
| 2.49 | 5071.9 |
| 7.5 | 116.0 |
| 15 | 14.7 |
| 30 | 5.1 |

Samples containing 100 nM adenosine that were spiked with either glucose or hydrogen peroxide were added to the device for performing assays of a single analyte (FIG. 20). Devices that did not contain immobilized glucose oxidase and immobilized catalase were used to show the effects of glucose and hydrogen peroxide on assays lacking preprocessing.

Effects of Preprocessing

No preprocessing; Table 9 shows assay times for detecting 100 nM adenosine spiked with glucose in a single channel assay device containing 0.5% (w/v) beads containing adenosine aptamer in layer 5. No immobilized glucose oxidase or catalase was present in layer 2. There were 6 replicates for each concentration of glucose. To account for errors in fabricating the devices, the fastest and slowest assay times were not used in determining the average or standard deviation values.

TABLE 9

| Glucose (mM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 109 | 234 | 247 | 256 | 257 | 290 | 248.5 | 10.7 |
| 10 | 8 | 141 | 164 | 192 | 192 | — | 172.3 | 24.7 |
| 25 | 8 | 62 | 91 | 96 | 97 | — | 86.5 | 16.5 |
| 50 | 3 | 19 | 23 | 34 | 71 | 220 | 36.8 | 23.7 |

No preprocessing; Table 10 shows assay times for detecting 100 nM adenosine spiked with hydrogen peroxide in a single channel assay device containing 0.5% (w/v) beads containing adenosine aptamer in layer 5. No immobilized glucose oxidase or catalase was present in layer 2. There were 6 replicates for each concentration of hydrogen peroxide. To account for errors in fabricating the devices, the fastest and slowest assay times were not used in determining the average or standard deviation values.

TABLE 10

| Hydrogen Peroxide (mM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 109 | 234 | 247 | 256 | 257 | 290 | 248.5 | 10.7 |
| 0.5 | 1 | 2 | 7 | 8 | 11 | 16 | 7.0 | 3.7 |
| 10 | 2 | 13 | 36 | 38 | 43 | 64 | 32.5 | 13.3 |
| 25 | 1 | 1 | 2 | 3 | 10 | 24 | 4.0 | 4.1 |
| 50 | 5 | 6 | 26 | 32 | 32 | 44 | 24.0 | 12.3 |

With preprocessing; Table 11 shows assay times for detecting 100 nM adenosine spiked with glucose in a single channel assay device containing 0.5% (w/v) beads containing adenosine aptamer in layer 5. Immobilized glucose oxidase or catalase was present in layer 2. There were 6 replicates for each concentration of glucose. To account for errors in fabricating the devices, the fastest and slowest assay times were not used in determining the average or standard deviation values.

TABLE 11

| Glucose (mM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 203 | 209 | 247 | 249 | 260 | 275 | 241.3 | 22.2 |
| 10 | 12 | 251 | 265 | 268 | 282 | — | 266.5 | 12.7 |
| 25 | 112 | 198 | 205 | 212 | 238 | 258 | 213.3 | 17.5 |
| 50 | 68 | 285 | 223 | 242 | 270 | — | 230 | 35.7 |

With preprocessing; Table 12 shows assay times for detecting 100 nM adenosine spiked with hydrogen peroxide in a single channel assay device containing 0.5% (w/v) beads containing adenosine aptamer in layer 5. Immobilized glucose oxidase or catalase was present in layer 2. There were 6 replicates for each concentration of hydrogen peroxide. To account for errors in fabricating the devices, the fastest and slowest assay times were not used in determining the average or standard deviation values.

TABLE 12

| Hydrogen Peroxide (mM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 203 | 209 | 247 | 249 | 260 | 275 | 241.3 | 22.2 |
| 0.5 | 172 | 243 | 260 | 268 | 292 | 297 | 265.8 | 20.4 |
| 10 | 205 | 211 | 230 | 237 | 250 | 308 | 232.0 | 16.3 |
| 25 | 204 | 222 | 232 | 235 | 285 | 293 | 243.5 | 28.2 |
| 50 | 231 | 235 | 242 | 242 | 270 | 288 | 247.3 | 15.5 |

Assay for $Pb^{2+}$

Table 13 shows assay times for detecting lead(II) in a single channel assay device containing 0.5% (w/v) reagents 1 and 2 in layer 5. There were 6 replicates for each concentration of lead. To account for errors in fabricating the devices, the fastest and slowest assay times were not used in determining the average or standard deviation values.

TABLE 13

| Lead (II) (mM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 18 | 20 | 24 | 32 | 63 | 102 | 34.8 | 19.5 |
| 1 | 15 | 22 | 28 | 29 | 30 | 37 | 27.3 | 3.6 |
| 5 | 1 | 43 | 47 | 54 | 60 | 60 | 51.0 | 7.5 |
| 10 | 24 | 69 | 75 | 88 | 94 | 187 | 81.5 | 27.6 |
| 25 | 84 | 100 | 126 | 134 | 167 | 248 | 131.8 | 27.6 |
| 50 | 29 | 120 | 128 | 140 | 142 | 145 | 132.5 | 10.4 |
| 100 | 189 | 203 | 210 | 211 | 217 | 331 | 210.3 | 5.7 |

TABLE 13-continued

| Lead (II) (mM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 500 | 300 | 336 | 341 | 343 | 345 | 390 | 341.3 | 3.9 |
| 1000 | 40 | 300 | 357 | 377 | 395 | 439 | 357.3 | 41.2 |
| 100000 | 668 | 675 | 679 | 757 | 772 | 781 | 720.75 | 50.9 |

Assay for $Hg^{2+}$

Table 14 shows assay times for detecting mercury(II) in a single channel assay device containing 0.1% (w/v) reagents 3 and 4 in layer 5. There were 6 replicates for each concentration of mercury. To account for errors in fabricating the devices, the fastest and slowest assay times were not used in determining the average or standard deviation values.

TABLE 14

| Mercury (II) (mM) | Trial 1 (s) | Trial 2 (s) | Trial 3 (s) | Trial 4 (s) | Trial 5 (s) | Trial 6 (s) | Average (s) | Standard Deviation (s) |
|---|---|---|---|---|---|---|---|---|
| 0 | 1 | 12 | 18 | 23 | 50 | 70 | 25.8 | 16.8 |
| 1 | 13 | 16 | 50 | 72 | 96 | 519 | 58.5 | 34.0 |
| 5 | 89 | 109 | 132 | 159 | 163 | 184 | 140.8 | 25.3 |
| 10 | 226 | 232 | 245 | 262 | 270 | — | 252.3 | 17.1 |
| 25 | 114 | 297 | 328 | 332 | 335 | 345 | 323.0 | 17.6 |
| 50 | 114 | 393 | 417 | 432 | 434 | 610 | 419.0 | 18.9 |
| 100 | 442 | 524 | 585 | 593 | 618 | 619 | 580.0 | 39.9 |
| 10000 | 90 | 747 | 799 | 824 | 859 | 930 | 807.3 | 47.1 |

Figure 22:
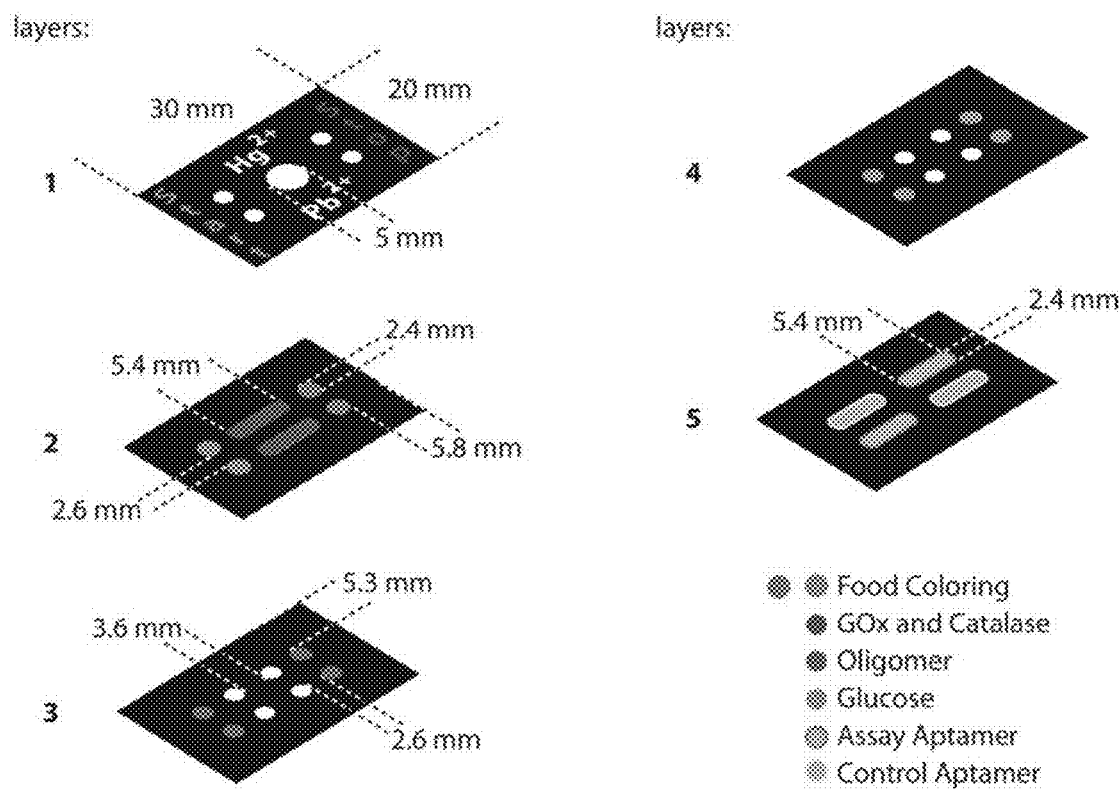
FIG. 22 illustrates a multiplexed flow-through assay device.

Fabrication of the device for performing assays on multiple analytes simultaneously. Devices were assembled according to the procedure in Example 3; the layout is shown in FIG. 22. The paper used for all layers was Whatman Chromatography Paper Grade I. Layer 2 contained 1 μL of food coloring (1:5 food coloring: deionized-water) pre-deposited in the outer regions. The central region contained 8 μL of immobilized glucose oxidase (0.25% w/v). Layer 2 also contained 8 μL of immobilized catalase (0.25% w/v). The immobilized catalase was deposited in layer 2 and then allowed to air dry at room temperature for 45 minutes before the immobilized glucose oxidase was added and allowed to air dry. The outer circles in layer 3 were predeposited with 0.25 μL of oligomer 5 (4 mM) in THF. The outer circles in layer 4 were predeposited with 3 μL of glucose (50 mM). All channels in layer 5 were predeposited with 3 μL of trehalose (1 M) and dried in ambient conditions for 30 minutes. For the mercury portion of the device (top row), the start channel in layer 5 (left-hand channel) was then pre-deposited with 3 μL of reagent 3, while the stop channel (right-hand channel) was pre-deposited with 3 μL of reagent 4. For the lead portion of the device (top row), the start channel in layer 5 (left-hand channel) was then pre-deposited with 3 μL of reagent 1, while the stop channel (right-hand channel) was pre-deposited with 3 μL of reagent 2. All layers were air-dried in ambient conditions for 30 minutes after reagents were deposited.

The devices were assembled as sheets (20 cm×20 cm) by aligning the edges of each layer on top of each other and using 3M™ Super 77™ Multipurpose Adhesive to adhere individual layers together. The sheets of devices were then pressed using a Drytac® JetMounter™ JM 26 laminator with medium pressure. Using a $CO_2$ laser (Epilog Mini 24 Laser), individual devices were cut out with tabs left between devices to allow for processing of the devices as a sheet. In a sheet of Protac™ Ultra UV (8.0 mil) (22 cm×22 cm), holes (d=5 mm) were cut using the $CO_2$ laser to align with individual devices in the sheet of devices. The devices were laminated between two sheets of 22 cm×22 cm Protac™ Ultra UV (the cut sheet covering layer 1) using a Drytac® JetMounter™ JM 26 with medium pressure. Following lamination, individual devices were cut out using scissors.

Procedure for performing assays on multiple analytes simultaneously. The assay time was measured as follows: to layer 1 was added 80 μL of sample. When the "start" region turned green, a timer was started. The assay time was recorded when the "stop" region turned red. Each assay (mercury and lead) was timed separately so that two times are measured, one for each analyte quantified. Six replicate tests were performed for each sample and both the highest and lowest assay times were removed from the data set to account for errors arising from failures during the device fabrication process.

Use of De-Ionized Water

Table 15 shows assay times for detecting mercury(II) and lead(II) in a multiple channel assay device containing 0.1% (w/v) reagents 3 and 4, and 0.5% (w/v) reagents 1 and 2 in layer 5. Samples were made using deionized water. There were 5 replicates for each sample. To account for errors in fabricating the devices, the fastest and slowest assay times were not used in determining the average or standard deviation values.

TABLE 15

| Heavy Metal(s) | Assay | Trial 1 (s) | Trial 2 (s) | Trial 3 (s) | Trial 4 (s) | Trial 5 (s) | Average (s) | Standard Deviation (s) |
|---|---|---|---|---|---|---|---|---|
| 0 nM $Pb^{2+}$ and 0 nM $Hg^{2+}$ | Hg(II) | 1 | 12 | 13 | 17 | 33 | 14.0 | 2.6 |
| | Pb(II) | 2 | 6 | 9 | 34 | 45 | 16.3 | 15.4 |
| 100 nM $Pb^{2+}$ and 0 nM $Hg^{2+}$ | Hg(II) | 1 | 2 | 4 | 1 | 22 | 6.0 | 5.3 |
| | Pb(II) | 189 | 203 | 220 | 243 | 244 | 222.0 | 20.1 |
| 0 nM $Pb^{2+}$ and 100 nM $Hg^{2+}$ | Hg(II) | 574 | 534 | 582 | 488 | 566 | 534.7 | 47.0 |
| | Pb(II) | 1 | 2 | 21 | 23 | 30 | 15.3 | 11.6 |
| 100 nM $Pb^{2+}$ and 100 nM $Hg^{2+}$ | Hg(II) | 504 | 506 | 541 | 557 | 580 | 534.7 | 26.1 |
| | Pb(II) | 234 | 238 | 236 | 236 | 309 | 236.7 | 1.2 |
| 100 nM $Pb^{2+}$, 100 nM $Hg^{2+}$, 100 nM $Cd^{2+}$ and 100 nM $Zn^{2+}$ | Hg(II) | 510 | 519 | 520 | 564 | 572 | 534.3 | 25.7 |
| | Pb(II) | 219 | 229 | 240 | 253 | 284 | 240.7 | 12.0 |

Use of Lake Water

Samples were prepared with lake water from Tussey Lake (40° 46' 11.28" N, 77° 45' 29.88" W). The lake water was spiked with lead(II) to simulate contaminated drinking water.

Table 16 shows assay times for detecting mercury(II) and lead(II) in a multiple channel assay device containing 0.1% (w/v) reagents 3 and 4, and 0.5% (w/v) reagents 1 and 2 in layer 5. Samples were made using lake water. There were 5 replicates for each sample. To account for errors in fabricating the devices, the fastest and slowest assay times were not used in determining the average or standard deviation values.

TABLE 16

| Heavy Metal(s) | Assay | Trial 1 (s) | Trial 2 (s) | Trial 3 (s) | Trial 4 (s) | Trial 5 (s) | Average (s) | Standard Deviation (s) |
|---|---|---|---|---|---|---|---|---|
| O nM $Pb^{2+}$ and 0 nM $Hg^{2+}$ | Hg(II) | 1 | 8 | 9 | 10 | 22 | 9.0 | 1.0 |
| | Pb(II) | 1 | 1 | 4 | 13 | 14 | 6.0 | 6.2 |
| 100 nM Pb2+ and 0 nM $Hg^{2+}$ | Hg(II) | 1 | 9 | 15 | 16 | 62 | 13.3 | 3.8 |
| | Pb(II) | 233 | 241 | 245 | 246 | 248 | 244.0 | 2.6 |
| 10 nM $Pb^{2+}$ and 0 nM $Hg^{2+}$ | Hg(II) | 1 | 1 | 1 | 17 | 69 | 6.3 | 9.2 |
| | Pb(II) | 70 | 80 | 81 | 83 | 83 | 81.3 | 1.5 |
| 1 nM $Pb^{2+}$ and 0 nM $Hg^{2+}$ | Hg(II) | 2 | 2 | 5 | 25 | 27 | 10.7 | 12.5 |
| | Pb(II) | 11 | 30 | 32 | 52 | 58 | 38.0 | 12.2 |

The disclosed assay for inorganic ions (e.g., $Pb^{2+}$ and $Hg^{2+}$) provides several advantages. The configuration uses aptamers and thus opens the assay strategy to new classes of analytes. The time-based approach can be used for quantitative analysis of enzymes, inorganic ions, and small molecules. The assays are easily reconfigured by exchanging reagents in the device both to alter the specificity for a target analyte, and to adjust the sensitivity and dynamic range of the assay(s). The strategy includes multiplexed assays, which allows complete analysis of samples using a single aliquot of the sample and a single step by the user. The assay is conveniently used, requiring that the user only add a sample onto the device. Pre-processing occurs within the device, and the device meters the volume of the sample to enable a quantitative readout. The assay platform includes reagents both for selective detection as well as signal amplification, yet no washing steps or other manipulations are required.

Figure 23:
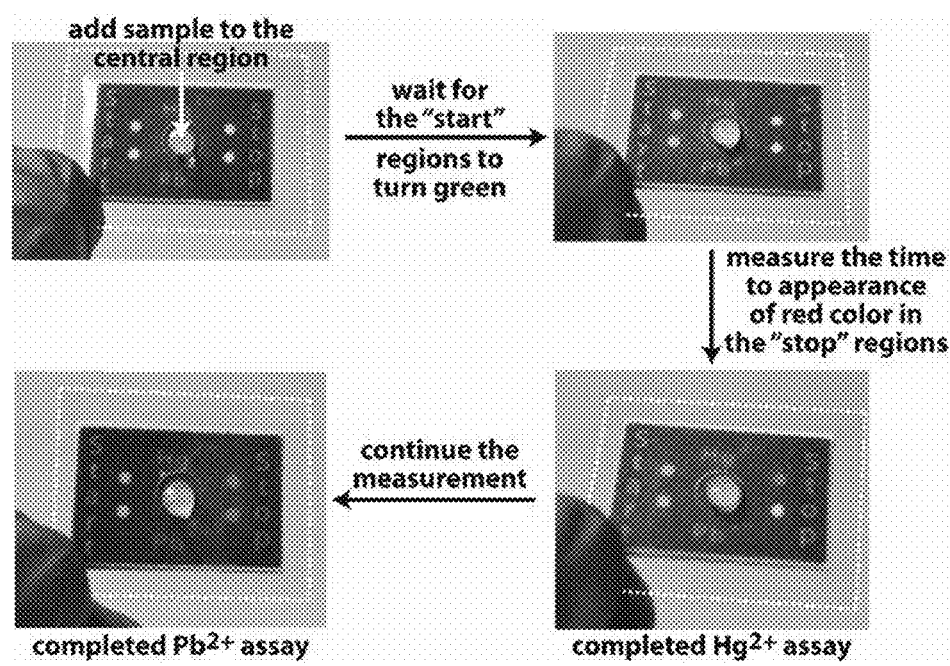
FIG. 23 depicts heavy metal analysis by a multiplexed flow-through assay device.

FIG. 23 depicts photographs of a paper-based assay platform for simultaneous measurements of $Hg^{2+}$ and $Pb^{2+}$ in drinking water. The white dotted lines denote the edges of laminate that hold multiple layers of stacked, wax-patterned paper in contact with one another. The dimensions of the stacked paper are 20 mm×30 mm×1.8 mm (FIG. 22). The device has hydrophobic regions that define where the sample travels by capillary action through the hydrophilic regions in the paper. Typically, a few minutes after adding the sample to the center region, the "start" hydrophilic region turns green, at which point the user begins to measure the time required for the "stop" region to turn red (FIG. 23). The measurement of time, which can be accomplished in a number of ways without using an electronic timer, reflects the concentration of the analyte in the sample. The device in FIG. 23 is configured to quantify $Hg^{2+}$ and $Pb^{2+}$ in water simultaneously. Therefore, once the sample of water is added to the entry point, it distributes into four separate portions of the device, two of which lead to "start" regions, while the other two lead to complementary "stop" regions.

Figure 24:
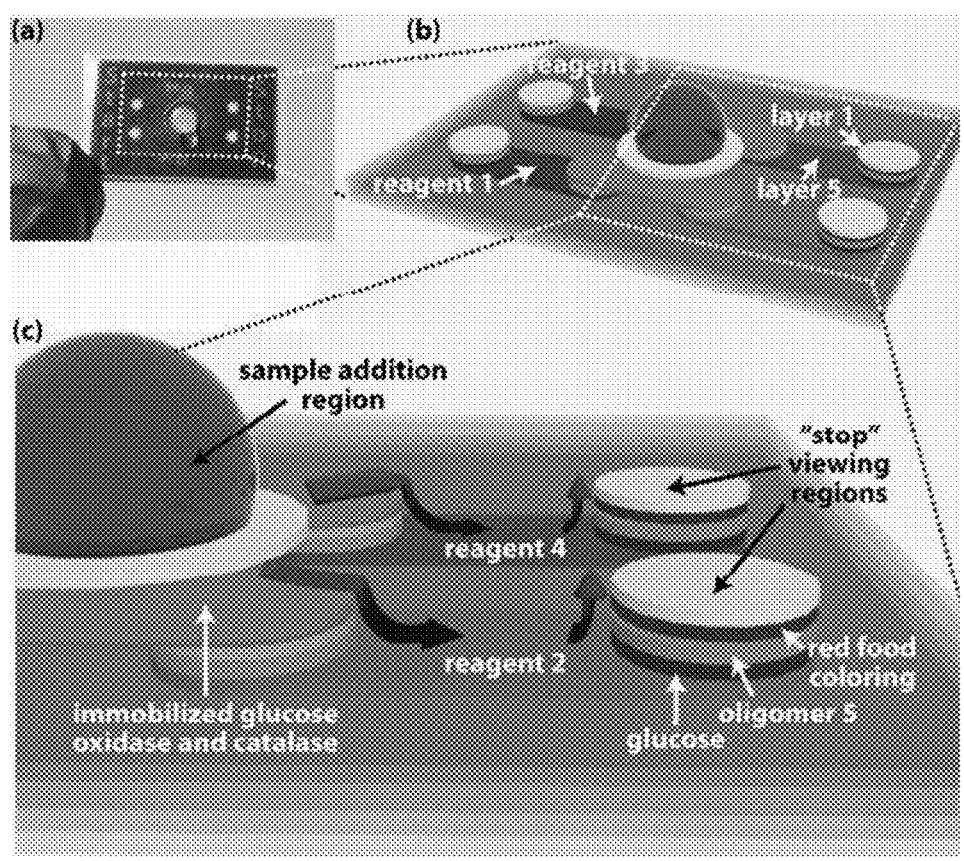
FIGS. 24A-24C illustrate a multiplexed flow-through assay device, wherein heavy metal analysis can be performed.
Figure 25:
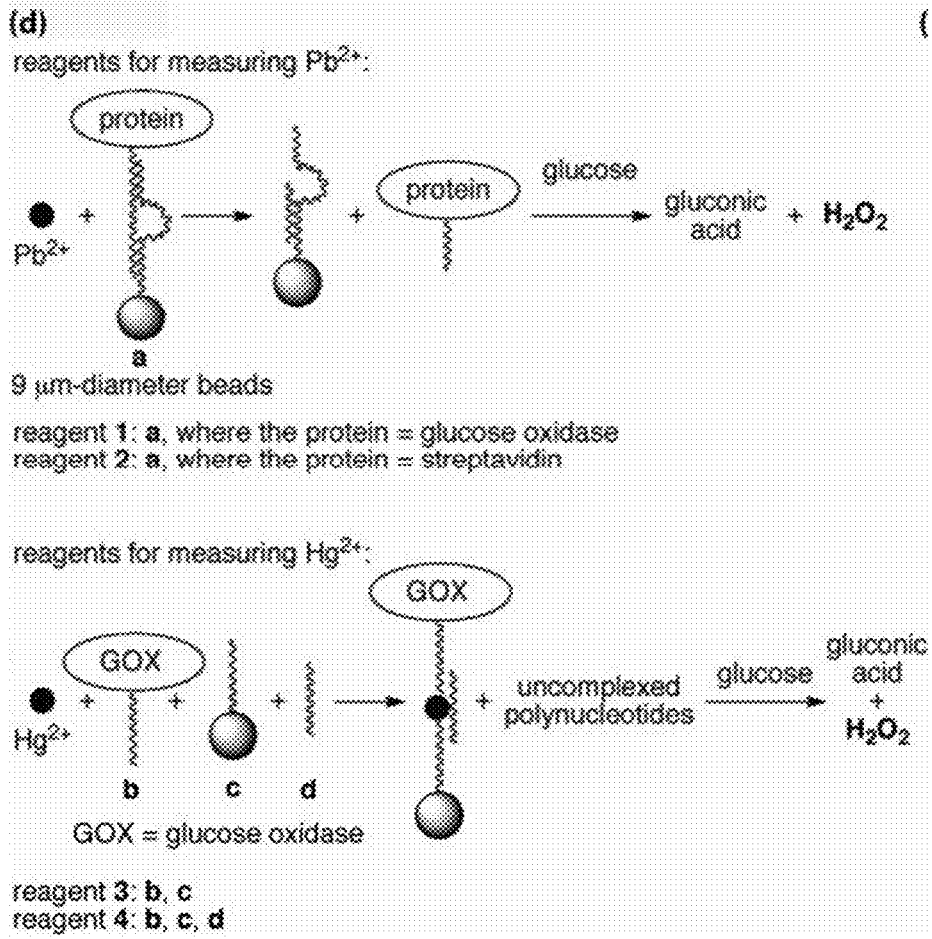
FIG. 25 shows an aptamer-based reagent for a flow-through assay device.
Figure 26:
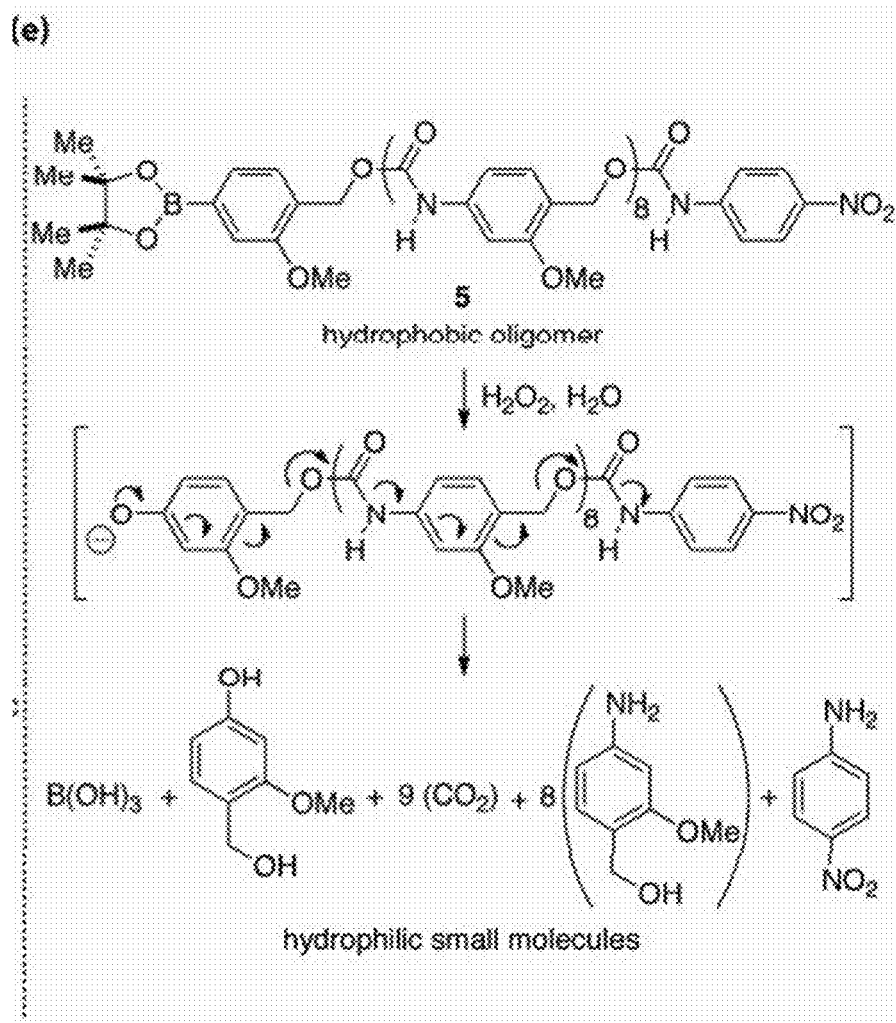
FIG. 26 shows a detection reagent used, along with the mechanism for conversion from hydrophobic to hydrophilic molecules.
Figure 27:
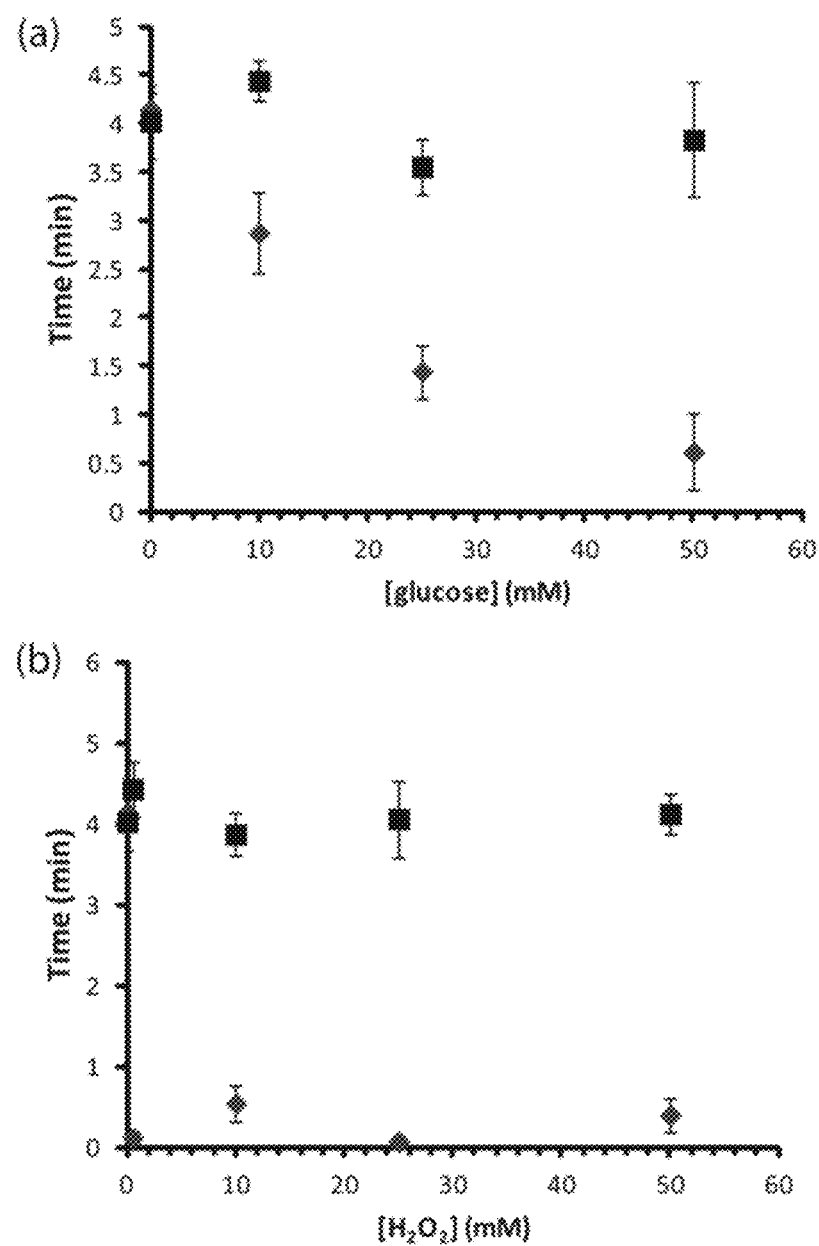
FIGS. 27A and 27B show effects of preproccesing on an assay for adenosine using samples spiked with either glucose or hydrogen peroxide.
Figure 28:
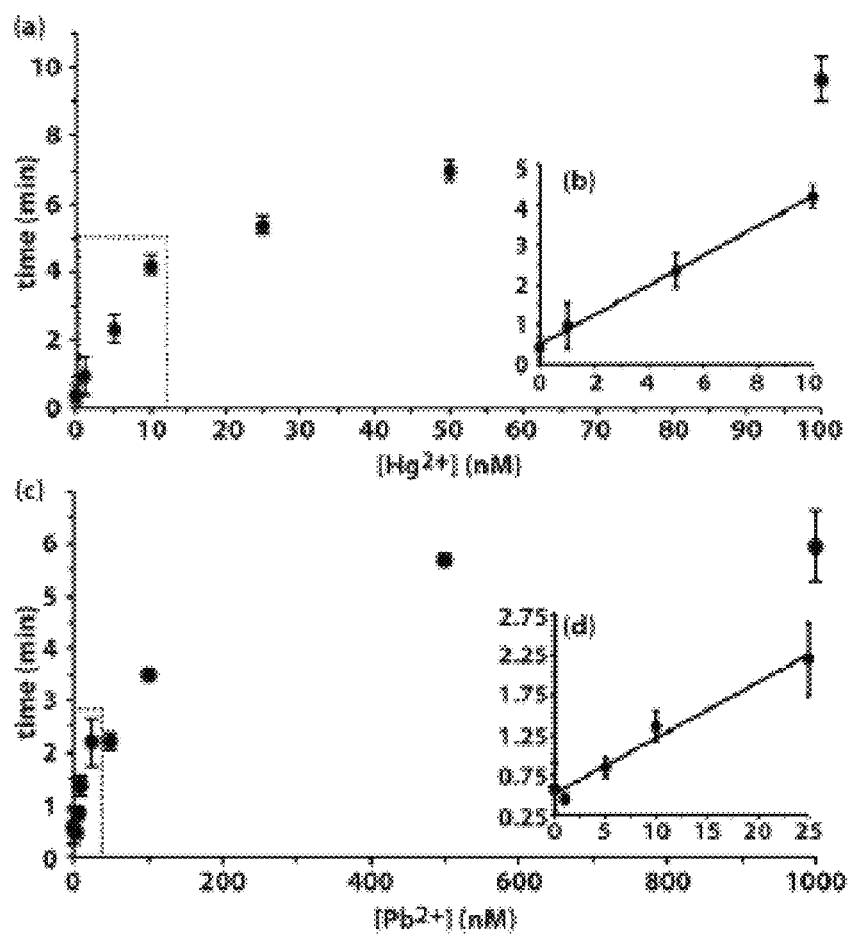
FIGS. 28A-28D show calibration curves for heavy metal analysis.

The sample distributes to the start and stop regions through five layers of wax-patterned paper that are held together via laminate (FIGS. 24-26). Each layer and hydrophilic region in the device serves a unique function to facilitate the assay, with the central hydrophilic region in layer 1 operating as the collection zone where the sample is added to the device. Bead-bound glucose oxidase (GOX) and catalase in layer 2 pre-processes the sample to remove up to 50 mM glucose and hydrogen peroxide that would otherwise interfere with the assay. The beads are embedded in the fibers of the paper, therefore these enzymes should remain fixed in layer 2, whereas the sample distributes to hydrophilic regions of the device.

The 5th layer is a lateral-flow region where the sample moves away from the central sample addition region to the outer columns of hydrophilic paper. In the four lateral-flow channels, the sample re-dissolves reagents for conducting the assays, where each of the four channels contains a different set of reagents (FIG. 25). Reagent 1 is used in the assay for $Pb^{2+}$ and is a bead-bound aptamer complex including two polynucleotides, one of which is a DNAzyme bound to a 9 μm-diameter bead that causes the complex to remain embedded in the paper. The second polynucleotide is covalently bound to GOX and non-covalently associated with the DNAzyme. When $Pb^{2+}$ is present in the sample, it activates the DNAzyme, which cleaves the polynucleotide that is bound to GOX, thus releasing GOX into solution. GOX is then free to travel with the solvent to the outer hydrophilic columns, whereas the remainder of reagent 1 remains in layer 5.

At the outer columns, the sample travels vertically towards the top of the paper-based device. As it passes through layers of paper, the sample encounters additional reagents that were pre-deposited and dried into the layers before the device was assembled. In layer 4, the sample re-dissolves glucose, which is processed by the liberated GOX to generate hydrogen peroxide. Layer 3 contains a hydrophobic poly(benzyl carbamate) oligomer 6 that reacts with hydrogen peroxide via the aryl boronate on one end of the oligomer to initiate a continuous head-to-tail depolymerization reaction (FIG. 26). This depolymerization process changes the wetting properties of layer 3 from hydrophobic back to hydrophilic and allows the sample to travel through this layer with a rate that depends on the concentration of hydrogen peroxide that is generated from the aptamer detection event. The $2^{nd}$ layer contains dried food coloring, which, once re-dissolved, is carried to the top layer where it becomes visible in the appropriate "start" or "stop" region.

The $Pb^{2+}$ assay also contains reagent 2 in the lateral-flow channel opposite to reagent 1. Reagent 2 is exactly the same as reagent 1, with the exception that GOX is replaced with streptavidin. Streptavidin will not generate hydrogen peroxide when it encounters glucose, therefore a sample containing $Pb^{2+}$ will take longer to travel to the viewing region when it encounters reagent 2 than when it encounters reagent 1. This difference in sample transport time may be dependent on the concentration of $Pb^{2+}$ in the sample, thus providing the basis for the time-based measurement and quantitative assay. Moreover, this type of measurement, based on relative sample transport time, normalizes the assays for effects of humidity and sample viscosity that would normally complicate a quantitative measurement.

The $Hg^{2+}$ assay occurs on the same device simultaneously with the $Pb^{2+}$ assay, but requires a different set of reagents in layer 5 than the $Pb^{2+}$ assay (e.g., reagents 3 and 4, FIG. 25). Reagent 4 includes three components: polynucleotide b bound to GOX, polynucleotide c bound to a 9 μm-diameter bead to affix c to the paper, and polynucleotide d, which brings b, c, d, and $Hg^{2+}$ together into a four-component non-covalent complex when $Hg^{2+}$ is present in the sample. This complex prevents the GOX from traveling with the sample through the remainder of the device, and thus minimizes the quantity of hydrogen peroxide that is generated in layer 4 to cause depolymerization in layer 3.

Reagent 3 in the opposite lateral-flow region to reagent 4 contains only polynucleotides b and c, and thus is incapable of forming the four-component complex in the presence of $Hg^{2+}$. In this channel, all of the GOX is capable of generating hydrogen peroxide in layer 4. Hence, the sample travels faster through the region containing reagent 3 than reagent 4, thus reagent 3 leads to the "start" region and reagent 4 to the "stop" region.

Using a device that contains only two channels rather than four (e.g., one channel leading to a "start" region and the other to a "stop" region; FIG. 20), dose-dependent responses were established for $Pb^{2+}$ and $Hg^{2+}$ (FIGS. 28A-D). The limit-of-detection for the $Hg^{2+}$ assay is approximately 4 nM (1 ppb) and the dynamic range extends up to approximately 25 nM (7 ppb), while the complimentary numbers for the $Pb^{2+}$ assay are approximately 4 nM (1 ppb) up to approximately 50 nM (17 ppb). Both of these assays may be sufficiently sensitive to measure the World Health Organization's recommended upper limits for these ions in drinking water (e.g., 22 nM (6 ppb) for $Hg^{2+}$ and 30 nM (10 ppb) for $Pb^{2+}$).

Based on these results in two-channel devices, the four-channel design was implemented for ion analysis in drinking water, as depicted in FIG. 23. The assay times obtained in the four-channel devices are identical to those obtained in the two-channel versions, indicating that the calibration curves in FIG. 28 can be applied to the aforementioned four-channel device. Moreover, FIG. 29 reveals that the multiplexed assays in the four-channel devices are selective for the desired analytes. For example, assay times for samples containing either 100 nM $Pb^{2+}$; 100 nM of $Pb^{2+}$ and $Hg^{2+}$; or 100 nM of $Pb^{2+}$, $Hg^{2+}$, $Cd^{2+}$, and $Zn^{2+}$, all gave identical measurement times for $Pb^{2+}$. Likewise, the measurement time for a sample containing 100 nM $Hg^{2+}$ was identical to times obtained using samples containing $Pb^{2+}$ or a combination of $Pb^{2+}$, $Hg^{2+}$, $Cd^{2+}$, and $Zn^{2+}$.

Figure 29:
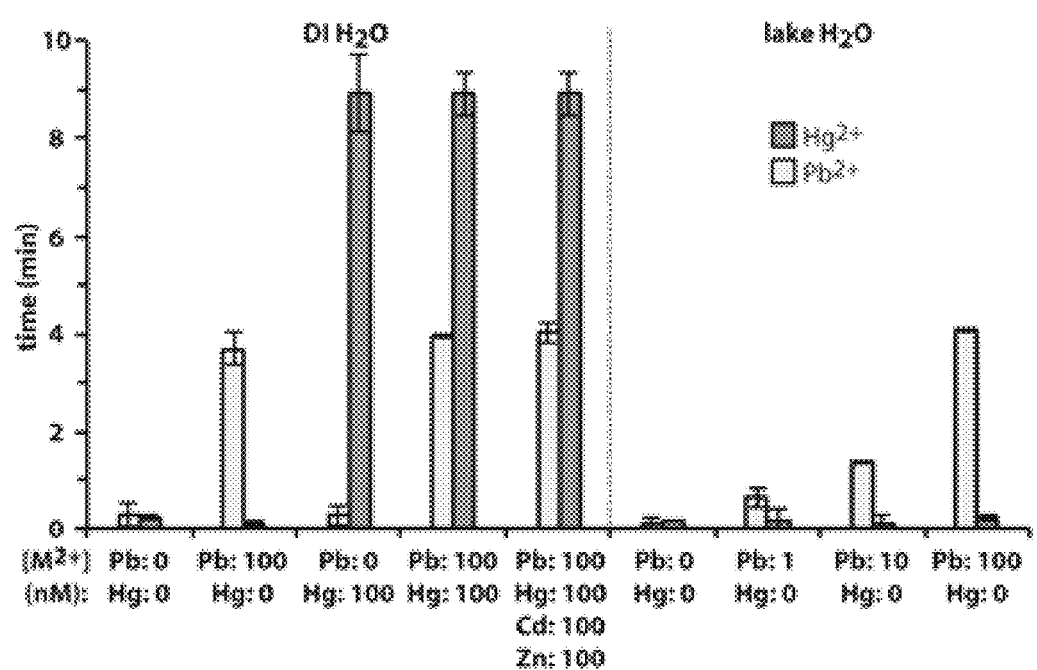
FIG. 29 shows heavy metal analysis of different samples.

Furthermore, the assay platform provides consistent, quantitative measurements even when lake water is used rather than de-ionized water (DI). For example, this observation is shown in FIG. 29 for lake water that was spiked with three different concentrations of $Pb^{2+}$. Comparison of measurement times between DI water and lake water for 100 nM $Pb^{2+}$, in particular, reveals that the assay is minimally affected by contaminants in lake water.

What is claimed is:

1. A capillary-driven device, comprising a hydrophobic detection reagent in a porous media, wherein the hydrophobic reagent changes to hydrophilic by the presence of a target analyte, and wherein the hydrophobic detection reagent is a compound of formula (I),

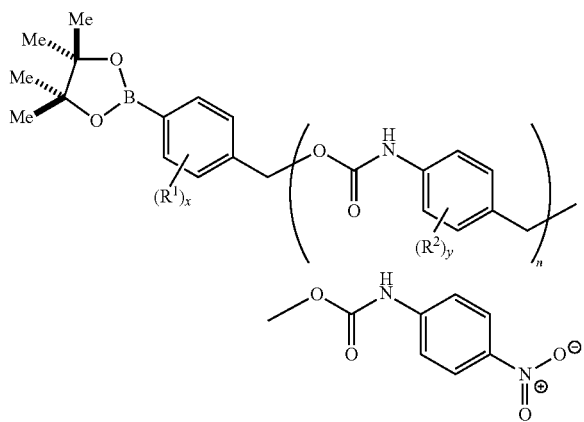

wherein, $R^1$ and $R^2$ are each independently, at each occurrence, selected from the group consisting of hydrogen, $C_1$-$C_6$-alkyl and $C_1$-$C_6$-alkoxy;

x and y are each an integer independently selected from 0, 1, 2, 3, and 4; and n is an integer selected from 0 to 20.

2. The device of claim 1, wherein the device is a capillary-driven vertical flow-through device, a capillary-driven lateral flow-through device, or a combination thereof.

3. The device of claim 1, wherein the hydrophobic detection reagent is an oligomer or polymer.

4. The device of claim 1, wherein the hydrophobic detection reagent is selected from a carbamate, ether, polyether, a poly(phthalaldehyde), a polyvinyl carbamate, a polybenzyl carbamate, or a combination thereof.

5. The device of claim 1, wherein the hydrophobic detection reagent responds to hydrogen peroxide to convert from hydrophobic to hydrophilic molecules.

6. The device of claim 1, wherein $R^1$ and $R^2$ are each $C_1$-$C_6$-alkoxy.

7. The device of claim 1, wherein $R^1$ and $R^2$ are each methoxy.

8. The device of claim 1, wherein n is an integer selected from 0 to 20.

9. The device of claim 1, wherein an assay region of the device comprises one or more responsive agents that select for specific analytes.

10. The device of claim 1, comprising an assay region derivatized with a substrate.

11. The device of claim 1, comprising an immobilized enzyme.

12. The device of claim 1, comprising
a first lateral flow channel leading to a first vertical flow column containing a plurality of treated layers; and
a second lateral flow channel leading to a second vertical flow column containing a plurality of treated layers.

13. The device of claim 12, wherein the second vertical flow column is configured to correct for internal and/or external factors that affect the rate of the sample within the device, except for the effect of the target analyte on the rate.

14. The device of claim 1, comprising a layer containing a dye for visualization of the sample in a visualization layer, wherein the dye in the dye layer is separate from the hydrophobic detection reagent.

15. The device of claim 1, wherein the concentration of an analyte in a sample is determined by measuring the time for the sample to flow through the device after addition of the sample.

16. The device of claim 1, wherein the concentration of an analyte in a sample is determined by visually counting the number of analyte-dependent bars after addition of the sample.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Biotin is coupled to position 1

<400> SEQUENCE: 1
aaaaaaaaaa aacccaggtt ctct                                            24

<210> SEQ ID NO 2
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: Biotin is coupled to position 24

<400> SEQUENCE: 2
tcacaggtaa gtaaaaaaaa aaaa                                            24

<210> SEQ ID NO 3
<211> LENGTH: 50
<212> TYPE: DNA
<213> ORGANISM: Artificial Sequence
<220> FEATURE:
<223> OTHER INFORMATION: Synthetic

<400> SEQUENCE: 3 tttttactc atctgtgaag agaacctggg ggagtattgc ggaggaaggt                  50

<210> SEQ ID NO 4
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Biotin is coupled to position 1

<400> SEQUENCE: 4
aaaaaaaaaa aaacagacat ctcttctccg agccggtcga aataggtgta g              51

<210> SEQ ID NO 5
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Biotin is coupled to position 1

<400> SEQUENCE: 5
aaaaaaaaaa aatgtccgat gctacactat raggaagaga tgtctgt                   47

<210> SEQ ID NO 6
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: Biotin is coupled to position 24

<400> SEQUENCE: 6
tctcaactcg taaaaaaaaa aaaa                                            24

```
<210> SEQ ID NO 7
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Biotin is coupled to position 1

<400> SEQUENCE: 7
aaaaaaaaaa aacgcattca ggat                                    24

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
ttcgtgttgt tcctgtttgc g                                       21
```